United States Patent
Kim

(10) Patent No.: US 9,401,481 B2
(45) Date of Patent: Jul. 26, 2016

(54) COMPOUND AND ORGANIC LIGHT-EMITTING DEVICE INCLUDING THE SAME

(75) Inventor: Young-Kook Kim, Yongin-si (KR)

(73) Assignee: Samsung Display Co., Ltd., Yongin-si (KR)

(*) Notice: Subject to any disclaimer, the term of this patent is extended or adjusted under 35 U.S.C. 154(b) by 456 days.

(21) Appl. No.: 13/595,992

(22) Filed: Aug. 27, 2012

(65) Prior Publication Data

US 2013/0168646 A1   Jul. 4, 2013

(30) Foreign Application Priority Data

Jan. 3, 2012   (KR) .................. 10-2012-0000646

(51) Int. Cl.
| | |
|---|---|
| *C07F 7/10* | (2006.01) |
| *H01L 51/54* | (2006.01) |
| *H01L 51/00* | (2006.01) |
| *C09K 11/06* | (2006.01) |
| *C07B 59/00* | (2006.01) |

(Continued)

(52) U.S. Cl.
CPC .......... *H01L 51/0059* (2013.01); *C07B 59/004* (2013.01); *C07F 7/0818* (2013.01); *C09K 11/06* (2013.01); *H01L 51/006* (2013.01); *H01L 51/0061* (2013.01); *H01L 51/0094* (2013.01); *H01L 51/0077* (2013.01); *H01L 51/0081* (2013.01); *H01L 51/0085* (2013.01); *H01L 51/0087* (2013.01); *H01L 51/0088* (2013.01); *H01L 51/5012* (2013.01)

(58) Field of Classification Search
CPC ............. H01L 51/0059; H01L 51/006; H01L 51/0061; H01L 51/0094; H01L 51/0077; H01L 51/0081; H01L 51/0087; H01L 51/0088; H01L 51/5012; H01L 51/0085; C07F 7/0818; C07B 59/004
See application file for complete search history.

(56) References Cited

U.S. PATENT DOCUMENTS

| 5,635,308 A | 6/1997 | Inoue et al. |
|---|---|---|
| 5,645,948 A | 7/1997 | Shi et al. |
| 5,972,247 A | 10/1999 | Shi et al. |

(Continued)

FOREIGN PATENT DOCUMENTS

| JP | 8-12600 | 1/1996 |
|---|---|---|
| JP | 2000-3782 A | 1/2000 |

(Continued)

OTHER PUBLICATIONS

Lin et al., Eur. J. Org. Chem., (2011), pp. 912-921.*

(Continued)

*Primary Examiner* — Dawn Garrett
(74) *Attorney, Agent, or Firm* — Lewis Roca Rothgerber Christie LLP

(57) ABSTRACT

Compounds represented by Formula 1 and organic light-emitting devices including an organic layer including the compounds are disclosed.

Formula 1

20 Claims, 1 Drawing Sheet

(51) Int. Cl.
*C07F 7/08* (2006.01)
*H01L 51/50* (2006.01)

(56) References Cited

U.S. PATENT DOCUMENTS

| | | | |
|---|---|---|---|
| 6,232,001 B1 * | 5/2001 | Igarashi | 428/690 |
| 6,465,115 B2 | 10/2002 | Shi et al. | |
| 6,596,415 B2 | 7/2003 | Shi et al. | |
| 2001/0014752 A1 * | 8/2001 | Igarashi | 556/465 |
| 2005/0019602 A1 * | 1/2005 | Sellinger | 428/690 |
| 2007/0048546 A1 * | 3/2007 | Ren | 428/690 |
| 2008/0004445 A1 | 1/2008 | Hosokawa et al. | |
| 2008/0106188 A1 | 5/2008 | Hwang et al. | |
| 2008/0224129 A1 * | 9/2008 | Choi et al. | 257/40 |
| 2009/0045734 A1 | 2/2009 | Moon et al. | |
| 2009/0206740 A1 * | 8/2009 | Chun et al. | 313/504 |
| 2009/0261711 A1 | 10/2009 | Ito et al. | |
| 2010/0187511 A1 | 7/2010 | Funahashi et al. | |
| 2010/0237329 A1 | 9/2010 | Jung et al. | |

FOREIGN PATENT DOCUMENTS

| | | | |
|---|---|---|---|
| JP | 2001-234159 A * | 8/2001 | |
| JP | 2006-273737 A | 10/2006 | |
| JP | 2010-257589 | 11/2010 | |
| KR | 10-2004-0099798 | 12/2004 | |
| KR | 10-2008-0041941 | 5/2008 | |
| KR | 10-2008-0052589 | 6/2008 | |
| KR | 10-2008-0088107 | 10/2008 | |
| KR | 10-2008-0102002 | 11/2008 | |
| KR | 10-2008-0109850 | 12/2008 | |
| KR | 10-2009-0018489 | 2/2009 | |
| KR | 10-2010-0017849 | 2/2010 | |
| KR | 10-2010-0130059 A | 12/2010 | |
| KR | 10-2011-0068239 | 6/2011 | |
| WO | WO 2010/140801 A1 | 12/2010 | |

OTHER PUBLICATIONS

Lee et al., Journal of Organometallic Chemistry, 691, (2006), pp. 1887-1896.*
Wahab et al., Chem. Mater., (2008), vol. 20, pp. 1855-1861.*
Lim et al., Journal of the American Chemical Society, (2011), vol. 133, pp. 1375-1382.*
Adachi, et al., *Confinement of charge carriers and molecular excitons within 5-nm-thick emitter layer in organic electroluminescent devices with a double heterostructure*, Appl. Phys. Lett. 57 (6), Aug. 6, 1990, pp. 531-533, American Institute of Physics, Japan.
Sakamoto, et al., *Synthesis, Characterization, and Electron-Transport Property of Perfluorinated Phenylene Dendrimers*, J. Am. Chem. Soc. 2000, 122, 2000 American Chemical Society, pp. 1832-1833, Japan.
Yamaguchi, et al., *Diphenylamino-Substituted 2,5-Diarylsiloles for Single-Layer Organic Electroluminescent Devices*, Chemistry Letters 2001, The Chemical Society of Japan, pp. 98-99, Japan.
Tang, et al., *Organic electroluminescent diodes*, Appl. Phys. Lett. 51 (12), Sep. 21, 1987, American institute of Physics, pp. 913-915.
Taiwanese Office action dated Jan. 18, 2016, with English translation, for corresponding Taiwan Patent application 101136765, (10 pages).

* cited by examiner

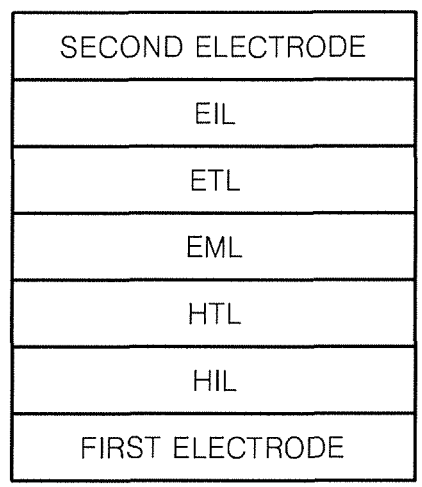

COMPOUND AND ORGANIC LIGHT-EMITTING DEVICE INCLUDING THE SAME

CROSS-REFERENCE TO RELATED PATENT APPLICATION

This application claims priority to and the benefit of Korean Patent Application No. 10-2012-0000646, filed on Jan. 3, 2012 in the Korean Intellectual Property Office, the entire content of which is incorporated herein by reference.

BACKGROUND

1. Technical Field

The present invention relates to a vinylsilane compound represented by Formula 1 and to an organic light-emitting device including the vinylsilane compound.

2. Description of the Related Art

Light-emitting devices are self-emission type display devices that have wide viewing angles, high contrast ratios, and short response times. Due to these characteristics, light-emitting devices are drawing more attention. Such light-emitting devices can be roughly classified into inorganic light-emitting devices that include emission layers containing inorganic compounds, and organic light-emitting devices that include emission layers containing organic compounds. Specifically, organic light-emitting devices have higher luminance, lower driving voltages, and shorter response times than inorganic light-emitting devices, and can render multi-colored displays. Thus, much research into such organic light-emitting devices has been conducted.

Typically, an organic light-emitting device has a stacked structure that included an anode, a cathode, and an organic emission layer between the anode and cathode. However, a hole injection layer and/or a hole transport layer may be stacked between the anode and the organic emission layer, and/or an electron injection layer may be stacked between the organic emission layer and the cathode. In other words, an organic light-emitting device may have a stacked structure of anode/hole transport layer/organic emission layer/cathode or a stacked structure of anode/hole transport layer/organic emission layer/electron transport layer/cathode.

As the material for forming the organic emission layer, anthracene derivatives have been widely used. Light emitted from most known light-emitting materials is bluish green instead of deep blue in terms of the color purity of emitted blue light. In addition, when light-emitting materials are used in an organic light-emitting device, most organic light-emitting devices do not have sufficiently long half-lives and thus are not commercially viable.

SUMMARY OF THE INVENTION

Embodiments of the present invention provide a novel vinylsilane compound having improved electrical characteristics, charge transporting capabilities and light-emission capabilities.

Embodiments of the present invention provide an organic light-emitting device including the vinylsilane compound.

Embodiments of the present invention provide a flat panel display device including the organic light-emitting device.

According to embodiments of the present invention, a vinylsilane compound is represented by Formula 1 below:

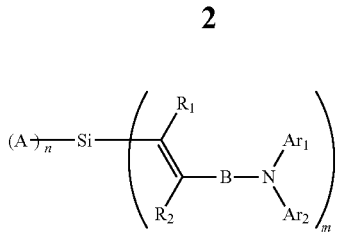

Formula 1

In Formula 1, each A is independently a substituted or unsubstituted $C_1$-$C_{60}$ alkyl group, a substituted or unsubstituted $C_1$-$C_{60}$ alkoxy group, a substituted or unsubstituted $C_5$-$C_{60}$ aryl group, or a substituted or unsubstituted $C_3$-$C_{60}$ heteroaryl group. $R_1$ and $R_2$ are each independently a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_5$-$C_{60}$ aryl group, or a substituted or unsubstituted $C_3$-$C_{60}$ heteroaryl group. B may be a bivalent linker and may be a substituted or unsubstituted $C_1$-$C_{60}$ alkylene group, a substituted or unsubstituted $C_5$-$C_{60}$ arylene group, or a substituted or unsubstituted $C_3$-$C_{60}$ heteroarylene group. $Ar_1$ and $Ar_2$ are each independently a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group. $Ar_1$ and $Ar_2$ are optionally linked to form a ring, n is an integer from 0 to 3, m is an integer from 1 to 4, and n+m=4.

In some embodiments, each A may be independently a substituted or unsubstituted $C_1$-$C_{30}$ alkyl group, a substituted or unsubstituted $C_5$-$C_{30}$ aryl group, or a substituted or unsubstituted $C_3$-$C_{30}$ heteroaryl group, In some embodiments, $R_1$ and $R_2$ may be each independently a hydrogen atom, a deuterium atom, a substituted or unsubstituted $C_1$-$C_{30}$ alkyl group, a substituted or unsubstituted $C_3$-$C_{30}$ cycloalkyl group, a substituted or unsubstituted $C_5$-$C_{30}$ aryl group, or a substituted or unsubstituted $C_3$-$C_{30}$ heteroaryl group.

In some embodiments, B may be a bivalent linker and may be a substituted or unsubstituted $C_5$-$C_{30}$ arylene group or a substituted or unsubstituted $C_3$-$C_{30}$ heteroarylene group.

In some embodiments, $Ar_1$ and $Ar_2$ may be each independently a substituted or unsubstituted $C_5$-$C_{30}$ aryl group, a substituted or unsubstituted $C_3$-$C_{30}$ heteroaryl group, or a substituted or unsubstituted $C_6$-$C_{30}$ condensed polycyclic group.

In some embodiments, in Formula 1 above, $R_1$ and $R_2$ may be each independently a hydrogen atom or a deuterium atom.

In some embodiments, in Formula 1 above, A may be a hydrogen atom, a deuterium atom, a halogen atom, a cyano group, a substituted or unsubstituted $C_1$-$C_{20}$ alkyl group, or any one of Formulae 2a through 2d below:

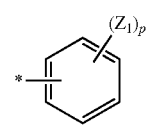

2a

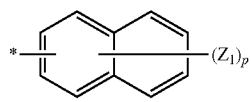

2b

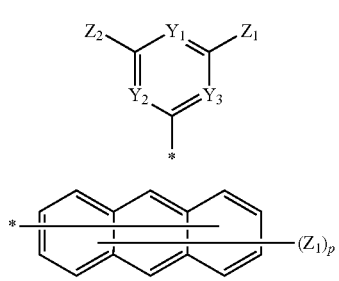

2c

2d

In Formulae 2a through 2d, each of $Y_1$, $Y_2$, and $Y_3$ may independently be a linker represented by —N=, —N($R_{20}$)—, or —C($R_{21}$)=. Each of $Z_1$, $Z_2$, $R_{20}$, and $R_{21}$ may be independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group. p may be an integer from 1 to 12. * may indicate a binding site.

In Formula 1 above, each of $Ar_1$ and $Ar_2$ may be independently any one of compounds represented by Formulae 3a through 3f below:

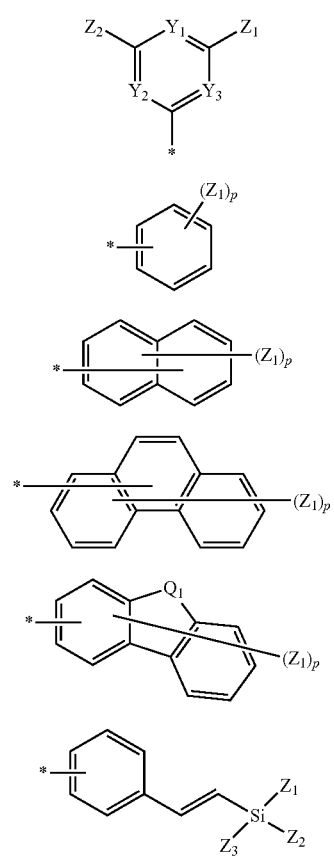

3a

3b

3c

3d

3e

3f

In Formulae 3a through 3f above, $Q_1$ may be a linker represented by —C($R_{30}$)($R_{31}$)—, —N($R_{32}$)—, —S—, or —O—. Each of $Y_1$, $Y_2$, and $Y_3$ may be a linker independently represented by —O—, —N=, —N($R_{20}$)—, or —C($R_{21}$)=.

Each of $Z_1$, $Z_2$, $Z_3$, $R_{20}$, $R_{21}$, $R_{30}$, $R_{31}$, and $R_{32}$ may be independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group. p may be an integer from 1 to 12. r may be an integer from 0 to 5. * may indicate a binding site.

In some embodiments, in Formula 1 above, B may be a linker represented by any one of Formulae 4a to 4i below, or a linker obtained by linking two or more compounds represented by Formulae 4a to 4i below:

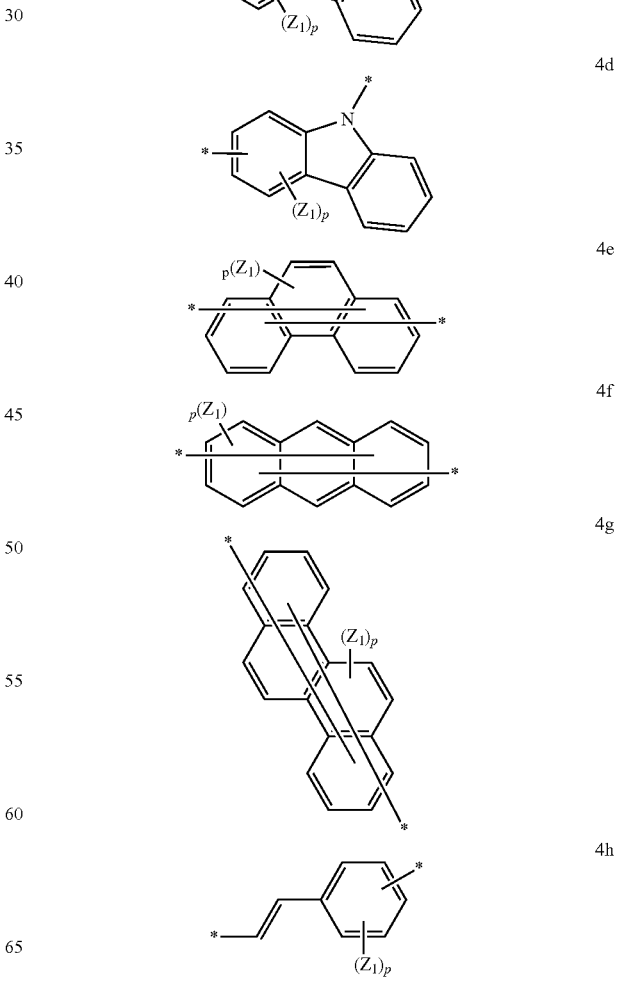

4a

4b

4c

4d

4e

4f

4g

4h

-continued

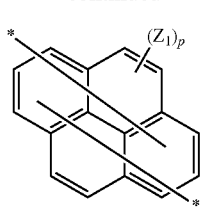

In Formulae 4a through 4i above, $Q_1$ may be a linker represented by —C($R_{30}$)($R_{31}$)—, —N($R_{32}$)—, —S—, or —O—. Each of $Y_1$, $Y_2$, and $Y_3$ may independently be a linker represented by —O—, —N=, —N($R_{20}$)—, or —C($R_{21}$)=. Each of $Z_1$, $R_{20}$, $R_{21}$, $R_{30}$, $R_{31}$, and $R_{32}$ may be independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group. p may be an integer from 1 to 12. * may indicate a binding site.

In some embodiments, the vinylsilane compound represented by Formula 1 above may be any one of the Compounds below:

1
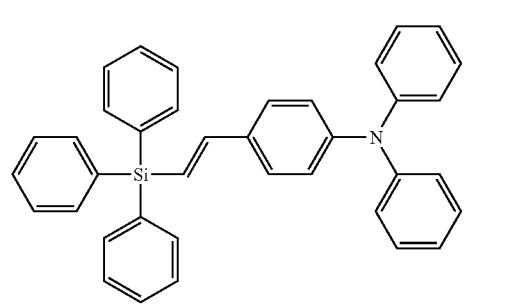

2
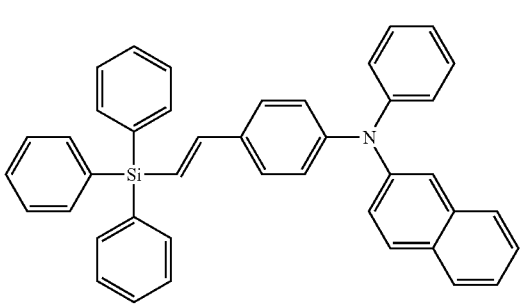

3
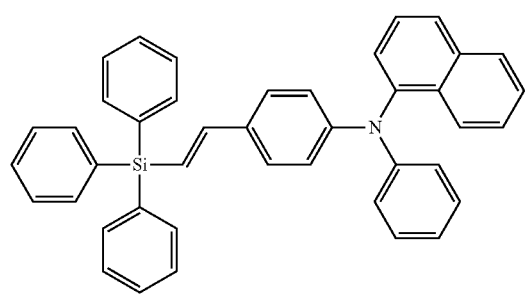

4
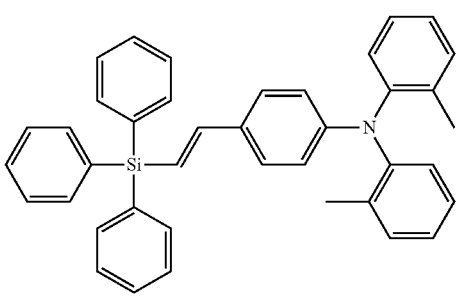

5
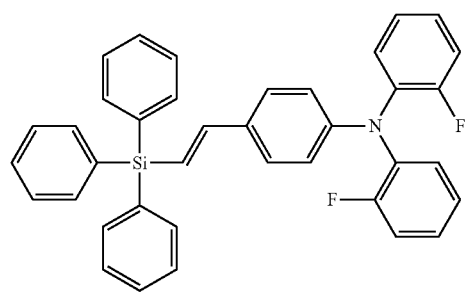

6
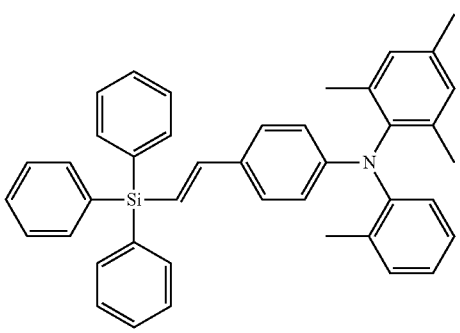

7
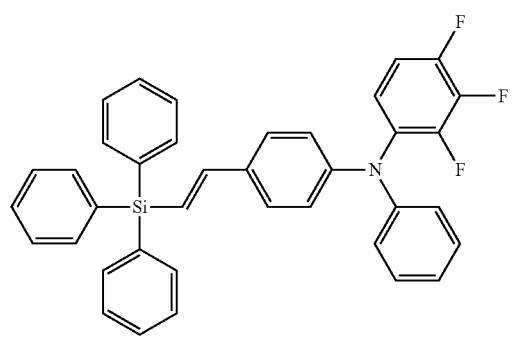

8
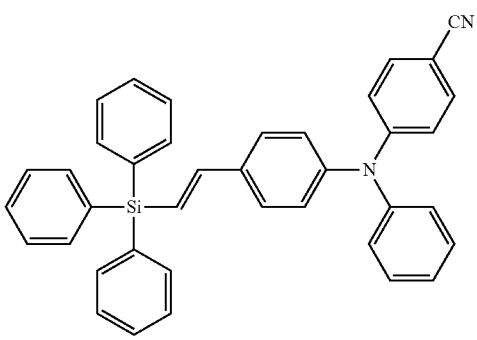

9
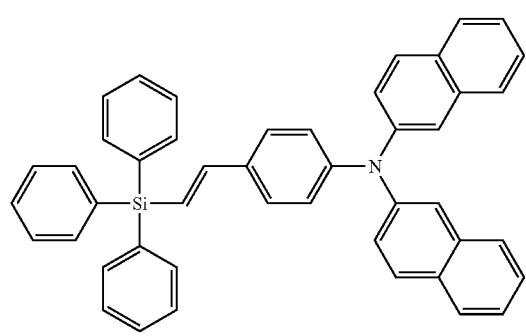
10
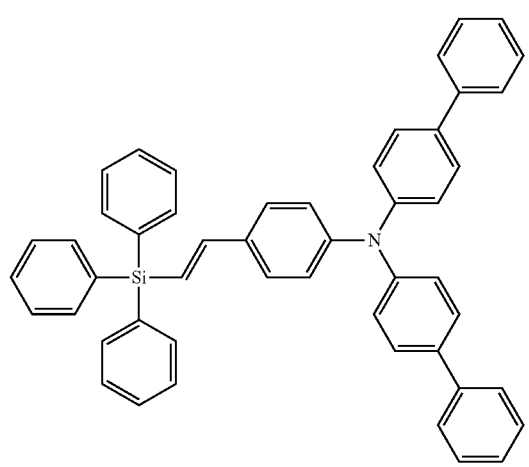
11
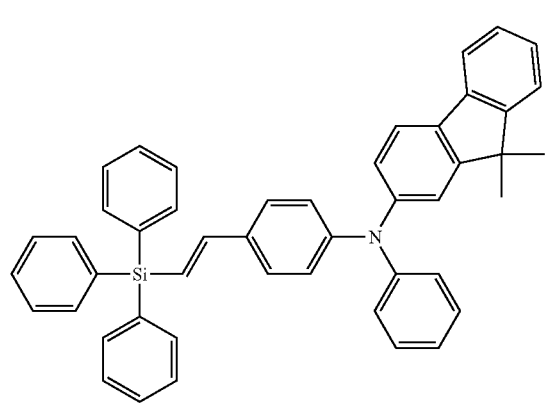
12
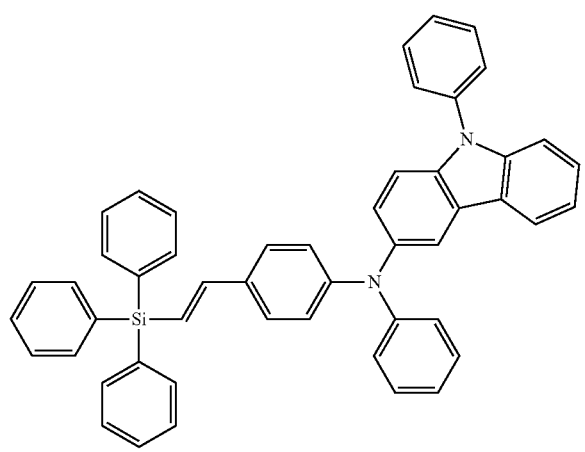
13
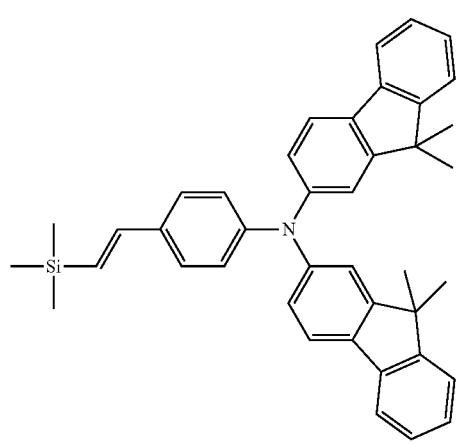
14
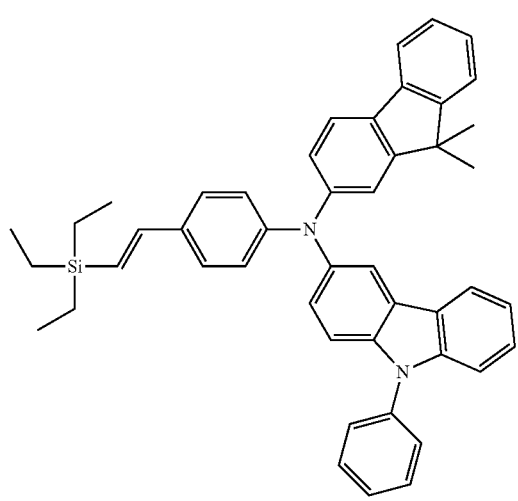

15
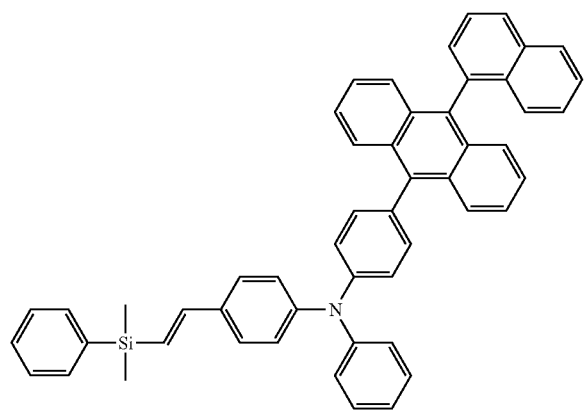
16
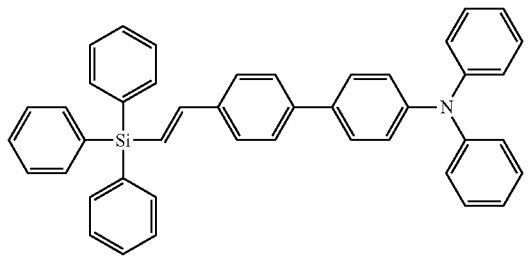
17
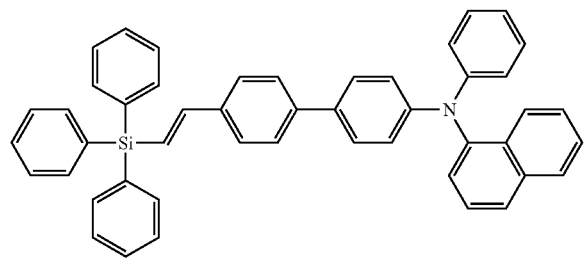
18
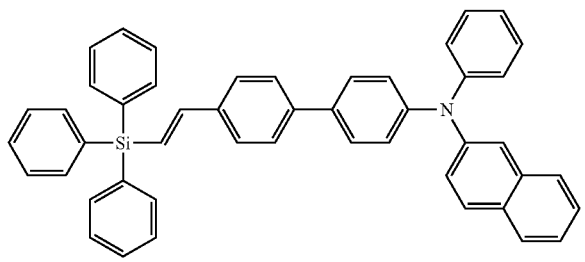
19
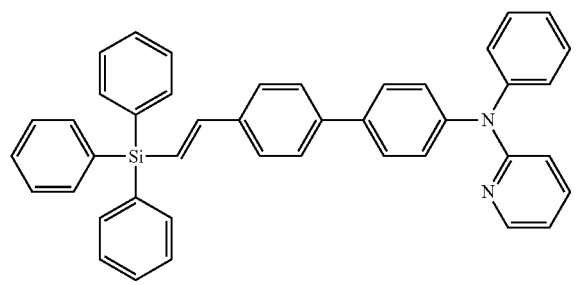
20
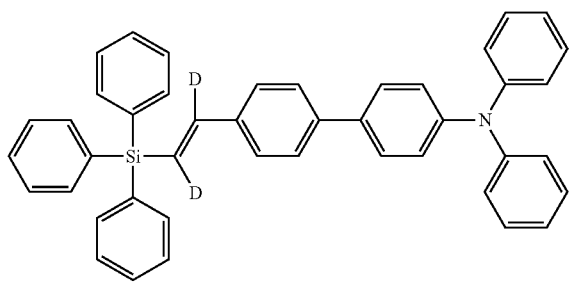
21
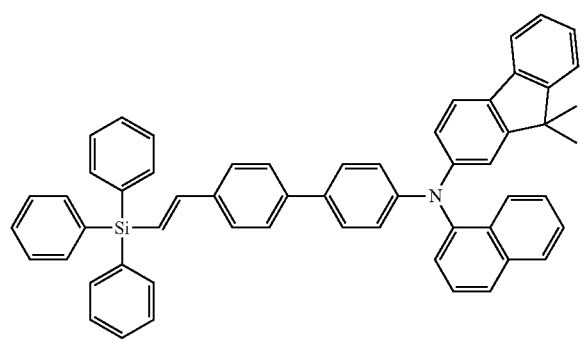
22
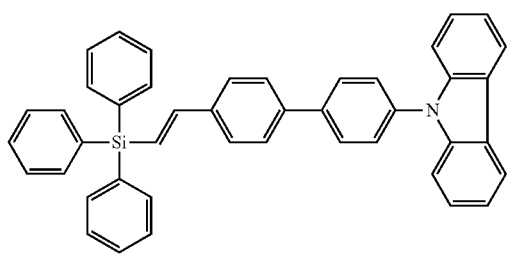

23
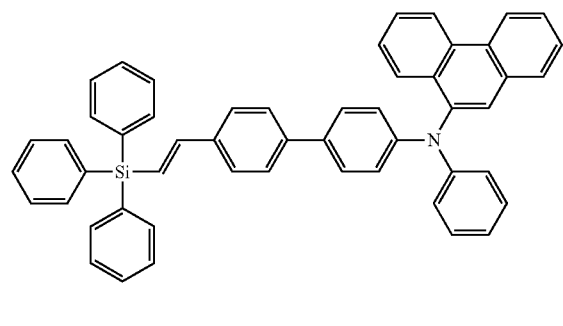
24
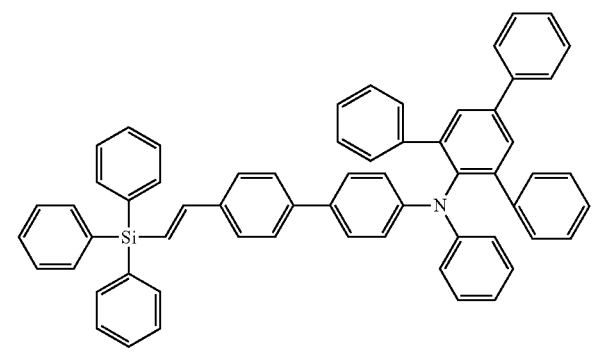
25
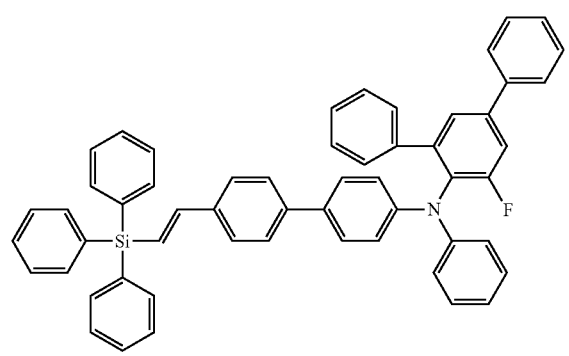
26
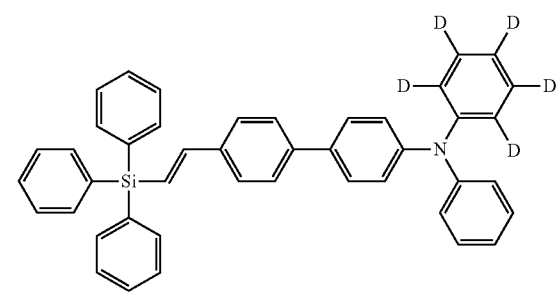
27
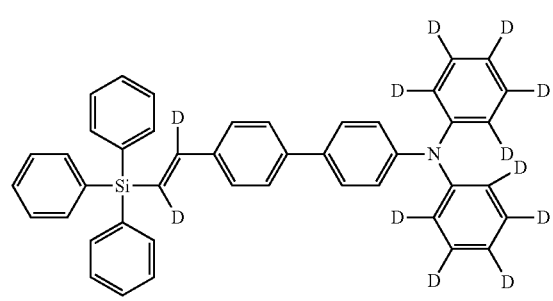
28
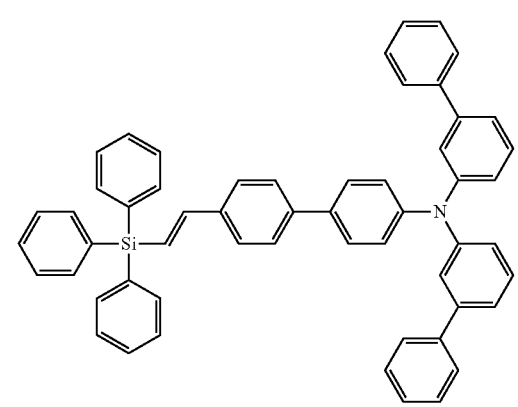
29
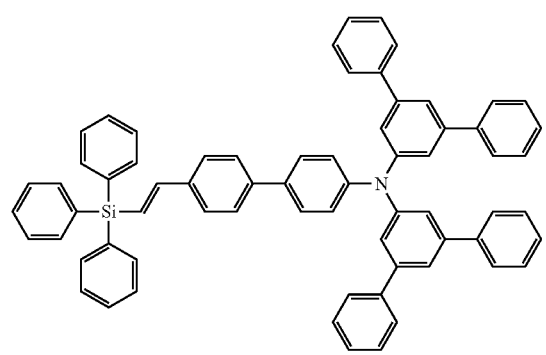
30
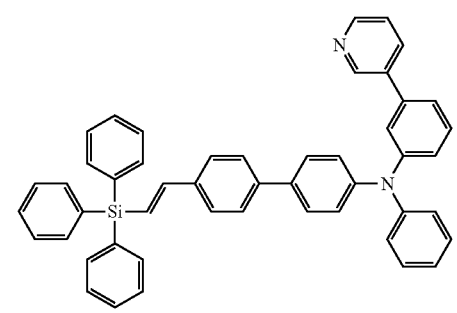

-continued
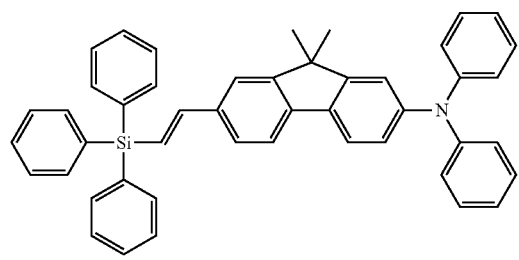
31
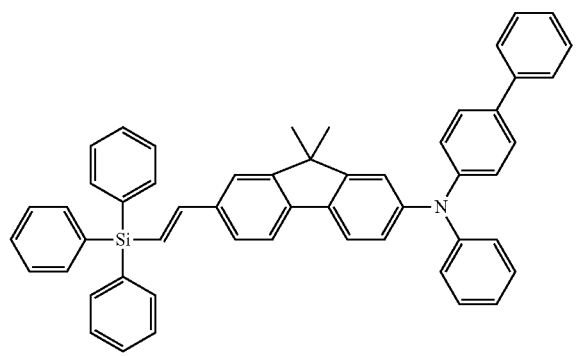
32
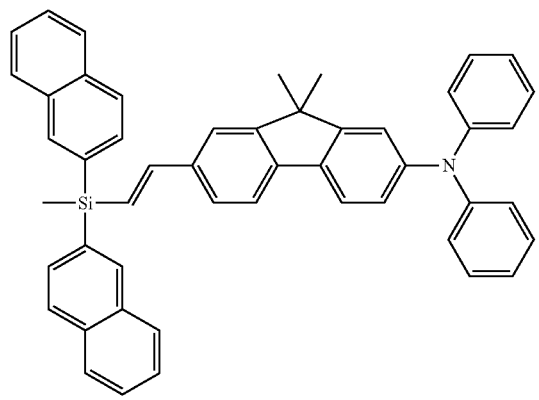
33
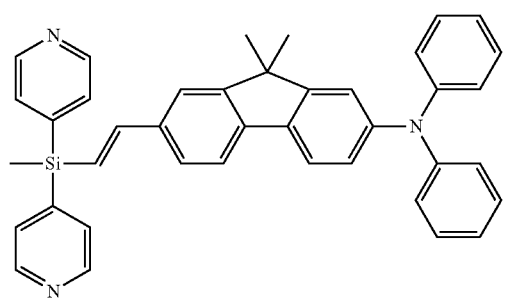
34
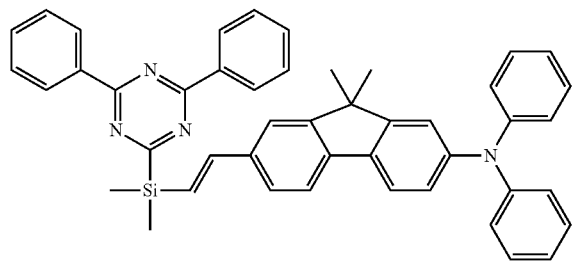
35
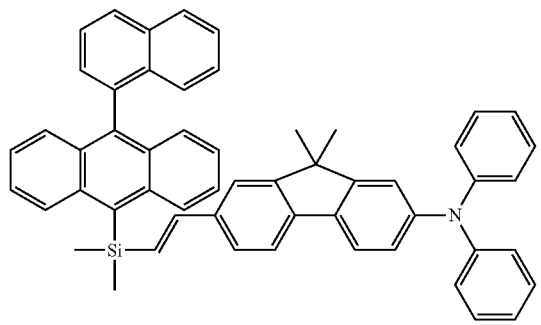
36
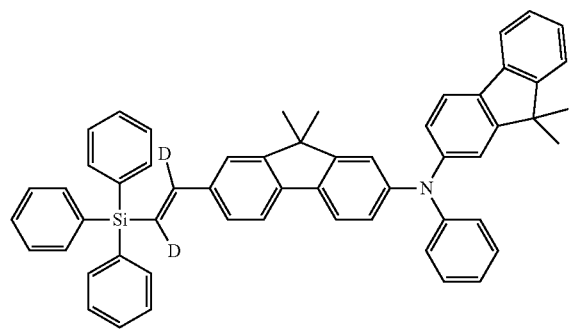
37
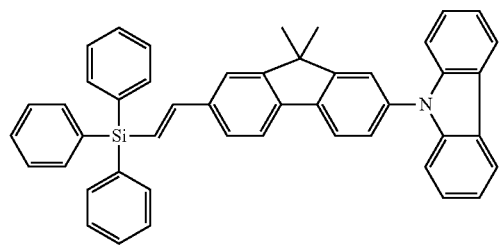
38

-continued
39
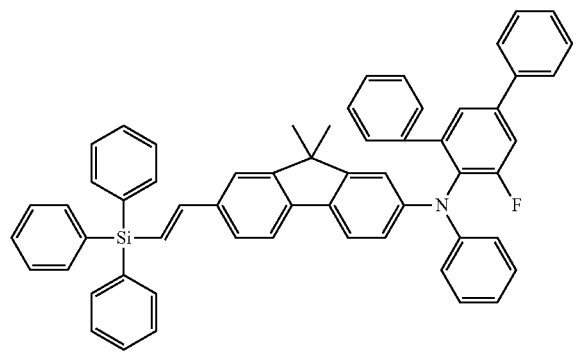
40
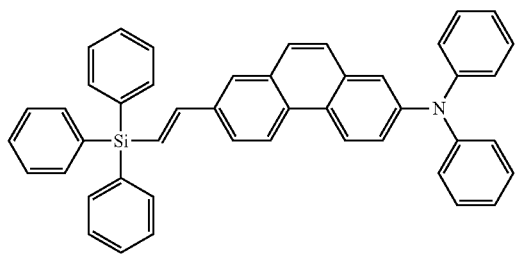
41
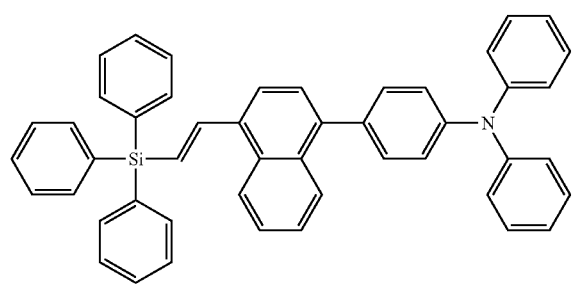
42
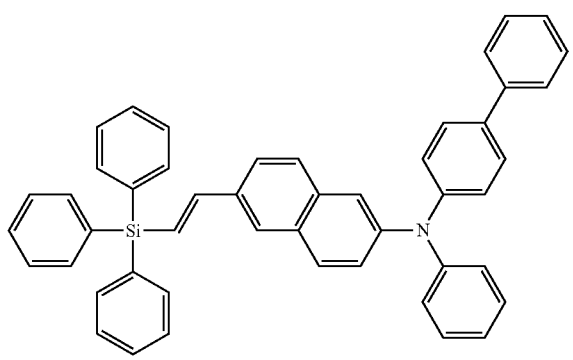
43
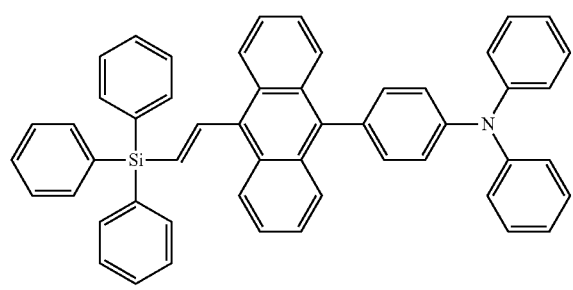
44
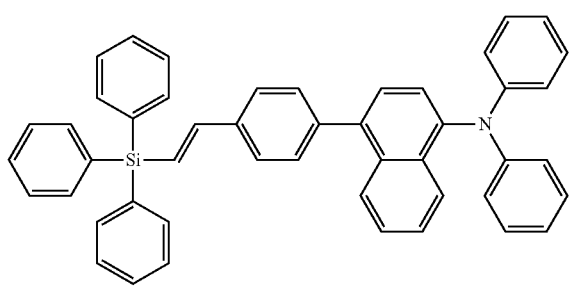
45
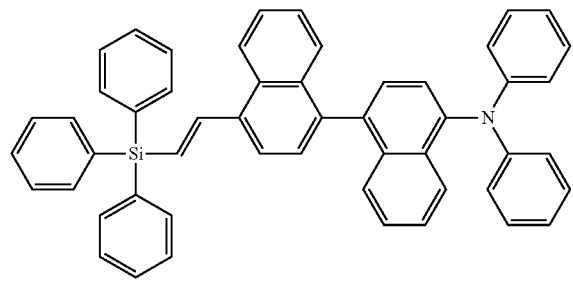
46
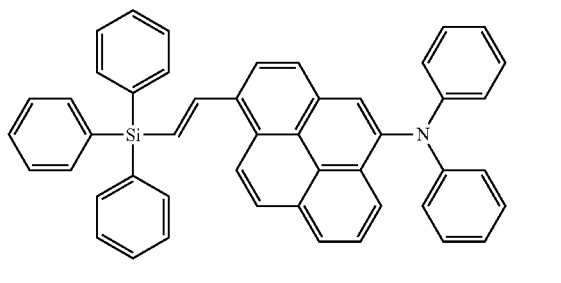

-continued
47
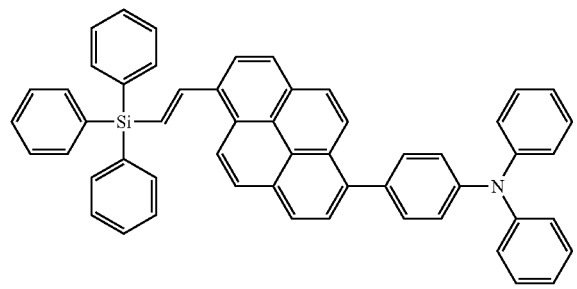
48
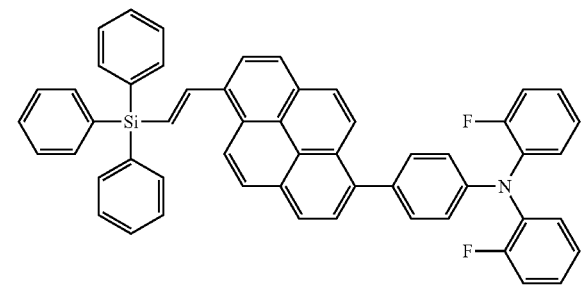
49
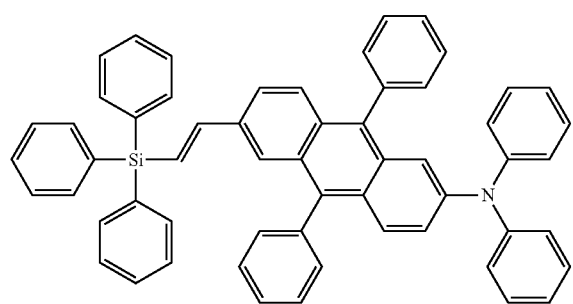
50
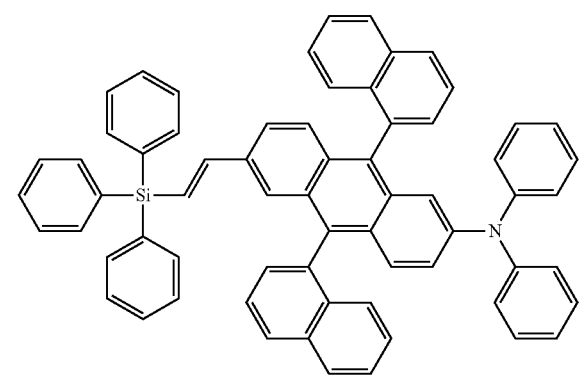
51
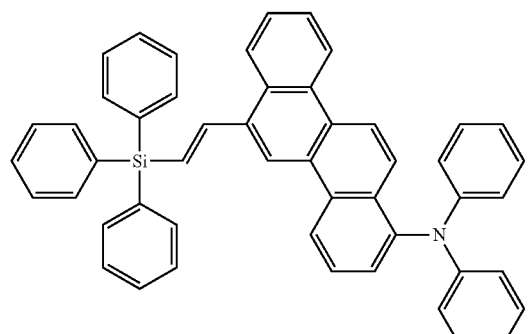
52
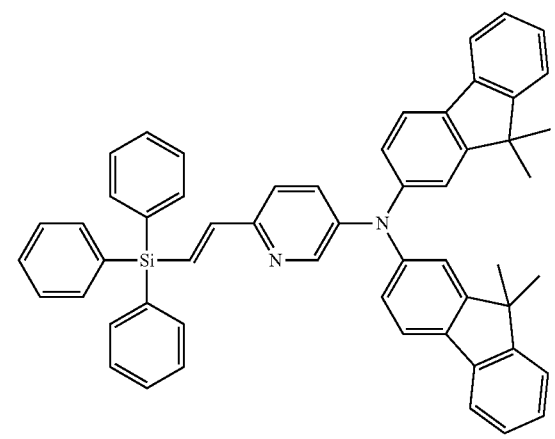
53
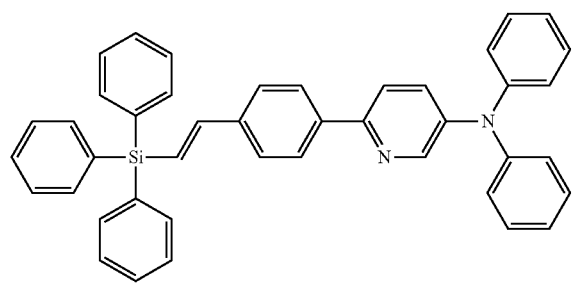
54
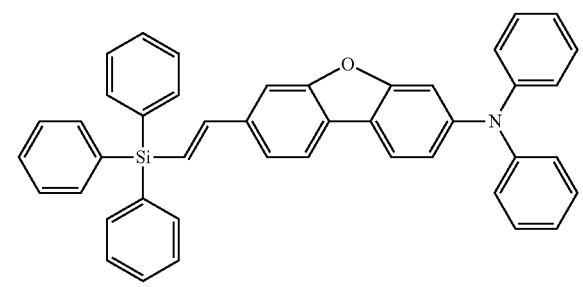

-continued
55
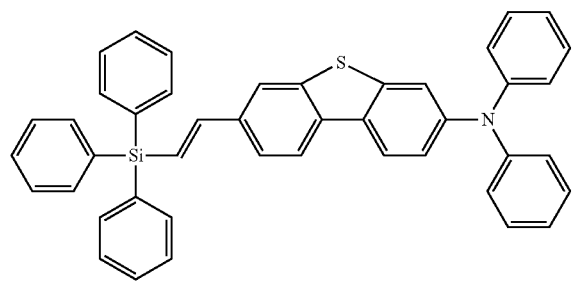
56
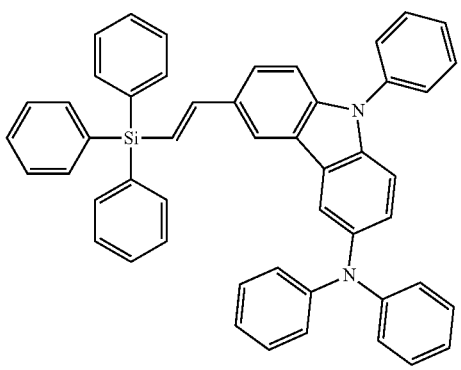
57
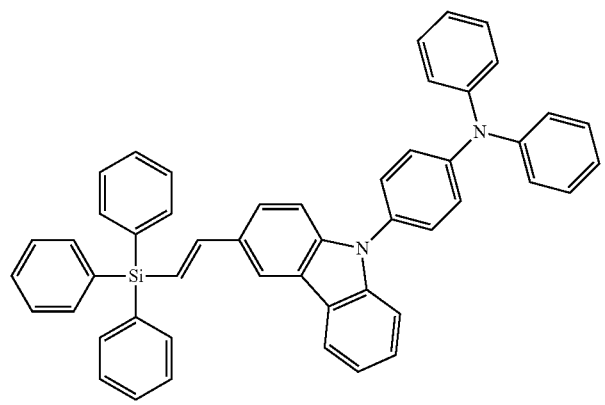
58
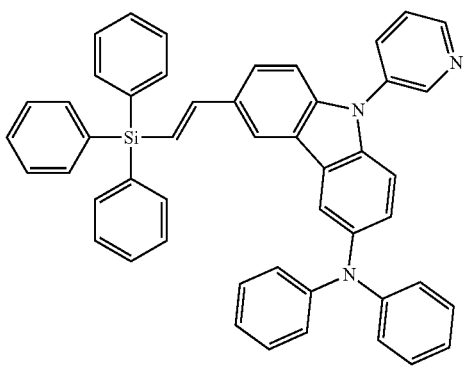
59
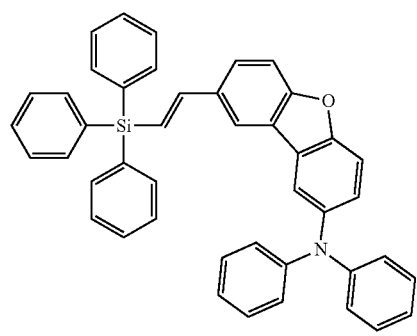
60
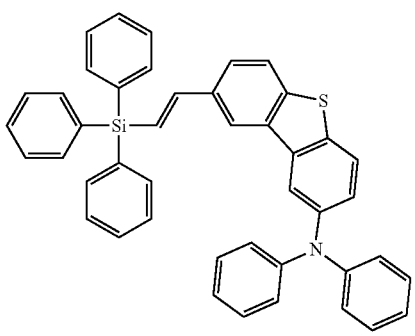
61
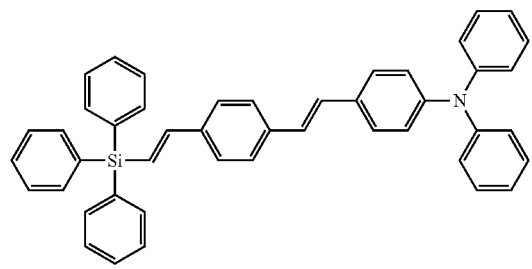
62
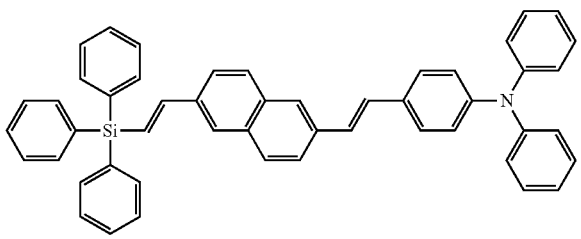

63
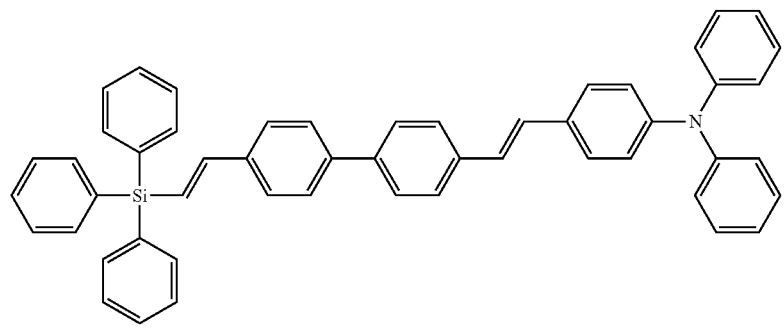
64
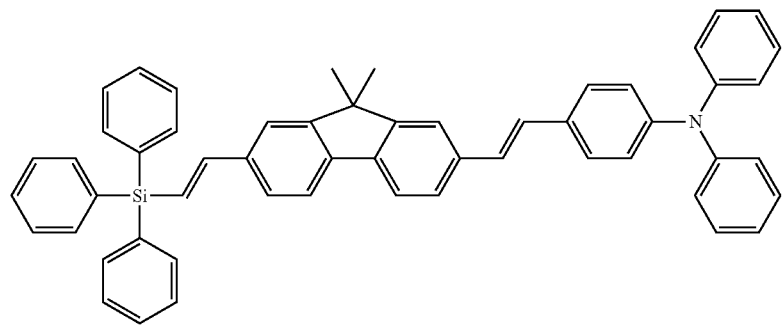
65
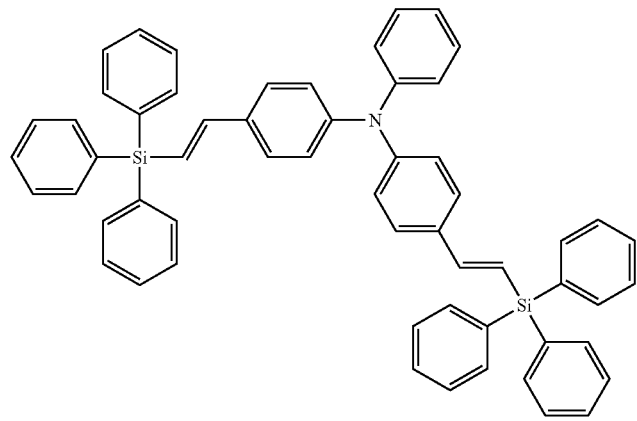
66
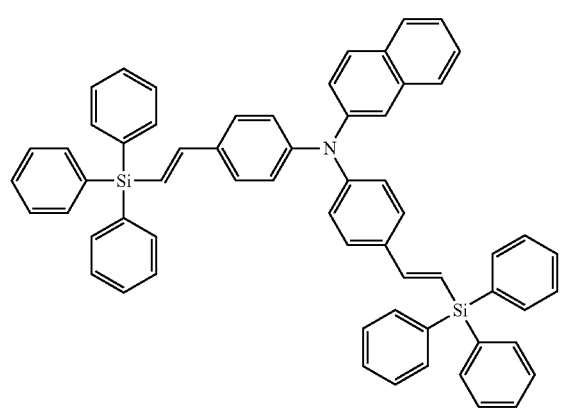
67
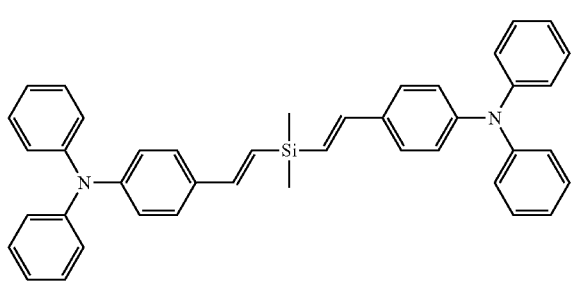

-continued

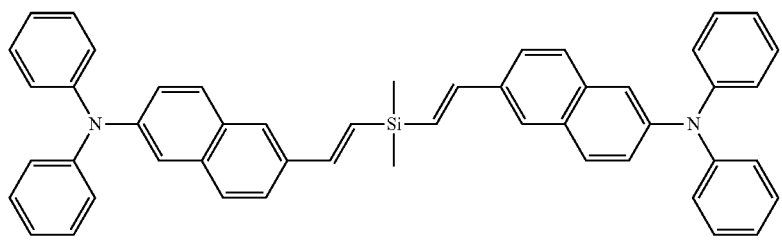
68

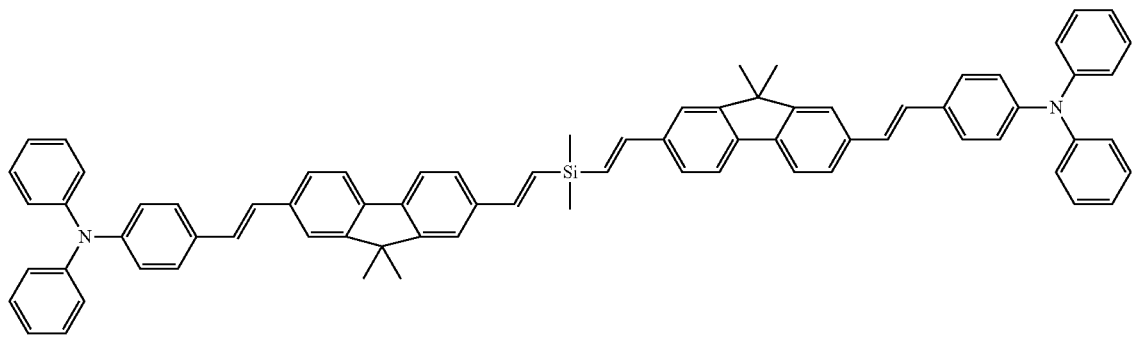
69

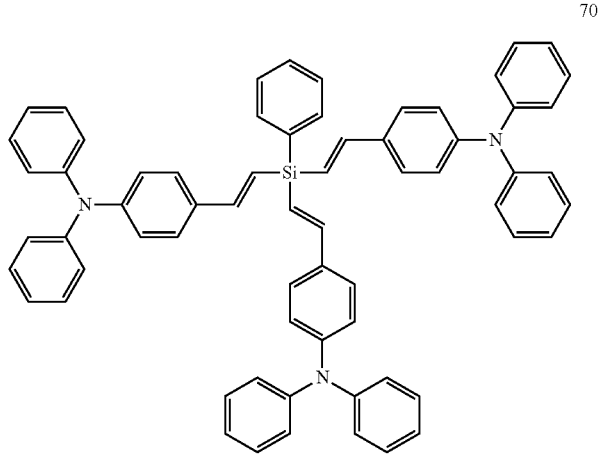
70

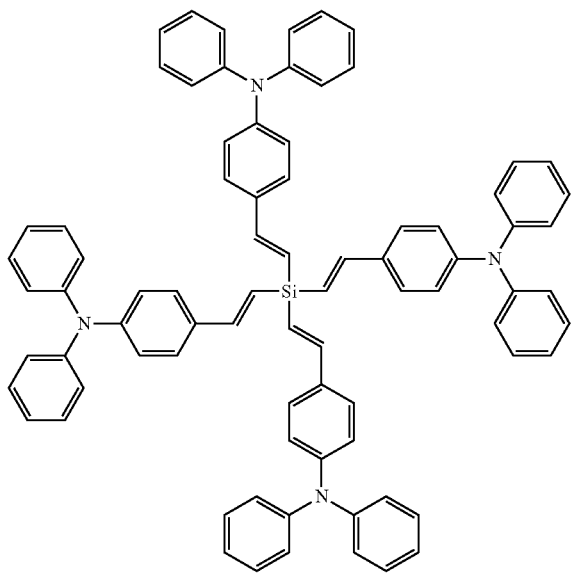
71

According to another embodiment of the present invention, an organic light-emitting device includes a first electrode; a second electrode; and an organic light-emitting layer between the first electrode and the second electrode, where the organic layer includes the vinylsilane compound.

The organic layer may be an emission layer and the vinylsilane compound may be used as a host for a fluorescent or phosphorescent device.

The organic layer may be an emission layer and the vinylsilane compound may be used as a fluorescent dopant.

The organic layer may include a hole injection layer, a hole transport layer, or a functional layer having both hole injection and hole transport capabilities.

The organic light-emitting device may include an emission layer, a hole injection layer, a hole transport layer, or a functional layer having both hole injection and hole transport capabilities, and either the emission layer, the hole injection layer, the hole transport layer, or the functional layer having both hole injection and hole transport capabilities may include the vinylsilane compound, and the emission layer may include an anthracene-based compound.

The organic light-emitting device may include an emission layer, a hole injection layer, a hole transport layer, or a functional layer having both hole injection and hole transport capabilities, and either the emission layer, the hole injection layer, the hole transport layer, or the functional layer having both hole injection and hole transport capabilities may include the vinylsilane compound, and the emission layer may include an arylamine-based compound.

The organic light-emitting device may include an emission layer, a hole injection layer, a hole transport layer, or a functional layer having both hole injection and hole transport capabilities, and either the emission layer, the hole injection layer, the hole transport layer, or the functional layer having both hole injection and hole transport capabilities may include the vinylsilane compound, and the emission layer may include a styryl-based compound.

The organic light-emitting device may include an emission layer, a hole injection layer, a hole transport layer, or a functional layer having both hole injection or hole transport capabilities, and either the hole injection layer, the hole transport layer, or the functional layer having both hole injection or hole transport capabilities may include the vinylsilane compound, and any one of a red layer, a green layer, and a white layer of the emission layer may include a phosphorescent compound.

The hole injection layer, the hole transport layer, or the functional layer having both hole injection and hole transport capabilities may include a charge generating material.

The charge generating material may include a p-dopant, and the p-dopant may include a quinone derivative, a metal oxide, or a cyano-containing compound.

The organic layer may include an electron transport layer, and the electron transport layer may include an electron transport organic compound and a metal complex.

The organic layer may be formed using a wet method using the vinylsilane compound.

According to another embodiment of the present invention, a flat panel display device may include the organic light-emitting device, where the first electrode of the organic light-emitting device may be electrically connected to a source electrode or a drain electrode of a thin film transistor.

BRIEF DESCRIPTION OF THE DRAWINGS

The above and other features and advantages of the present invention will become more apparent by reference to the following detailed description when considered in conjunction with the attached drawing in which:

FIG. 1 is a schematic view of an organic light-emitting device according to an embodiment of the present invention.

DETAILED DESCRIPTION OF THE INVENTION

As used herein, the term "and/or" includes any and all combinations of one or more of the associated listed items. Expressions such as "at least one of," when preceding a list of elements, modify the entire list of elements and do not modify the individual elements of the list.

Anthracene derivatives are known as materials for an organic emission layer. For example, an organic light-emitting device manufactured using a phenylanthracene dimer or trimer is known. However, such organic light-emitting devices have narrow energy gaps and lower blue-light color purity since two or three oligomeric species of anthracene are linked by conjugation.

In addition, such compounds are highly vulnerable to oxidation and thus are liable to produce impurities, necessitating purification. In order to overcome these drawbacks, organic light-emitting devices manufactured using anthracene compounds, including naphthalene substituted for anthracene at the 1 and 9 positions, or using a diphenylanthracene compound including an aryl group substituted for a phenyl group at the m-position have been introduced. However, these organic light-emitting devices have lower light-emission efficiency.

Organic light-emitting devices may also be manufactured using naphthalene-substituted monoanthracene derivatives. However, the light-emission efficiency thereof is low at about 1 cd/A, and thus, such organic light-emitting devices are not suitable for practical use. Furthermore, organic light-emitting devices may be manufactured using phenylanthracene compounds including aryl substituents at the m-position. Such compounds have good thermal resistance but lead to unsatisfactorily low light-emission efficiency of about 2 cd/A.

In addition, it has been reported that a light-emitting material may be doped in order to increase the light-emission efficiency of an emission layer (EML), in which case, the above-described anthracene-based compound is used as a host, and a styryl compound or a distyryl compound is used as a dopant. When a blue fluorescent dopant in which an arylamine group is added to a terminal of a styryl compound, the light-emission efficiency of the EML is increased. However, light emitted from most of these light-emitting materials is bluish green instead of deep blue in terms of the color purity of the emitted blue light. In addition, when these light-emitting materials are used in an organic light-emitting device, most organic light-emitting devices do not have sufficiently long half-lives and thus are not commercially viable.

The present invention will now be described more fully with reference to the accompanying drawings, in which exemplary embodiments of the invention are shown.

In some embodiments of the present invention, a vinylsilane compound is represented by Formula 1 below.

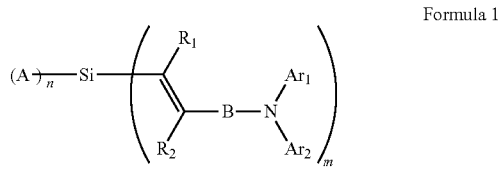

Formula 1

In Formula 1 above, each A may be independently a substituted or unsubstituted $C_1$-$C_{60}$ alkyl group, a substituted or unsubstituted $C_1$-$C_{60}$ alkoxy group, a substituted or unsubstituted $C_5$-$C_{60}$ aryl group, or a substituted or unsubstituted $C_3$-$C_{60}$ heteroaryl group. Each of $R_1$ and $R_2$ may be independently a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_5$-$C_{60}$ aryl group, or a substituted or unsubstituted $C_3$-$C_{60}$ heteroaryl group. B may be a bivalent linker and may be a substituted or unsubstituted $C_1$-$C_{60}$ alkylene group, a substituted or unsubstituted $C_5$-$C_{60}$ arylene group, or a substituted or unsubstituted $C_3$-$C_{60}$ heteroarylene group. Each of $Ar_1$ and $Ar_2$ may be independently a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group. $Ar_1$ and $Ar_2$ may optionally be linked to form a ring, n may be an integer from 0 to 3, m may be an integer from 1 to 4, and n+m=4.

The above-described compound according to an embodiment of the present invention can be used as a light-emitting material, a hole transport material, or a hole injection material for an organic light-emitting device. The compounds containing vinylsilane in their molecular structure, such as the above-described compounds, have increased light-emission efficiency by virtue of the introduction of an amine group in the molecular structure. In addition, when the compounds are used as a blue fluorescent dopant, blue light with high purity may be obtained. The compounds have reinforced hole transport capability and thus may be used as a hole injection material or a hole transport material. Various substituents may be introduced in the molecule, thereby improving thermal properties (Tg, Tm). In addition, the state of the membrane that is in a film state is improved, thereby increasing resistance to high temperature atmospheres, and improving heat resistance with respect to Joule's heat generated between organic layers and between an organic layer and a metal electrode. In addition, an organic-light emitting device manufactured using the above-described vinylsilane compound has high durability during storage and driving.

Substituents of the above-described compound will be described in more detail.

According to an embodiment of the present invention, in Formula 1 above, each A may be independently a substituted or unsubstituted $C_1$-$C_{30}$ alkyl group, a substituted or unsubstituted $C_5$-$C_{30}$ aryl group, or a substituted or unsubstituted $C_3$-$C_{30}$ heteroaryl group. Each of $R_1$ and $R_2$ may be independently a hydrogen atom, a deuterium atom, a substituted or unsubstituted $C_1$-$C_{30}$ alkyl group, a substituted or unsubstituted $C_3$-$C_{30}$ cycloalkyl group, a substituted or unsubstituted $C_5$-$C_{30}$ aryl group, or a substituted or unsubstituted $C_3$-$C_{30}$ heteroaryl group. B may be a bivalent linker and may be a substituted or unsubstituted $C_5$-$C_{30}$ arylene group or a substituted or unsubstituted $C_3$-$C_{30}$ heteroarylene group. Each of $Ar_1$ and $Ar_2$ may be independently a substituted or unsubstituted $C_5$-$C_{30}$ aryl group, a substituted or unsubstituted $C_3$-$C_{30}$ 3 heteroaryl group, or a substituted or unsubstituted $C_6$-$C_{30}$ condensed polycyclic group.

According to an embodiment of the present invention, in Formula 1 above, each of $R_1$ and $R_2$ may be independently a hydrogen atom or a deuterium atom.

According to another embodiment of the present invention, in Formula 1 above, each A may be independently any one of a hydrogen atom, a deuterium atom, a halogen atom, a cyano group, a substituted or unsubstituted $C_1$-$C_{20}$ alkyl group, or one of the compounds represented by Formulae 2a through 2d below:

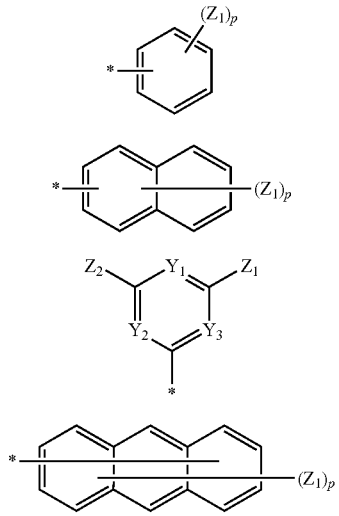

In Formulae 2a through 2d above, each of $Y_1$, $Y_2$, and $Y_3$ may be independently a linker represented by —N═, —N($R_{20}$)—, or —C($R_{21}$)═. Each of $Z_1$, $Z_2$, $R_{20}$, and $R_{21}$ may be independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group. p may be an integer from 1 to 12. * indicates a binding site.

In some embodiments, in Formula 1 above, each of $Ar_1$ and $Ar_2$ may be independently any one of the compounds represented by Formulae 3a through 3f below:

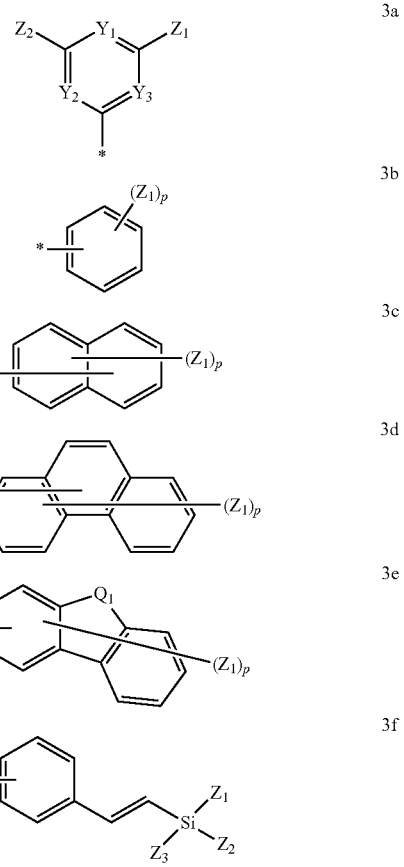

In Formulae 3a through 3f above, $Q_1$ may be a linker represented by —C($R_{30}$)($R_{31}$)—, —N($R_{32}$)—, —S—, or —O—. Each of $Y_1$, $Y_2$, and $Y_3$ may be independently a linker represented by —O—, —N═, —N($R_{20}$)—, or —C($R_{21}$)═. Each of $Z_1$, $Z_2$, $Z_3$, $R_{20}$, $R_{21}$, $R_{30}$, $R_{31}$, and $R_{32}$ may be independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group. p may be an integer from 1 to 12. r may be an integer from 0 to 5. * indicates a binding site.

According to another embodiment of the present invention, in Formula 1 above, B may be a linker represented by one of Formulae 4a through 4i, or may be a linker obtained by linking at least two of the compounds represented by Formulae 4a through 4i:

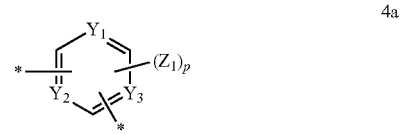

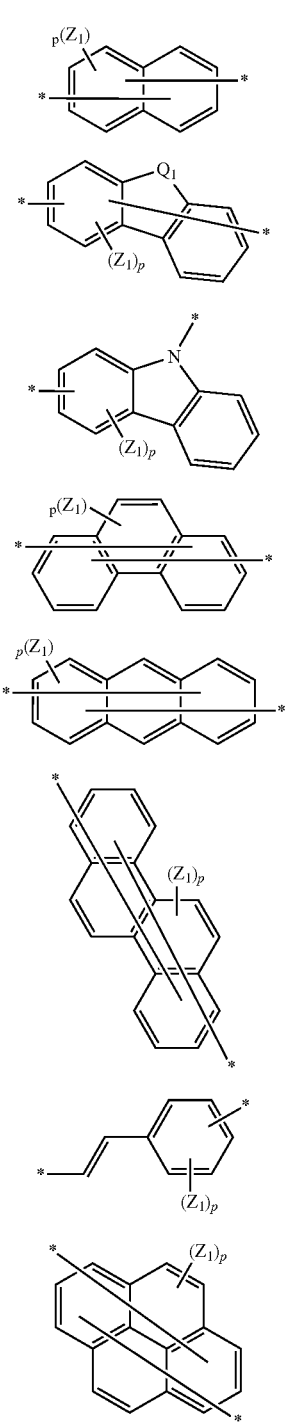

In Formulae 4a through 4i above, $Q_1$ may be a linker represented by $-C(R_{30})(R_{31})-$, $-N(R_{32})-$, $-S-$, or $-O-$. Each of $Y_1$, $Y_2$, and $Y_3$ may be independently a linker represented by $-O-$, $-N=$, $-N(R_{20})-$, or $-C(R_{21})=$. Each of $Z_1$, $R_{20}$, $R_{21}$, $R_{30}$, $R_{31}$, and $R_{32}$ may be independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group. p may be an integer from 1 to 12. * indicates a binding site.

Hereinafter, the substituents described throughout this specification will now be described in detail. In this regard, the numbers of carbons in the substituents are presented only for illustrative purposes and do not limit the characteristics of the substituents.

The unsubstituted $C_1$-$C_{60}$ alkyl group may be linear or branched. Examples of the alkyl group include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. Examples of the substituted $C_1$-$C_{60}$ alkyl group include any of the unsubstituted $C_1$-$C_{60}$ alkyl groups in which at least one hydrogen atom is substituted with a heavy hydrogen atom, a halogen atom, a hydroxyl group, a nitro group, a cyano group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group indicates an unsaturated alkyl group having at least one carbon-carbon double bond in the center or at a terminal of the alkyl group. Examples of the alkenyl group include, bur are not limited to, an ethenyl group, a propenyl group, a butenyl group, and the like. Examples of the substituted $C_2$-$C_{60}$ alkenyl group include any of the unsubstituted $C_2$-$C_{60}$ alkenyl groups in which at least one hydrogen atom is substituted with one of the substituents described above with respect to the alkyl group.

The unsubstituted $C_2$-$C_{60}$ alkynyl group indicates an alkyl group having at least one carbon-carbon triple bond in the center or at a terminal of the alkyl group. Examples of the unsubstituted $C_2$-$C_{20}$ alkynyl group include, but are not limited to, acetylene, propylene, phenylacetylene, naphthylacetylene, isopropylacetylene, t-butylacetylene, diphenylacetylene, and the like. Examples of the substituted $C_2$-$C_{60}$ alkynyl group include any of the unsubstituted $C_2$-$C_{60}$ alkynyl groups in which at least one hydrogen atom in the alkynyl group is substituted with one of the substituents described above with respect to the alkyl group.

The unsubstituted $C_3$-$C_{60}$ cycloalkyl group indicates a $C_3$-$C_{60}$ cyclic alkyl group. The substituted $C_3$-$C_{60}$ cycloalkyl group is any of the unsubstituted $C_3$-$C_{60}$ cycloalkyl groups in which at least one hydrogen atom is substituted with one of the substituents described above with respect to the $C_1$-$C_{60}$ alkyl group.

The unsubstituted $C_1$-$C_{60}$ alkoxy group indicates a group having the structure $-OA$ where A is an unsubstituted $C_1$-$C_{60}$ alkyl group as described above. Nonlimiting examples of the unsubstituted $C_1$-$C_{60}$ alkoxy group include a methoxy group, an ethoxy group, a propoxy group, an isopropyloxy group, a butoxy group, and a pentoxy group. The substituted $C_1$-$C_{60}$ alkoxy group is any of the unsubstituted $C_1$-$C_{60}$ alkoxy groups in which at least one hydrogen atom is substituted with one of the substituents described above with respect to the alkyl group.

The unsubstituted $C_5$-$C_{60}$ aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. The substituted $C_5$-$C_{60}$ aryl group is any of the unsubstituted $C_5$-$C_{60}$ aryl groups in which at least one hydrogen atom is substituted with one of the substituents described above with respect to the unsubstituted $C_1$-$C_{60}$ alkyl group.

Examples of the substituted or unsubstituted $C_5$-$C_{60}$ aryl group include, but are not limited to, a phenyl group, a $C_1$-$C_{10}$ alkylphenyl group (for example, ethylphenyl group), a halophenyl group (for example, o-, m-, or p-fluorophenyl group, dichlorophenyl group), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, a o-, m-, and p-toryl group, an o-, m-, or p-cumenyl group, a mesityl group, a phenoxyphenyl group, a ($\alpha,\alpha$-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group.

The unsubstituted $C_3$-$C_{60}$ heteroaryl group includes an aryl group including one, two or three hetero atoms selected from N, O, P and S. At least two rings may be fused to each other or linked to each other by a single bond. Examples of the unsubstituted $C_4$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indolyl group, a quinolyl group, an isoquinolyl group, and a dibenzothiophene group. The substituted $C_3$-$C_{60}$ heteroaryl group is any of the unsubstituted $C_3$-$C_{60}$ heteroaryl groups in which at least one hydrogen atom is substituted with one of the substituents described above with respect to the unsubstituted $C_1$-$C_{60}$ alkyl group.

The unsubstituted $C_5$-$C_{60}$ aryloxy group is a group represented by —$OA_1$ where $A_1$ may be a $C_5$-$C_{60}$ aryl group. An example of the aryloxy group is a phenoxy group. The substituted $C_5$-$C_{60}$ aryloxy group is any of the unsubstituted $C_5$-$C_{60}$ aryloxy groups in which at least one hydrogen atom is substituted with one of the substituents described above with respect to the unsubstituted $C_1$-$C_{60}$ alkyl group.

The unsubstituted $C_5$-$C_{60}$ arylthio group is represented by —$SA_1$, where $A_1$ may be a $C_5$-$C_{60}$ aryl group. Nonlimiting examples of the arylthio group include a benzylthio group and a naphthylthio group. The substituted $C_5$-$C_{60}$ arylthio group is any of the unsubstituted $C_5$-$C_{60}$ arylthio groups in which at least one hydrogen atom is substituted with one of the substituents described above with respect to the unsubstituted $C_1$-$C_{60}$ alkyl group.

The unsubstituted $C_6$-$C_{60}$ condensed polycyclic group refers to a substituent including at least two rings including at least one aromatic ring and at least one non-aromatic ring that are fused to each other, or to a substituent that has an unsaturated group in a ring but does not have a conjugated structure. The $C_6$-$C_{60}$ condensed polycyclic group is distinct from the aryl group and heteroaryl group in that it has a non-aromatic component.

Nonlimiting examples of the vinylsilane compound represented by Formula 1 include Compounds 1 to 71 represented by the formulae listed below. However, the heterocyclic compound of Formula 1 are not limited to those compounds.

An organic light-emitting device according to an embodiment of the present invention includes a first electrode; a second electrode; and an organic layer between the first electrode and the second electrode, where the organic layer includes the vinylsilane compound.

The organic layer may include at least one of a hole injection layer (HIL), a hole transport layer (HTL), a functional layer (hereinafter, referred to as a H-functional layer) having both hole injection and hole transport capabilities, a buffer layer, an electron blocking layer (EBL), an emission layer (EML), a hole blocking layer (HBL), an electron transport layer (ETL), an electron injection layer (EIL), and a functional layer (hereinafter, referred to as an E-functional layer) having both electron transport and electron injection capabilities.

The term "organic layer," as used herein, refers to a single layer and/or a plurality of layers between the first electrode and the second electrode of the organic light-emitting device.

The organic layer may include an EML, and the EML may include the vinylsilane compound. Alternatively, the organic layer may include at least one of a HIL, a HTL, and a H-functional layer having both hole injection and hole transport capabilities, and at least one of the HIL, the HTL, and the H-functional layer may include the vinylsilane compound.

The vinylsilane included in the EML may serve as a fluorescent dopant. For example, the vinylsilane compound may serve as a blue fluorescent dopant for emitting blue light. Alternatively, the vinylsilane included in the EML may serve as a fluorescent or phosphorescent dopant for emitting red light, green light, or blue light.

FIG. 1 is a schematic view of an organic light-emitting device according to an embodiment of the present invention. The structure of the organic light-emitting device and a method of manufacturing the same will be described with reference to FIG. 1.

The substrate (not shown) may be any substrate that is commonly used in organic light-emitting devices, and may include, for example, a glass substrate or a transparent plastic substrate with good mechanical strength, thermal stability, transparency, surface smoothness, ease of handling, and water resistance.

The first electrode may be formed by applying a first electrode material onto the substrate by vapor deposition or sputtering. When the first electrode is an anode, the first electrode material may be selected from materials with high work functions such that holes may be easily injected to the first electrode. The first electrode may be a reflective electrode or a transparent electrode. Examples of the first electrode material may include materials such as indium tin oxide (ITO), indium zinc oxide (IZO), tin oxide ($SnO_2$), and zinc oxide (ZnO), which are transparent and have good conductivity. In addition, the first electrode material may be magnesium (Mg), aluminum (Al), aluminum-lithium (Al—Li), calcium (Ca), magnesium-indium (Mg—In), magnesium-silver (Mg—

Ag), or the like, and when these materials are used, the first electrode may be a reflective electrode.

The first electrode may have a single layer or a multilayered structure including two or more layers. For example, the first electrode may have, but is not limited to, a three-layered structure of ITO/Ag/ITO.

An organic layer may be disposed on the first electrode.

The organic layer may include an HIL, a HTL, a buffer layer (not shown), an EML, an ETL, an EIL, or the like.

The HIL may be formed on the first electrode by any of a variety of methods, for example, by vacuum deposition, spin coating, casting, Langmuir-Blodgett (LB) deposition, or the like.

When the HIL is formed using vacuum deposition, the deposition conditions may vary according to the material used to form the HIL, and the structural and thermal characteristics of the HIL. For example, the deposition conditions may include, but are not limited to, a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, the coating conditions may vary according to the material used to form the HIL, and the structural and thermal properties of the HIL. For example, the coating conditions may include, but are not limited to, a coating speed of about 2,000 rpm to about 5,000 rpm, and a thermal treatment temperature of about 80° C. to about 200° C. at which temperature the solvent remaining after coating may be removed.

The HIL may be formed of any material that is commonly used to form a HIL. Non-limiting examples of the material that may be used to form the HIL include N,N'-diphenyl-N,N'-bis-[4-(phenyl-m-tolyl-amino)-phenyl]-biphenyl-4,4'-diamine (DNTPD), a phthalocyanine compound such as copperphthalocyanine, 4,4',4''-tris(3-methylphenylphenylamino)triphenylamine (m-MTDATA), N,N'-di(1-naphthyl)-N,N'-diphenylbenzidine (NPB), TDATA, 2-TNATA, polyaniline/Dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), or polyaniline/poly(4-styrenesulfonate) (PANI/PSS):

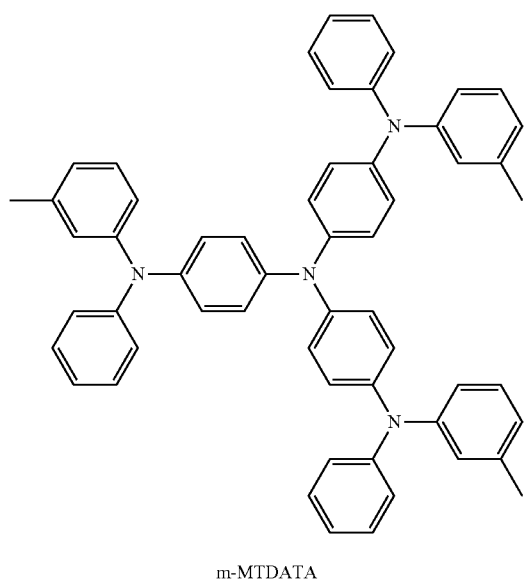

m-MTDATA

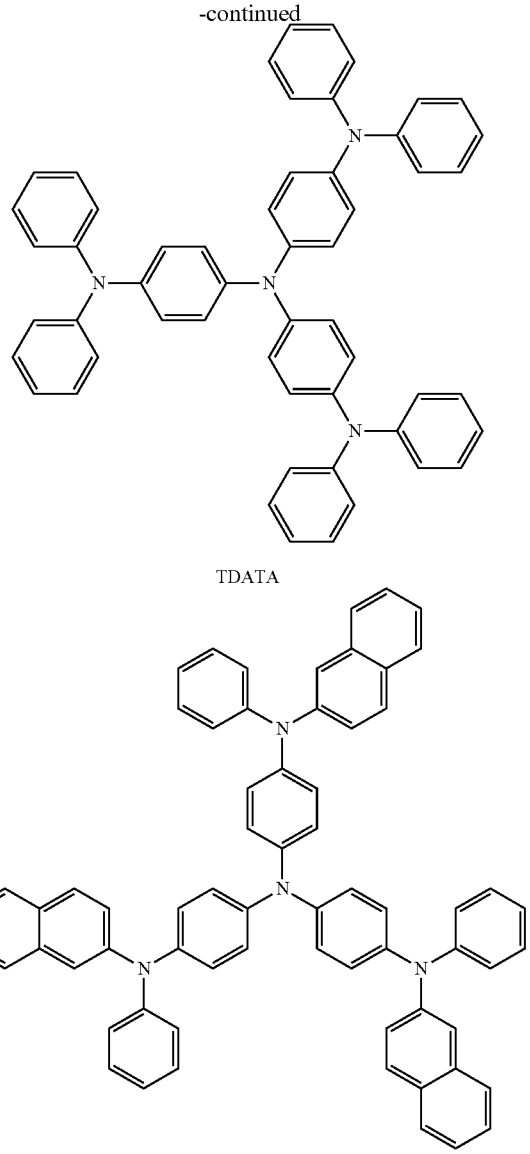

TDATA

2-TNATA

The HIL may have a thickness of about 100 Å to about 10000 Å, for example, about 100 Å to about 1000 Å. When the thickness of the HIL is within these ranges, the HIL may have good hole injection characteristics without substantially increasing driving voltage.

The HTL may be formed on the HIL using any of a variety of methods, for example, vacuum deposition, spin coating, casting, LB deposition, or the like. When the HTL is formed by vacuum deposition or spin coating, the deposition or coating conditions may be similar to those used to form the HIL, though the deposition or coating conditions may vary according to the material used to form the HTL.

The HTL may be formed of a vinylsilane compound according to an embodiment of the present invention or any material that is commonly used to form a HTL. Non-limiting examples of such HTL materials include N,N'-bis(3-methylphenyl)-N,N'-diphenyl-[1,1-biphenyl]-4,4'-diamine (TPD), 4,4',4''-tris(N-carbazolyl)triphenylamine (TCTA), N,N'-di(1-naphthyl)-N,N'-diphenylbenzidine) (NPB), or the like.

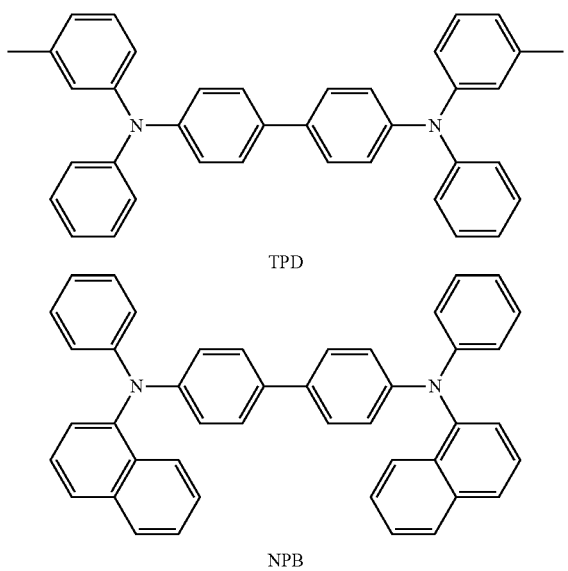

TPD

NPB

The HTL may have a thickness of about 50 Å to about 2000 Å, for example, about 100 Å to about 1500 Å. When the thickness of the HTL is within these ranges, the HTL may have good hole transport characteristics without substantially increasing driving voltage.

The H-functional layer (i.e., the layer having both hole injection and hole transport capabilities) may include at least one of the above described materials for forming the HIL and at least one of the materials for forming the HTL. The H-functional layer may have a thickness of about 500 Å to about 10000 Å, for example, about 100 Å to about 1000 Å. When the thickness of the H-functional layer is within these ranges, the H-functional layer may have good hole injection and transport characteristics without substantially increasing driving voltage.

In some embodiments, at least one of the HIL, the HTL, and the H-functional layer may include at least one compound represented by Formula 300 below and a compound represented by Formula 350 below:

Formula 300

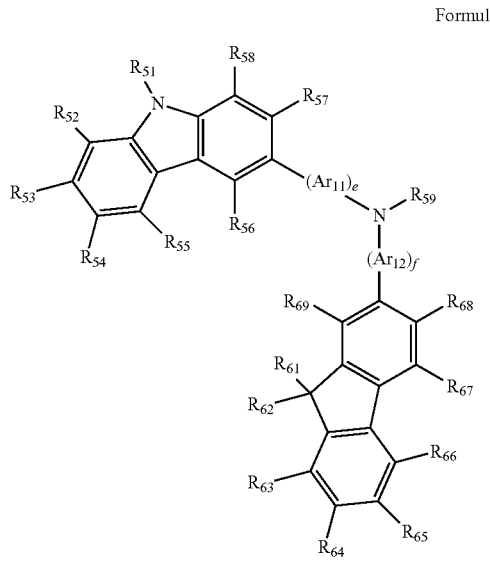

Formula 350

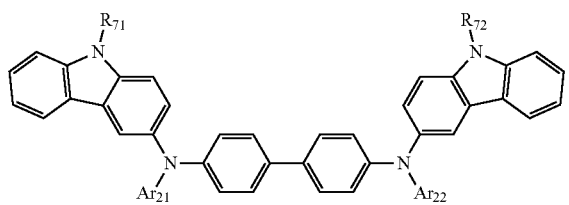

In Formulae 300 and 350 above, each of $Ar_{11}$, $Ar_{12}$, $Ar_{21}$, and $Ar_{22}$ may be independently a substituted or unsubstituted $C_5$-$C_{60}$ arylene group. $Ar_{11}$, $Ar_{12}$, $Ar_{21}$, and $Ar_{22}$ are the same as $Ar_1$ and $Ar_2$ defined above.

In Formula 300 above, each of e and f may be independently an integer from 0 to 5 or 0, 1, or 2. For example, e may be 1 and f may be 0, but the present invention is not limited thereto.

In formulae 300 and 350 above, each of $R_{51}$ through $R_{58}$, $R_{61}$ through $R_{69}$, $R_{71}$, and $R_{72}$ may be independently a hydrogen atom, a deuterium atom, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, each of $R_{51}$ through $R_{58}$, $R_{61}$ through $R_{69}$, $R_{71}$, and $R_{72}$ may be independently, but are not limited to, any one of a hydrogen atom; a deuterium atom; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group or $C_1$-$C_{10}$ alkoxy group substituted with at least one of a deuterium atom, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof; a phenyl group; a naphthyl group; an anthryl group; a fluorenyl group; a pyrenyl group; or a phenyl group, a naphthyl group, an anthryl group, a fluorenyl group, or a pyrenyl group substituted with at least one of a deuterium atom, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, or a $C_1$-$C_{10}$ alkoxy group.

In Formula 300 above, $R_{59}$ may be any one of a phenyl group; a naphthyl group; an anthryl group; a biphenyl group; a pyridinyl group; or a phenyl group, a naphthyl group, an anthryl group, a biphenyl group, or a pyridinyl group substituted with at least one of a deuterium atom, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a substituted or unsubstituted $C_1$-$C_{20}$ alkyl group, or a substituted or unsubstituted $C_1$-$C_{20}$ alkoxy group.

According to an embodiment of the present invention, a compound represented by Formula 300 above may be represented by, but is not limited to, Formula 300A below:

Formula 300A

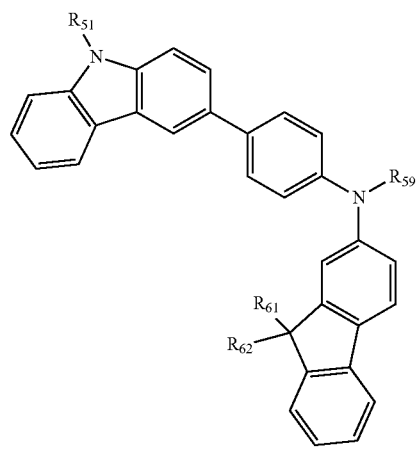

In Formula 300A above, $R_{51}$, $R_{60}$, $R_{61}$, and $R_{59}$ are as described above. For example, at least one of the HIL, the HTL, and the H-functional layer may include, but is not limited to, at least one of Compounds 301 through 320 below:

301

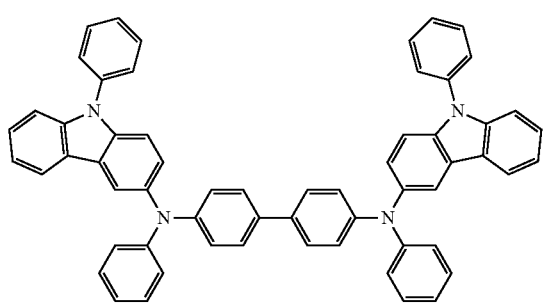

302

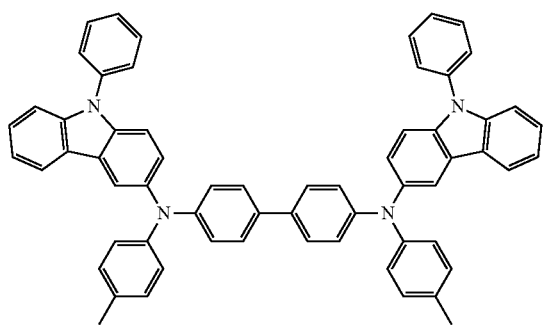

303

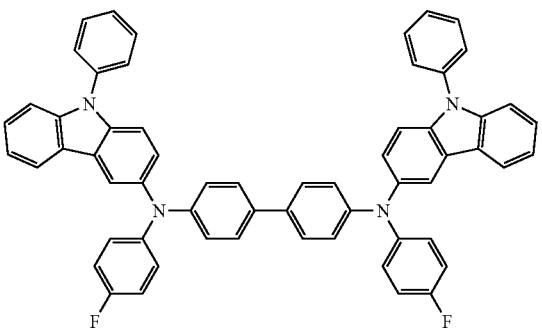

304

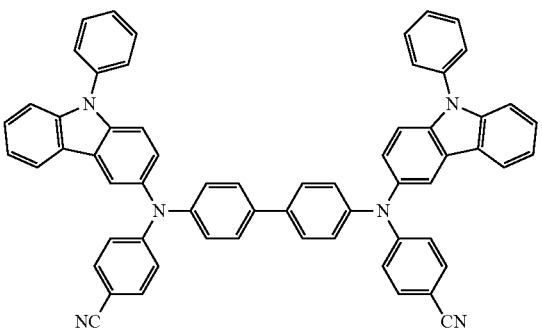

305

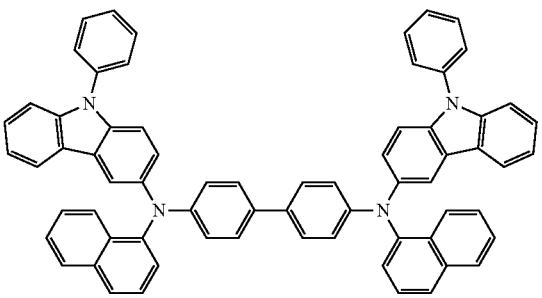

306

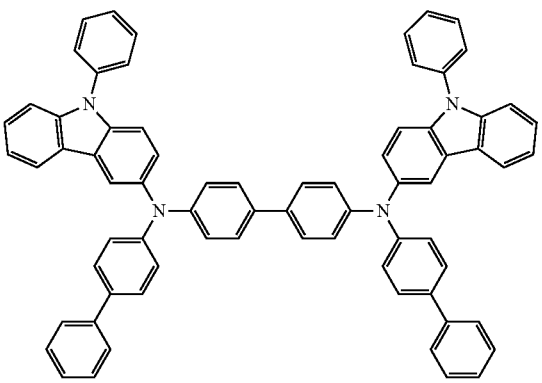

307
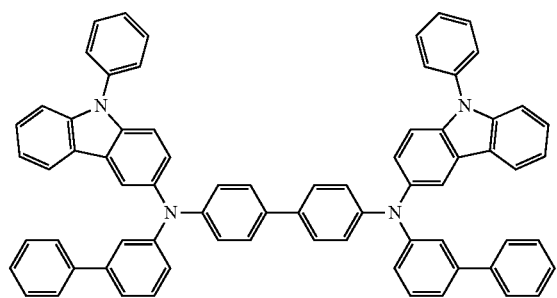
308
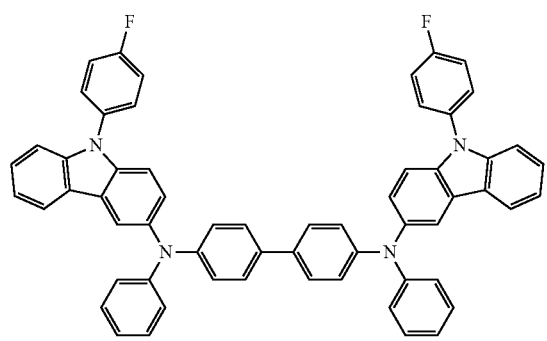
309
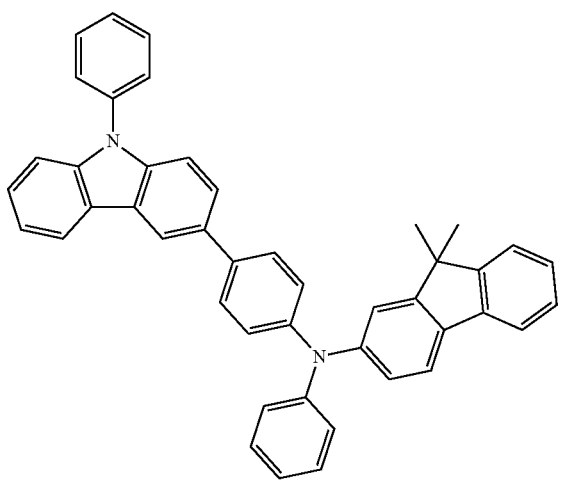
310
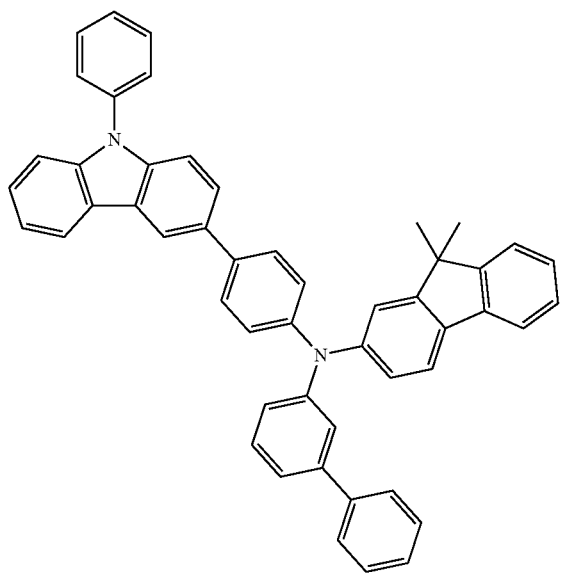
311
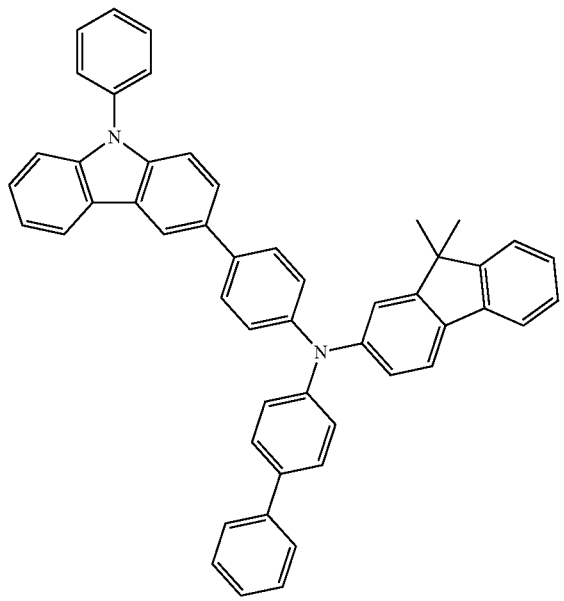

-continued
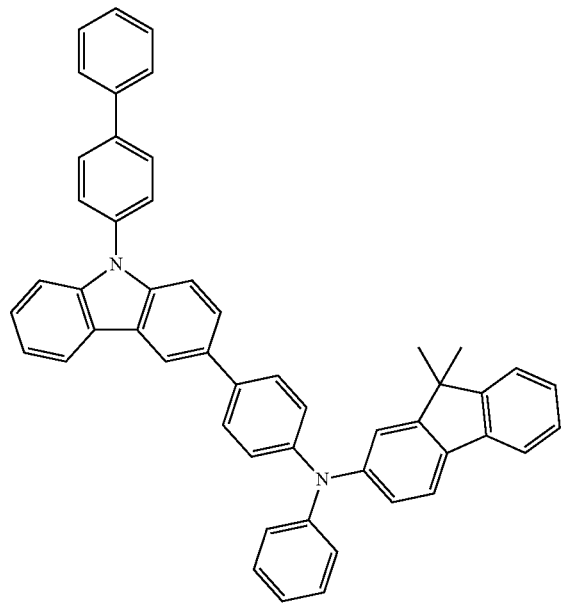
312
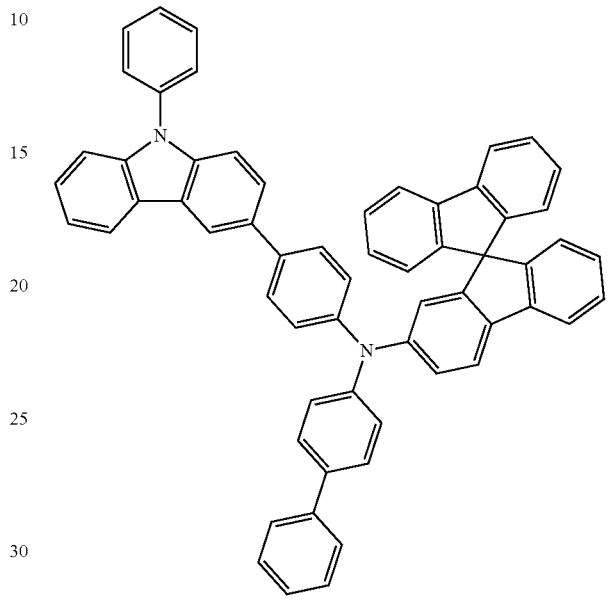
314
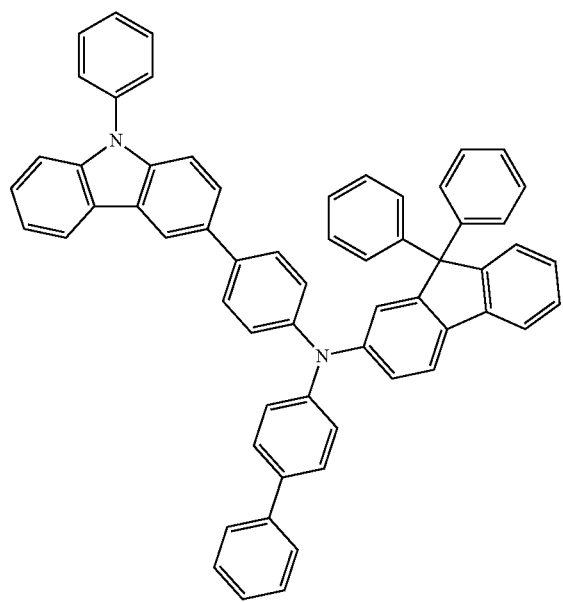
313
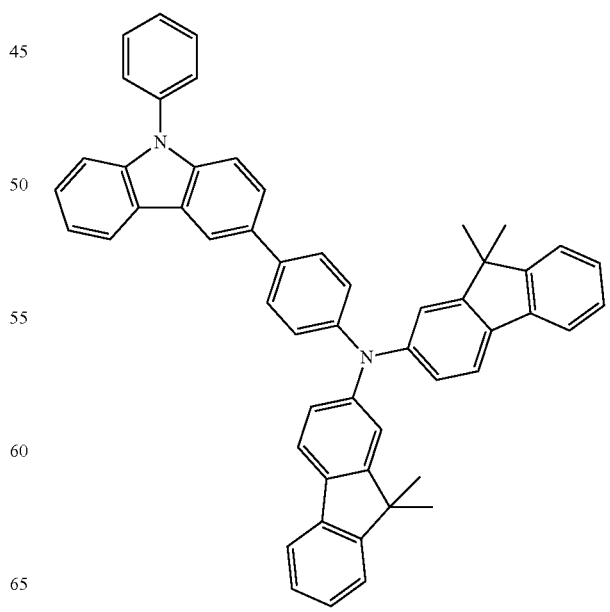
315

316

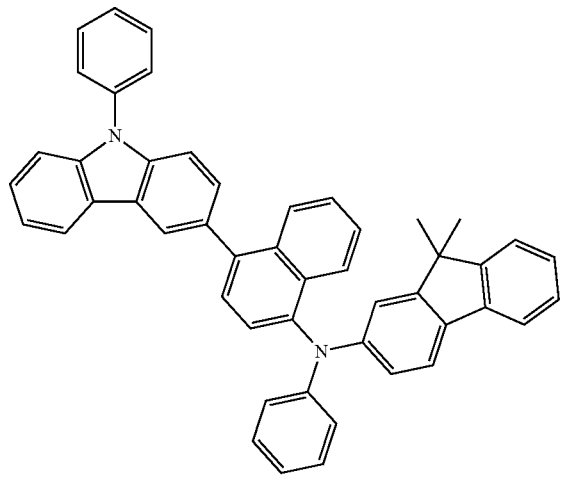

317

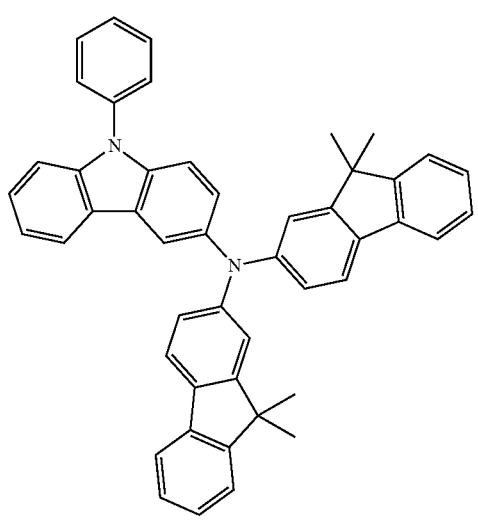

318

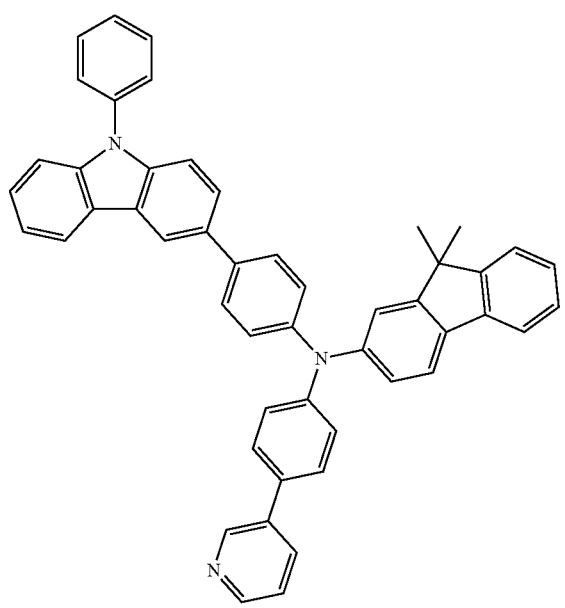

319

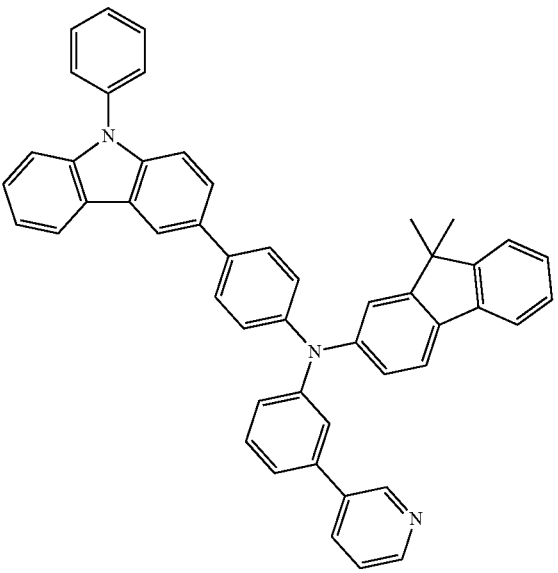

320

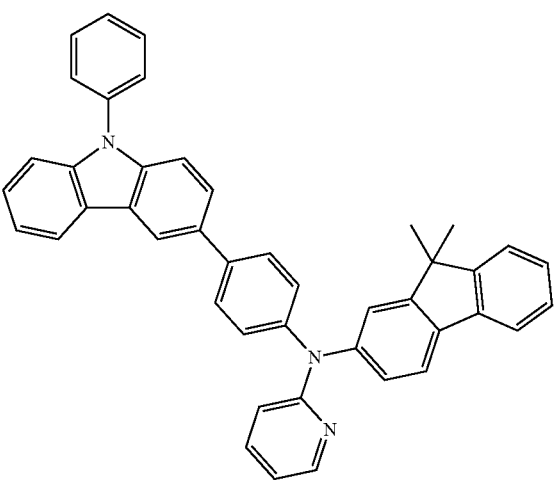

At least one of the hole injection layer, the hole transport layer, and the H-functional layer may further include a charge generating material for improved layer conductivity, in addition to the known hole injection material, the known hole transport material, and/or the material having both hole injection and hole transport capabilities.

The charge generating material may include, for example, a p-dopant. The p-dopant may include, but is not limited to, any one of quinone derivatives, a metal oxide; and cyano-containing compounds. Non-limiting examples of the p-dopant include quinone derivatives such as tetracyano-quinonedimethane (TCNQ), 2,3,5,6-tetrafluoro-tetracyano-1,4-benzoquinonedimethane (F4-CTNQ), and the like; metal oxides such as tungsten oxide, molybdenum oxide, and the like; and cyano-containing compounds such as Compound 200 below.

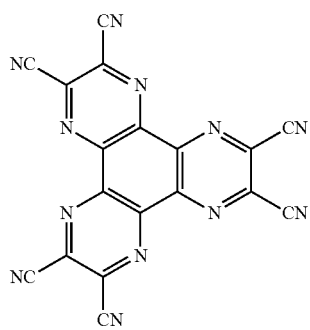

Compound 200

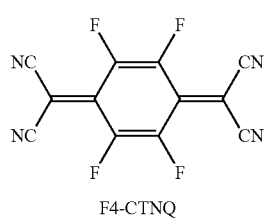

F4-CTNQ

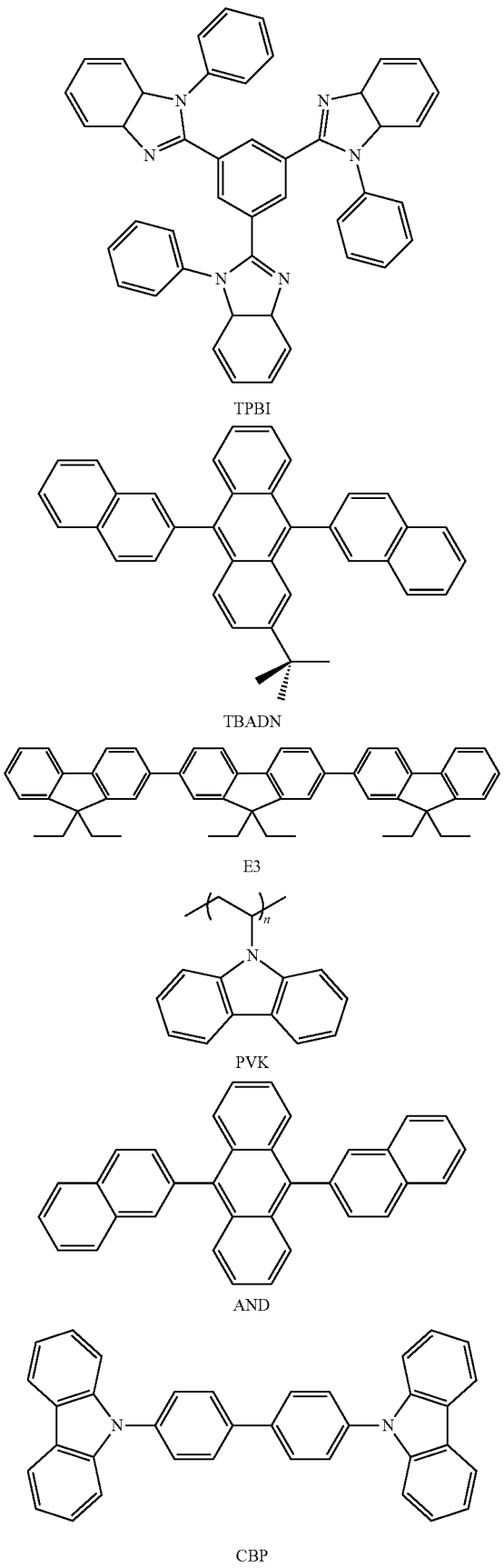

When the HIL, the HTL, or the H-functional layer further includes the charge generating material, the charge generating material may be, but is not limited to being, homogeneously dispersed or nonhomogeneously distributed in the layer.

A buffer layer may be disposed between at least one of the hole injection layer, the hole transport layer, and the H-functional layer and the EML. The buffer layer may compensate for the optical resonance distance according to the wavelength of light emitted from the EML, thereby increasing light-emission efficiency. The buffer layer may include any known hole injection material or any known hole transport material. Alternatively, the buffer layer may include the same material as any one of the HIL, the HTL, and the H-functional layer, which are formed below the buffer layer.

Then, an EML may be formed on the HTL, the H-functional layer, or the buffer layer by vacuum deposition, spin coating, casting, Langmuir-Blodgett (LB) deposition, or the like. When the EML is formed by vacuum deposition or spin coating, the deposition or coating conditions may vary according to the material used to form the EML, but may be similar to those used to form the HIL.

The EML may include a vinylsilane compound according to an embodiment of the present invention.

The EML may further include a host in addition to the vinylsilane compound.

Non-limiting examples of the host include $Alq_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, and distyrylarylene (DSA), dmCBP (refer to the following Formulae), and Compounds 501 through 509 below:

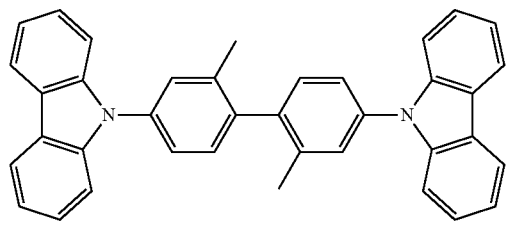
dmCBP
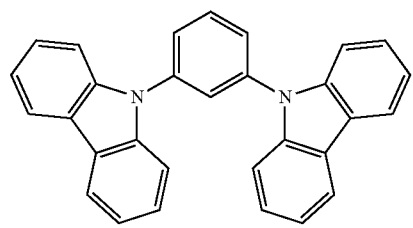
501
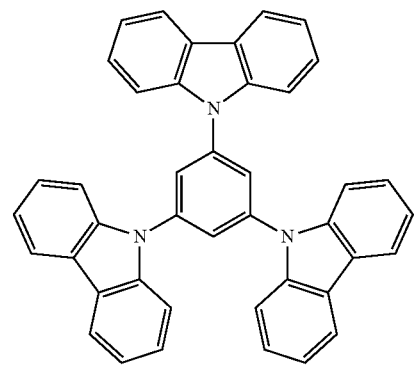
502
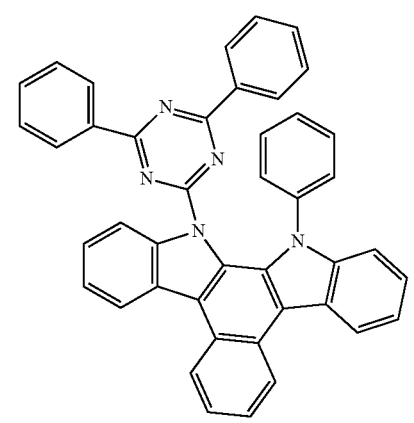
503
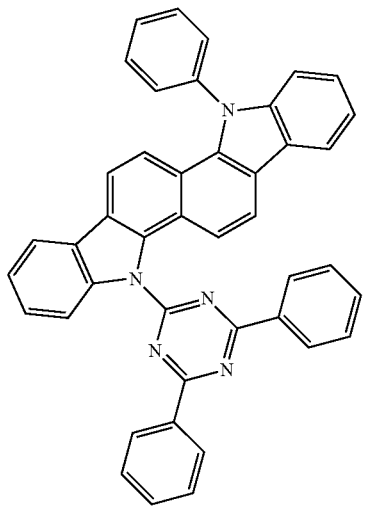
504
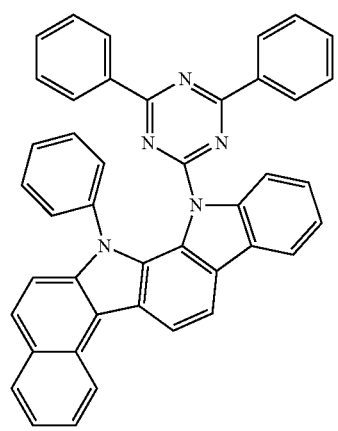
505
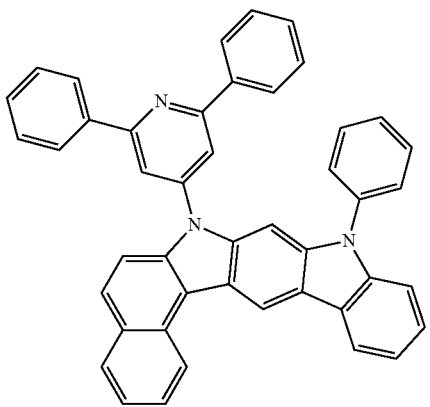
506

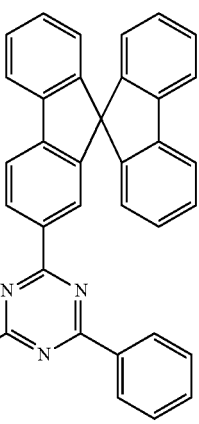

507

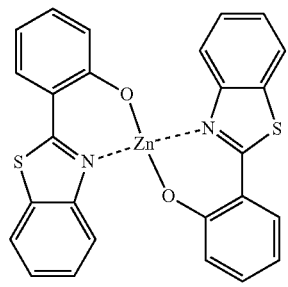

508

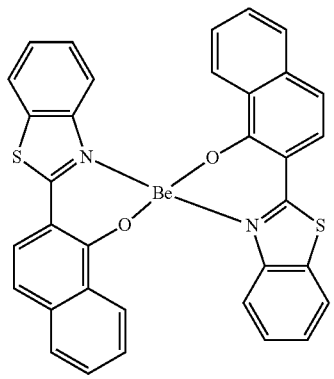

509

Alternatively, the host may be an anthracene-based compound represented by Formula 400 below:

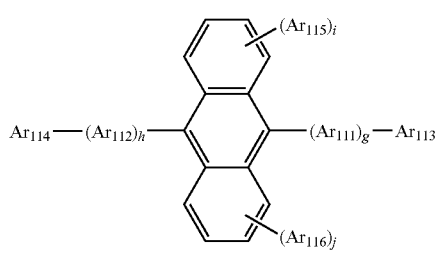

Formula 400

In Formula 400 above, each of $Ar_{111}$ and $Ar_{112}$ may be independently a substituted or unsubstituted $C_5$-$C_{60}$ arylene group. Each of $Ar_{113}$ through $Ar_{116}$ may be independently a substituted or unsubstituted $C_1$-$C_{10}$ alkyl group or a substituted or unsubstituted $C_5$-$C_{60}$ aryl group. Each of g, h, i, and j may be independently an integer from 0 to 4.

For example, in Formula 400 above, each of $Ar_{111}$ and $Ar_{112}$ may be independently, but are not limited to, a phenylene group, a naphthylene group, a phenanthrenylene group, or a pyrenylene group; or a phenylene group, a naphthylene group, a phenanthrenylene group, a fluorenylene group, or a pyrenylene group which is substituted with at least one of a phenyl group, a naphthyl group, or an anthryl group.

In Formula 400 above, each of g, h, i, and j may be independently 0, 1, or 2.

In Formula 400 above, each of $Ar_{113}$ through $Ar_{116}$ may be independently, but is not limited to, any one of a $C_1$-$C_{10}$ alkyl group substituted with at least one of a phenyl group, a naphthyl group, or an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, or a fluorenyl group substituted with at least one of a deuterium atom, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkyl group, a $C_1$-$C_{60}$ alkoxy group, a phenyl group, a naphthyl group, an anthryl group, a pyrenyl group, a phenanthrenyl group, or a fluorenyl group; or

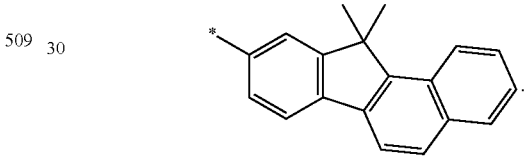

For example, an anthracene-based compound represented by Formula 400 above may be, but is not limited to, one of the Compounds below:

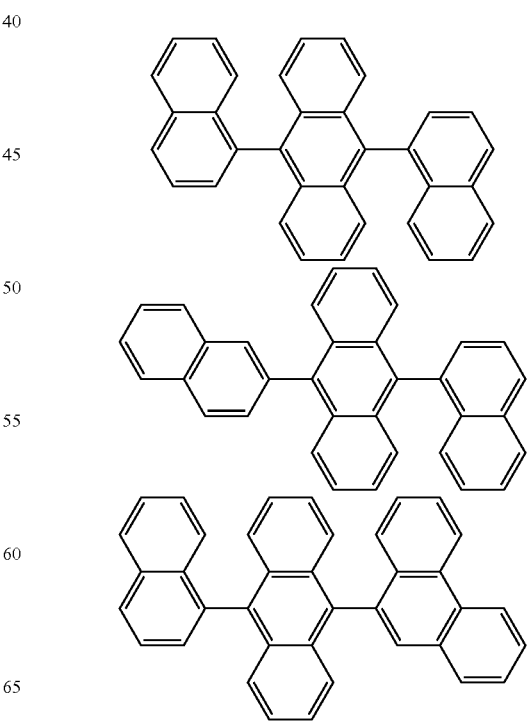

-continued
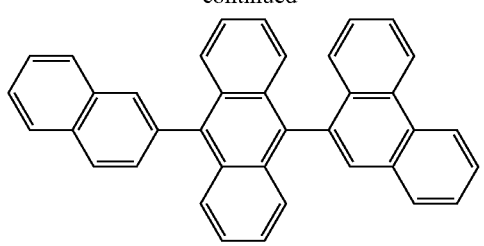
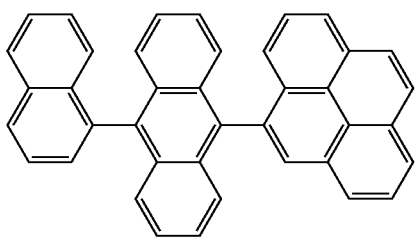
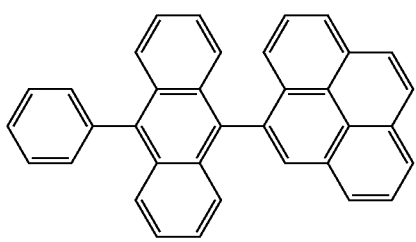
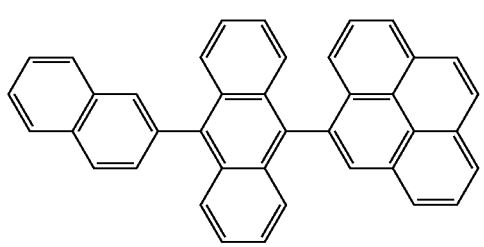
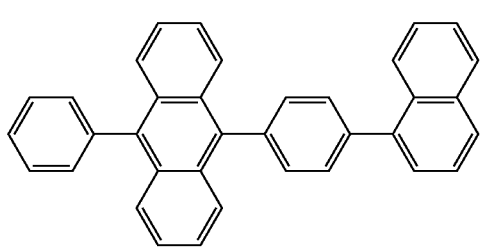
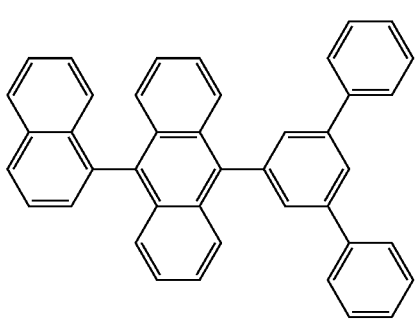
-continued
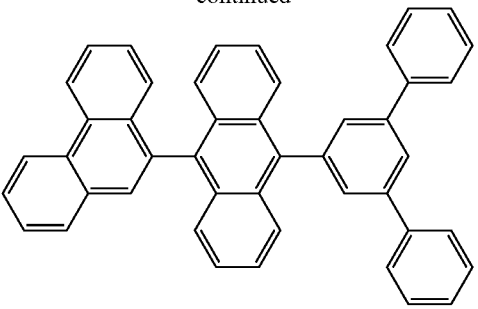
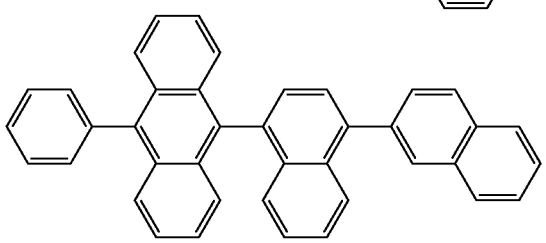
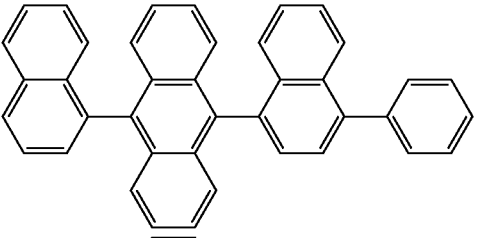
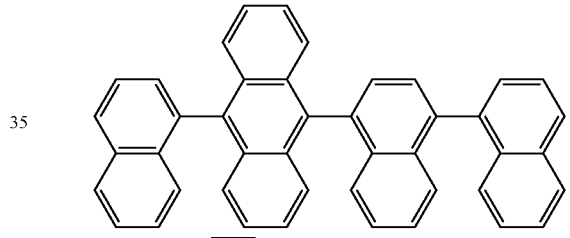
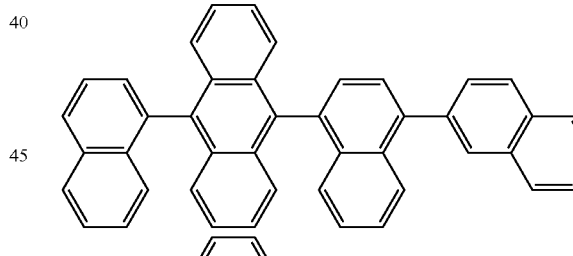
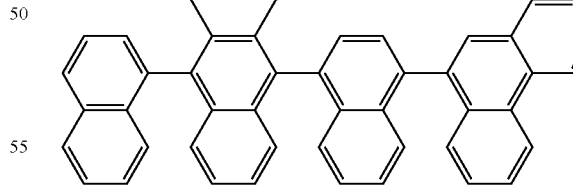
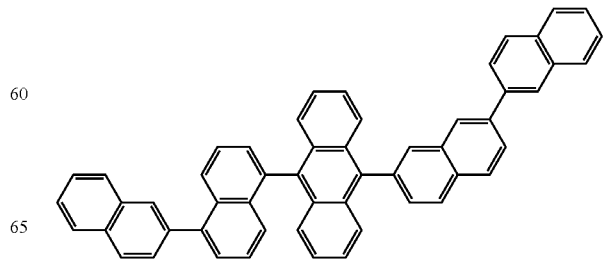

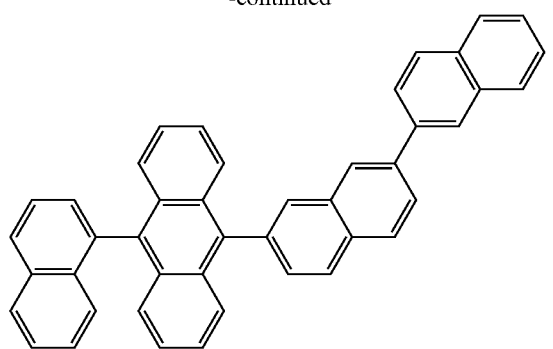
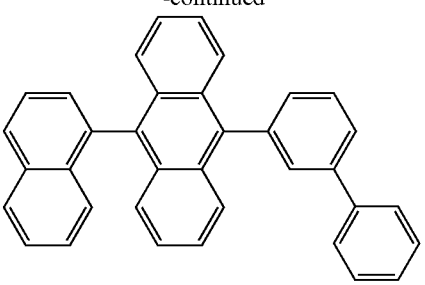
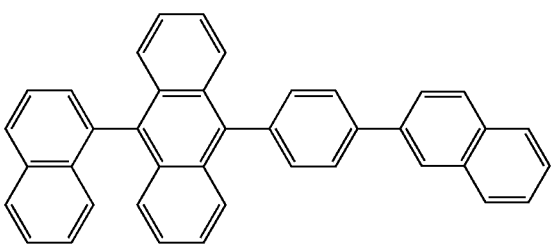
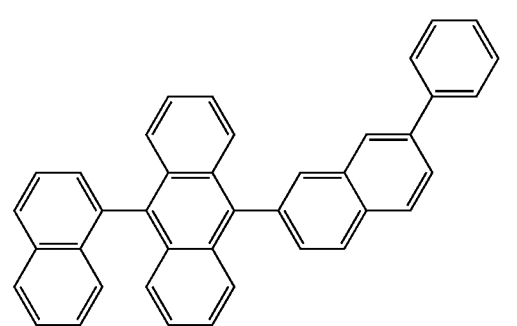 [SMILES: c1ccc(-c2ccc3ccc(-c4c5ccccc5c(-c5cccc6ccccc56)c5ccccc45)cc3c2)cc1]
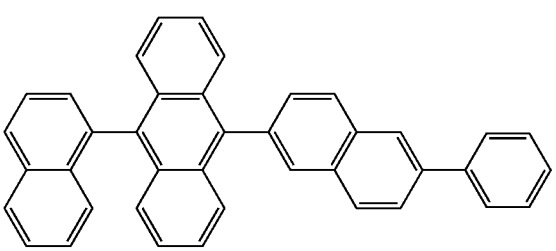
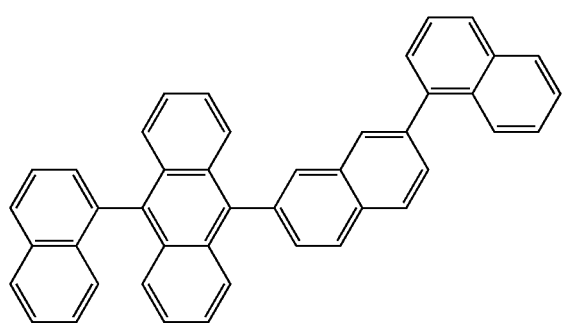
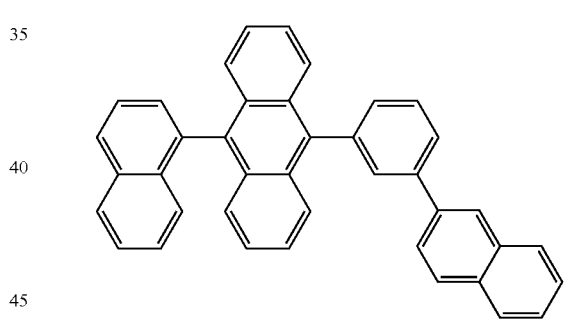
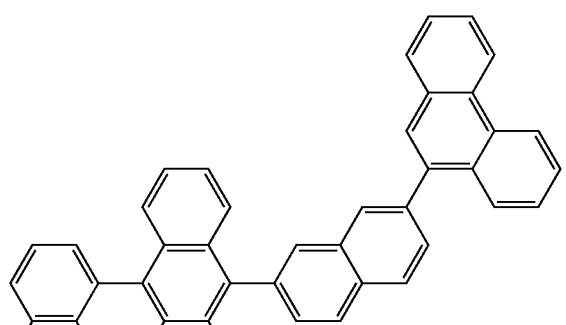
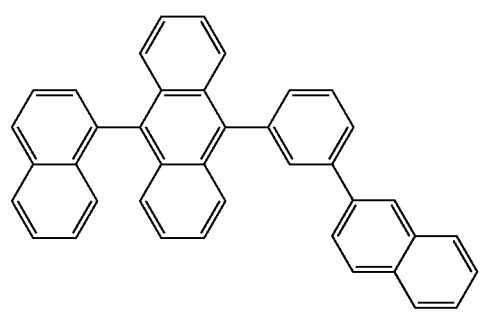
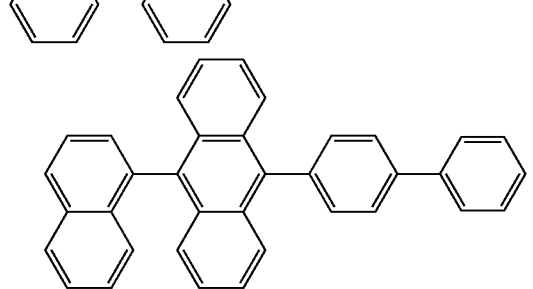
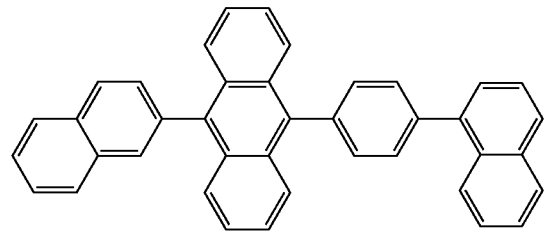

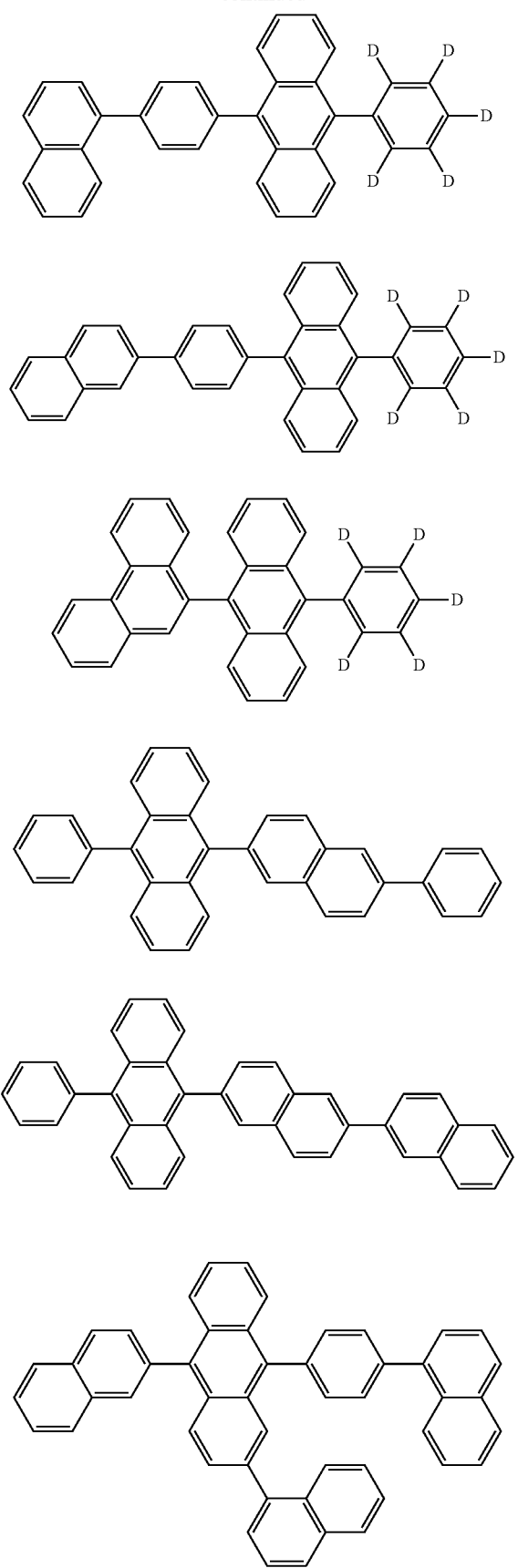
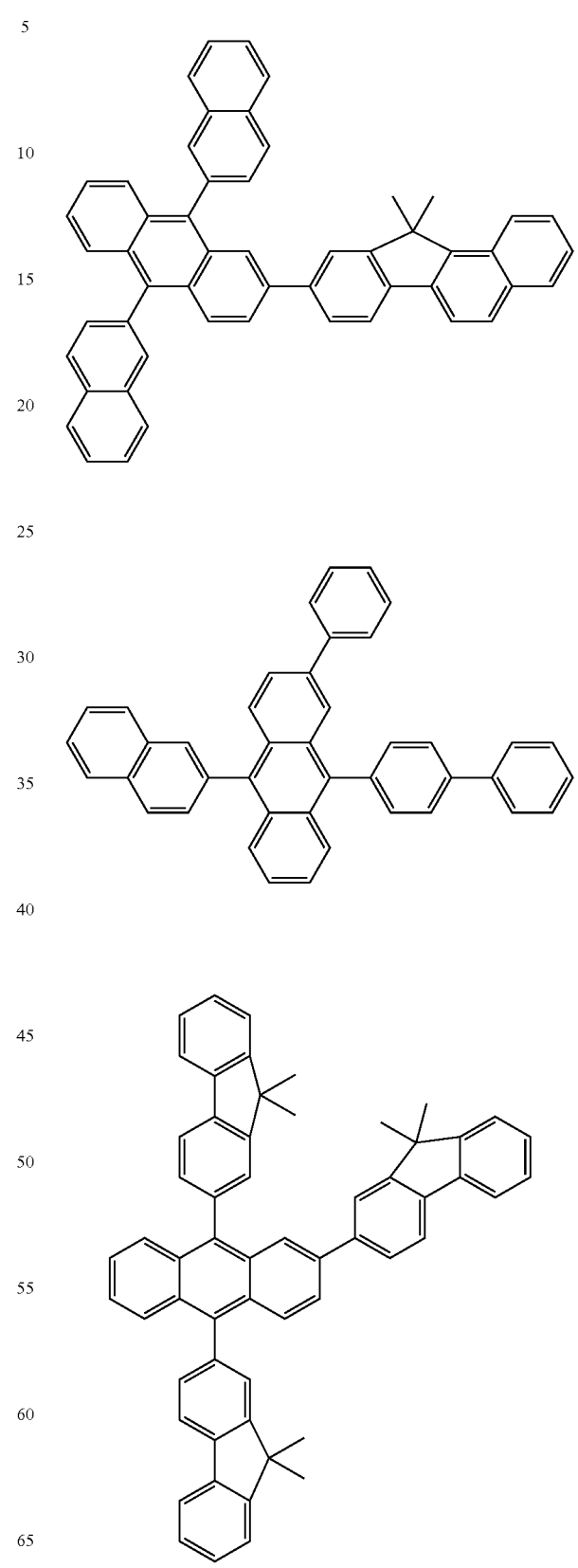

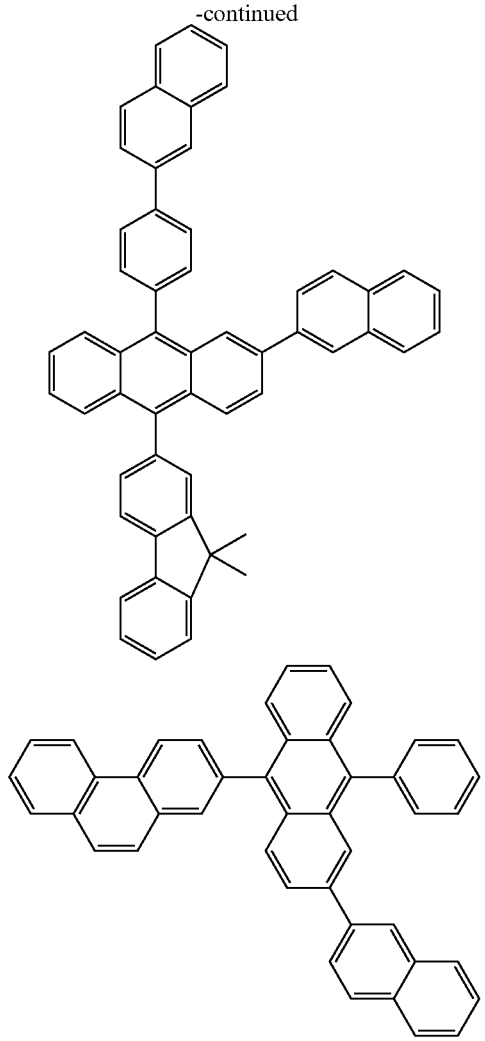

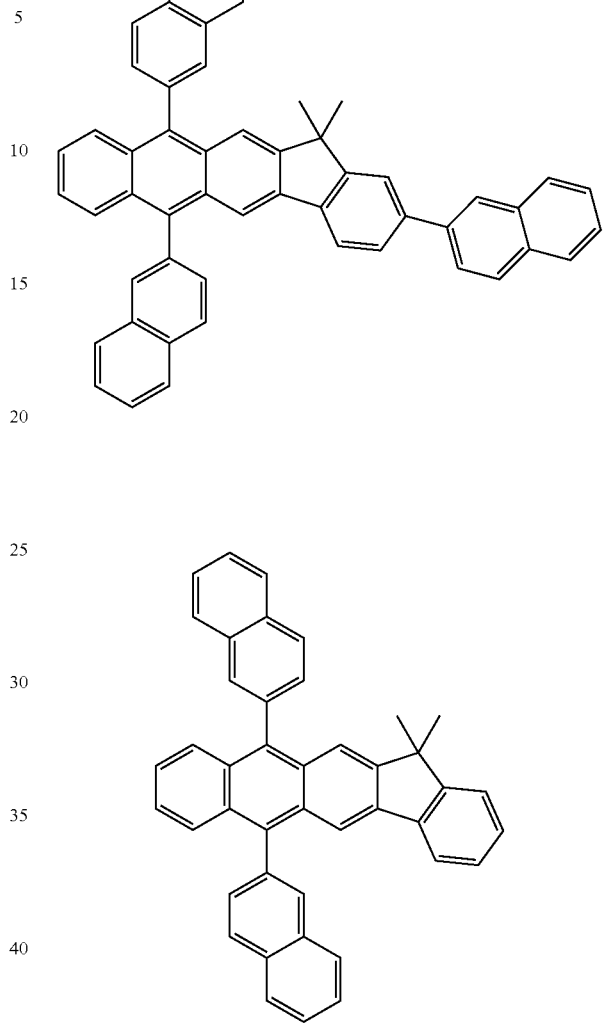

Alternatively, the host may be an anthracene-based compound represented by Formula 401 below:

Formula 401

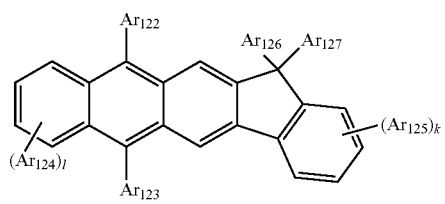

In Formula 401 above, $Ar_{122}$ through $Ar_{125}$ are the same as $Ar_{113}$ of Formula 400 defined above.

In Formula 401, each of $Ar_{126}$ and $Ar_{127}$ may be independently a $C_1$-$C_{10}$ alkyl group (for example, a methyl group, an ethyl group, or a propyl group).

In Formula 401 above, each of k and l may independently be an integer from 0 through 4. For example, each of k and l may be independently 0, 1, or 2.

For example, the anthracene-based compound represented by Formula 401 above may be, but is limited to, any one of the Compounds below:

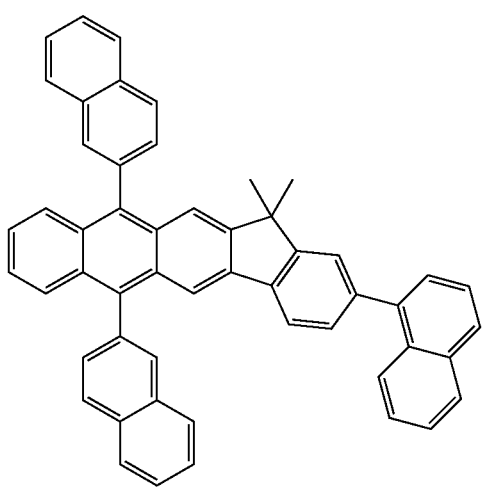

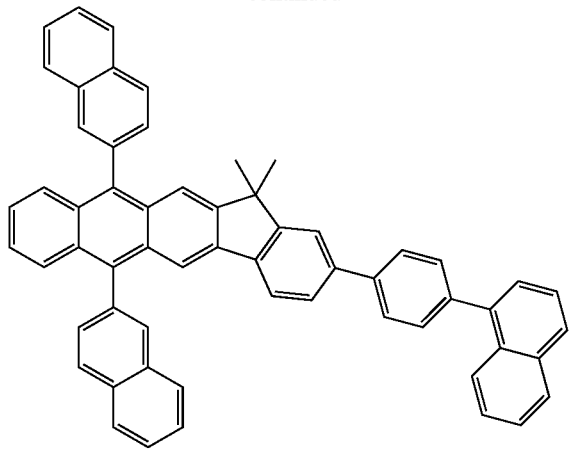 [SMILES: CC1(C)c2cc(-c3ccc(-c4cccc5ccccc45)cc3)ccc2-c2cc3c(-c4ccc5ccccc5c4)c4ccccc4c(-c4ccc5ccccc5c4)c3cc21]

When the organic light-emitting device is a full color organic light-emitting device, the EML may be patterned to include a red EML, a green EML, and a blue EML. In this case, the blue EML may include a vinylsilane compound as a blue fluorescent dopant, as described above.

At least one of the red fluorescent layer, the green fluorescent layer, and the blue fluorescent layer may include the dopants below (ppy=phenylpyridine).

Non-limiting examples of the blue dopant may include the compounds below:

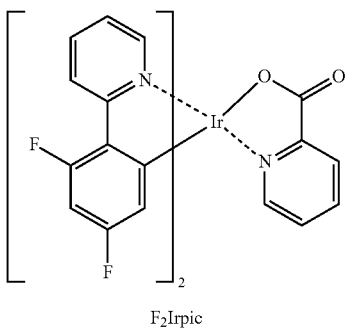
F₂Irpic

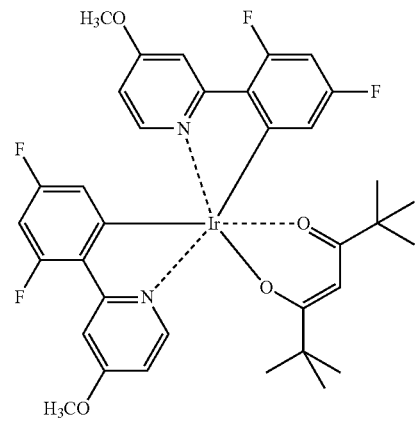
(F₂ppy)₂Ir(tmd)

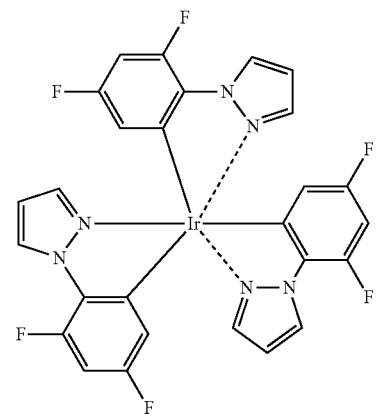
Ir(dfppz)₃

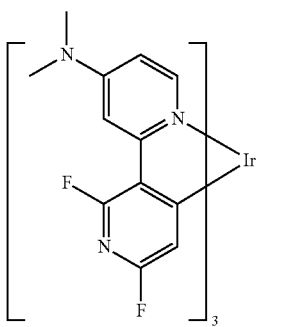

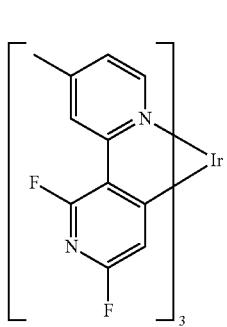

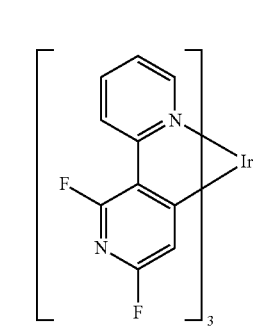

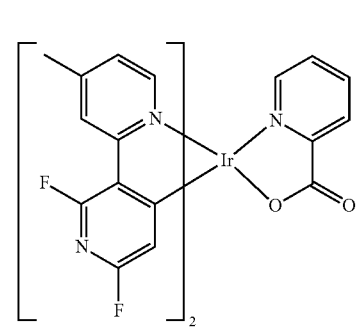

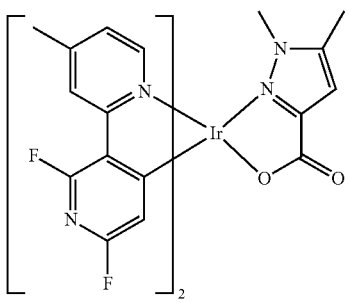

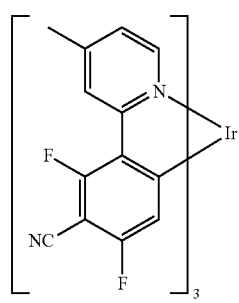

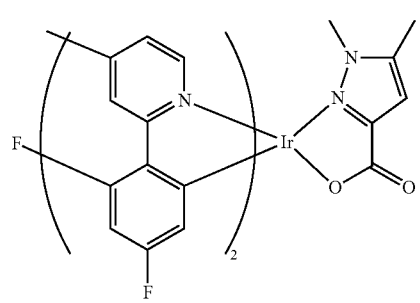

-continued
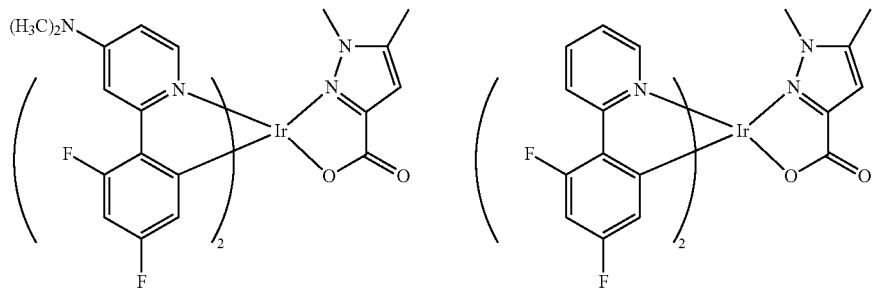
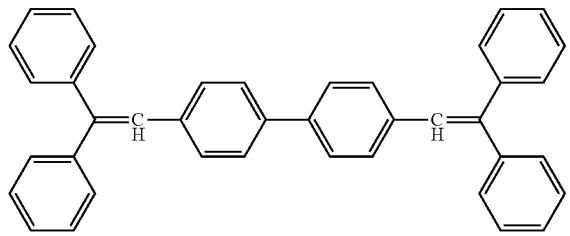
DPVBi
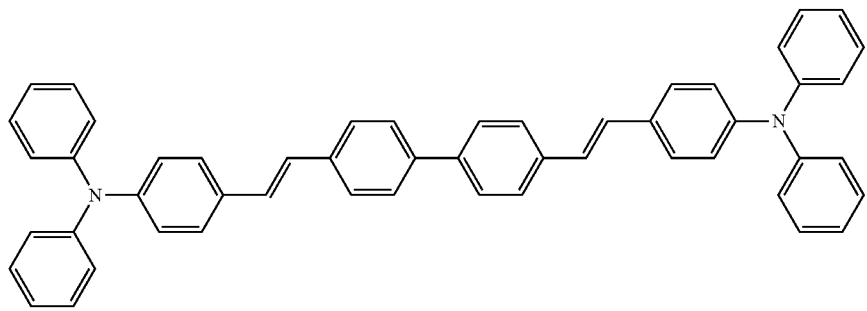
DPAVBi
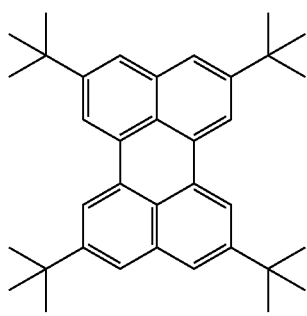
TBPe

Non-limiting examples of the blue dopant may include, but are limited to, the compounds below:
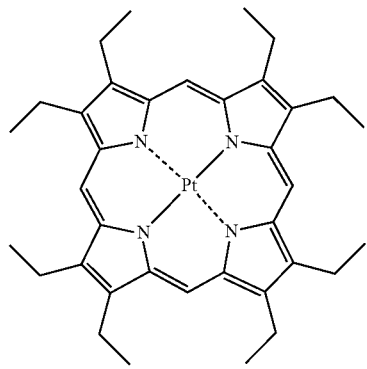
PtOEP
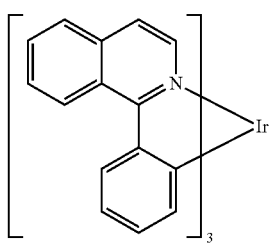
Ir(piq)₃
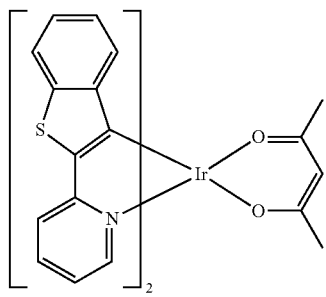
Btp₂Ir(acac)
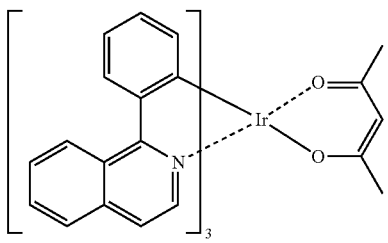
Ir(pq)₂(acac)
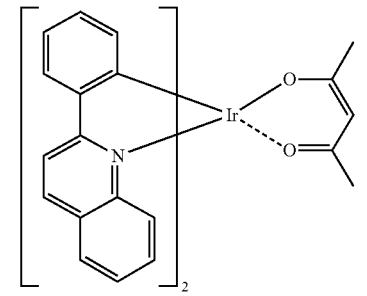
Ir(pq)₂(acac)
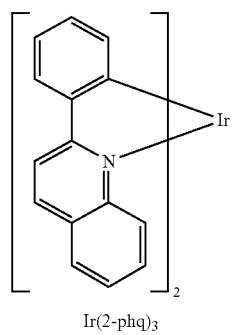
Ir(2-phq)₃
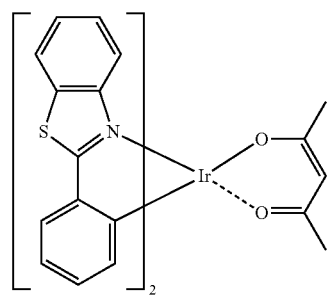
Ir(BT)₂(acac)
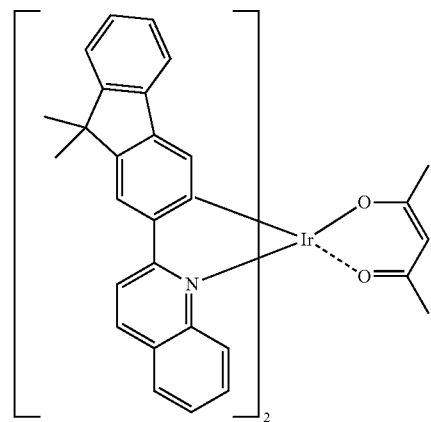
Ir(flq)₂(acac)
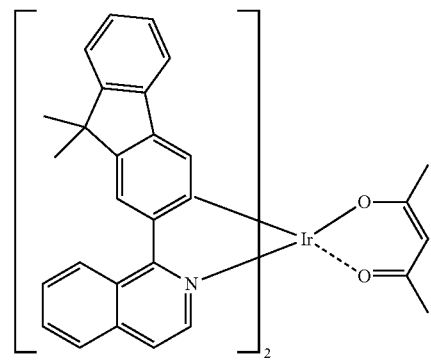
Ir(fliq)₂(acac)

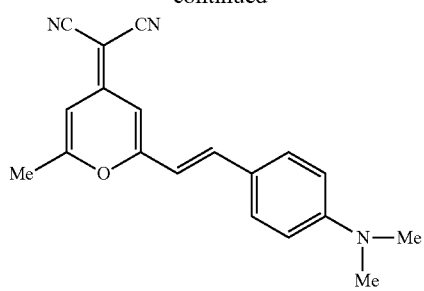
DCM
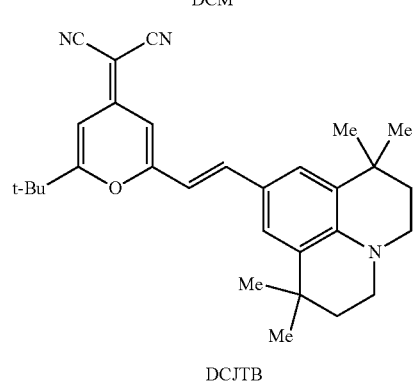
DCJTB
Non-limiting examples of the green dopant may include the compounds below:
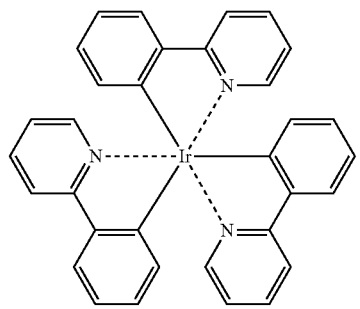
Ir(ppy)₃
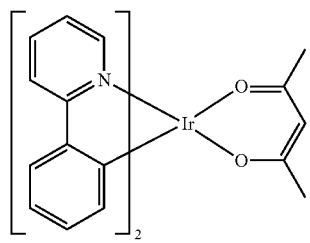
Ir(ppy)₂(acac)
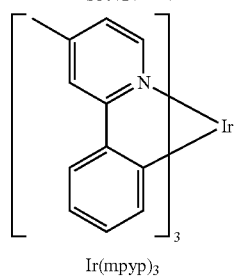
Ir(mpyp)₃
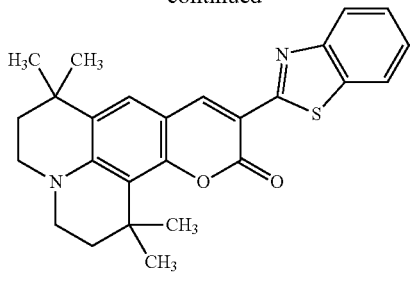
C545T
Non-limiting examples of a dopant included in the EML may include the Pt-complexes below:
D1
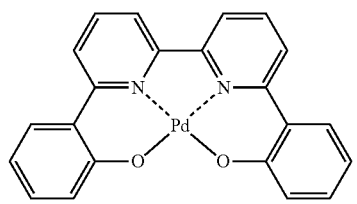
D2
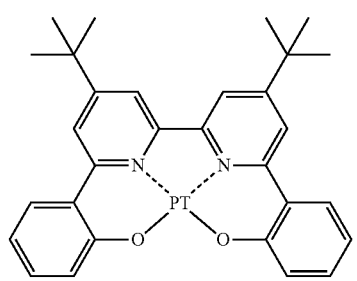
D3
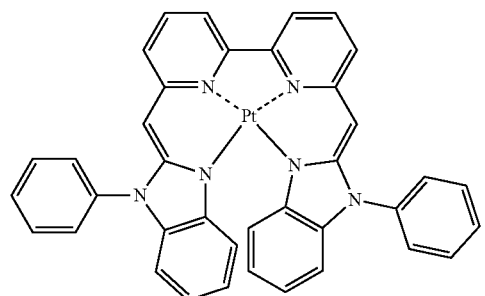
D4
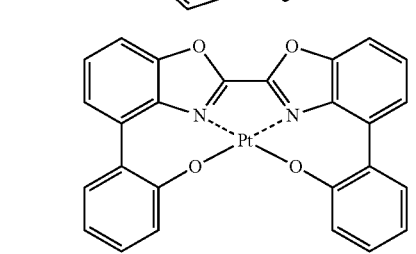
D5
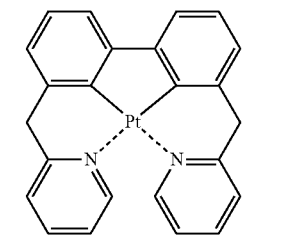

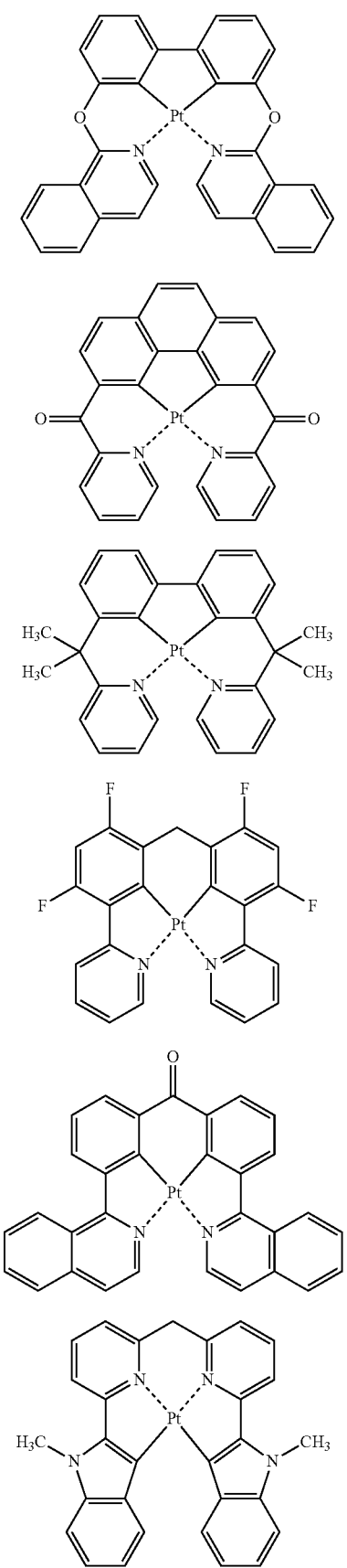
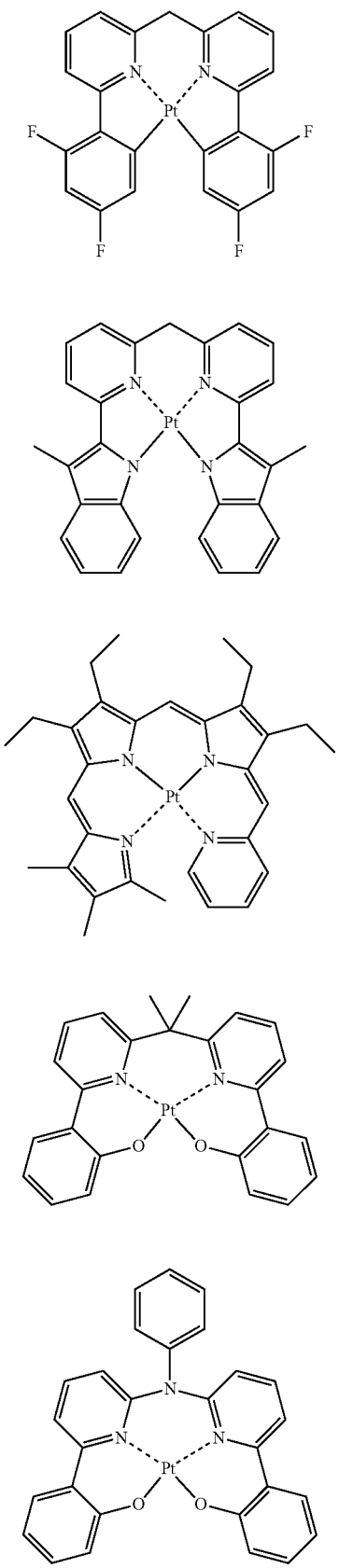

D17
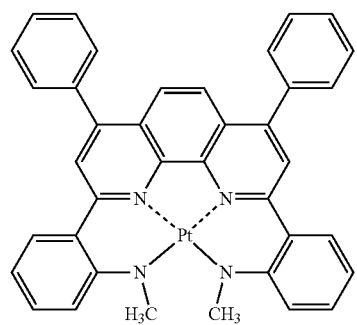
D18
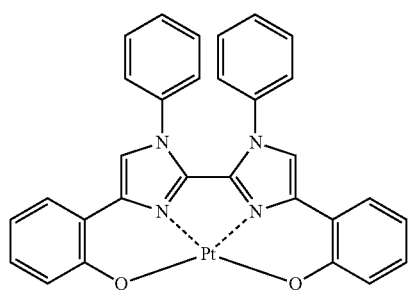
D19
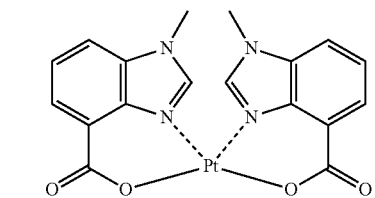
D20
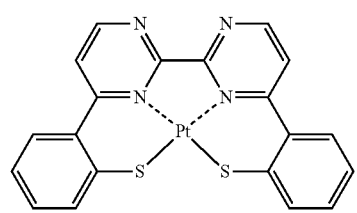
D21
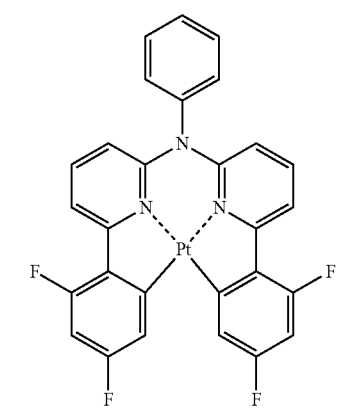
D22
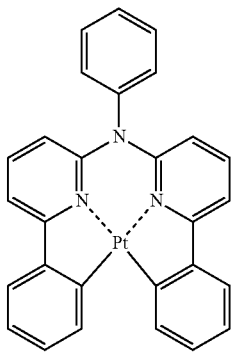
D23
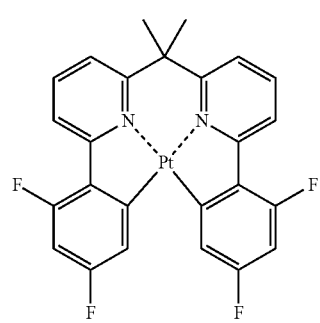
D24
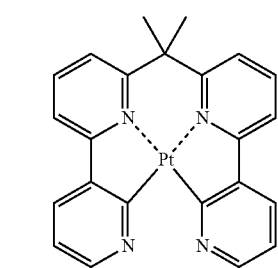
D25
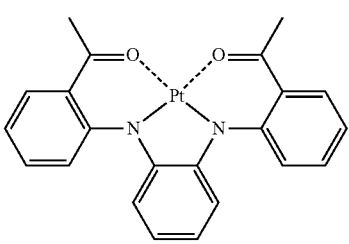
D26
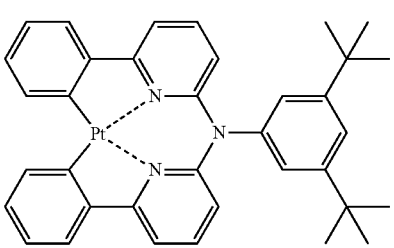

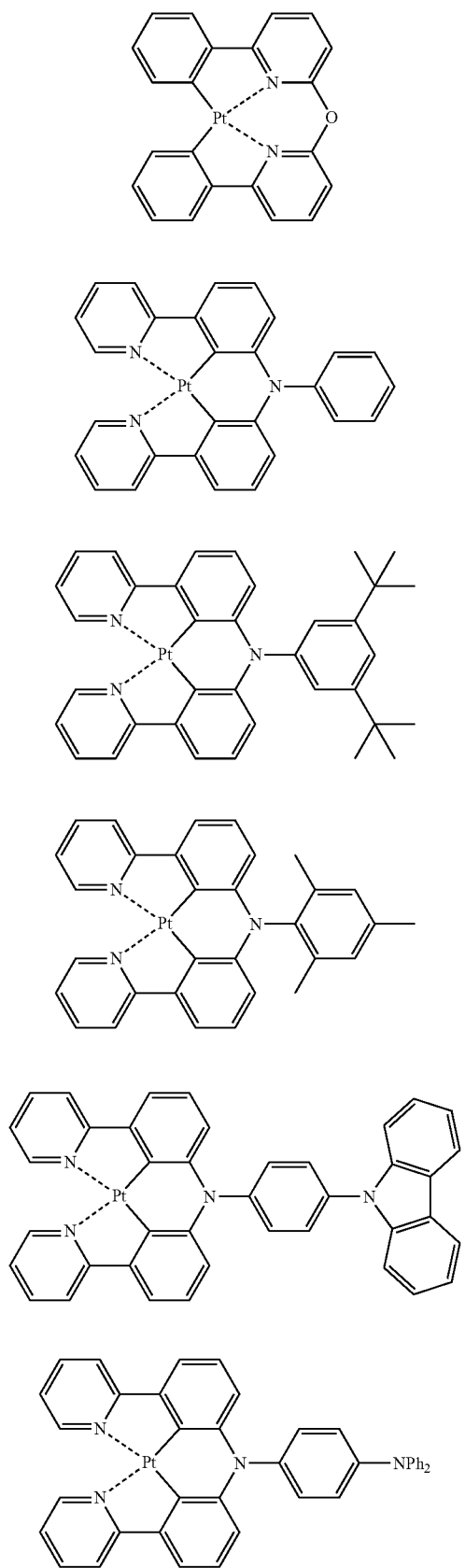
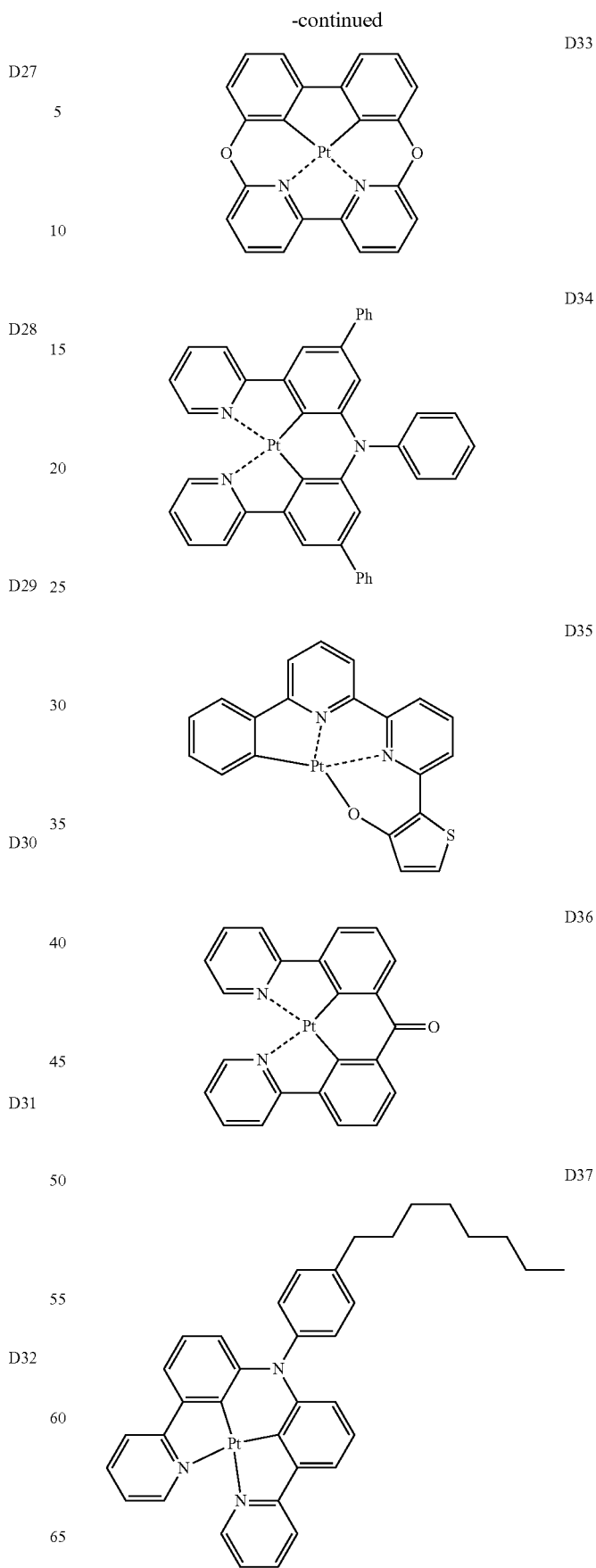

-continued
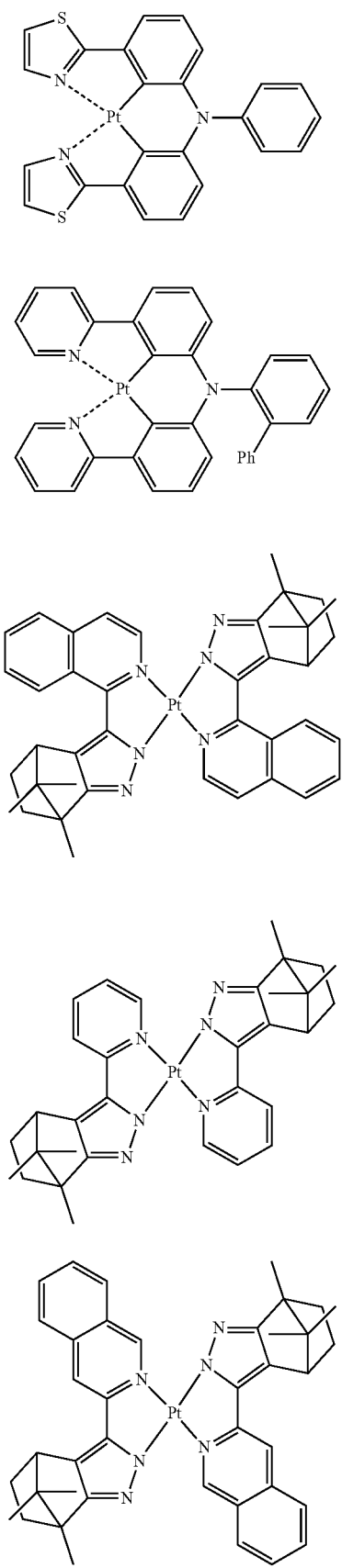
D38
D39
D40
D41
D42
-continued
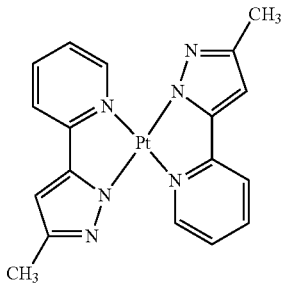
D43
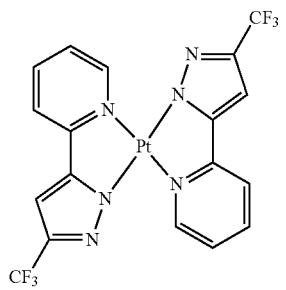
D44
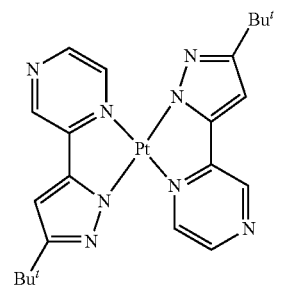
D45
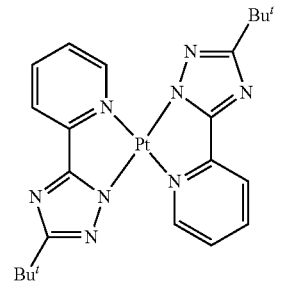
D46
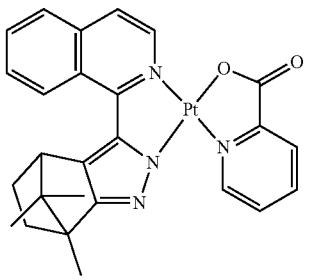
D47

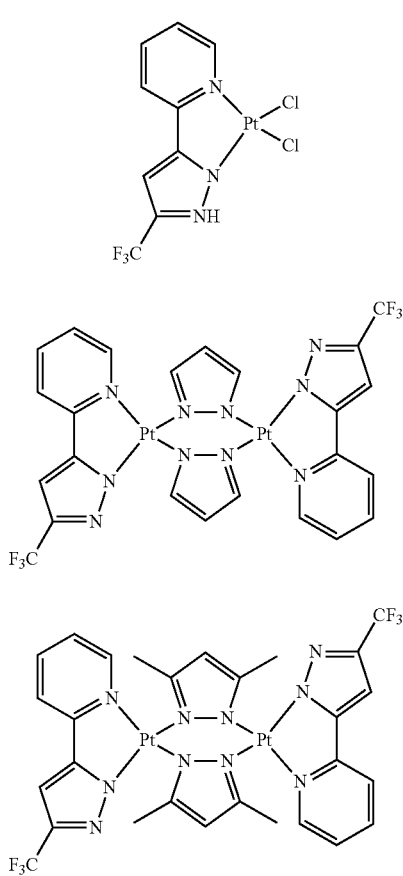
Non-limiting examples of a dopant included in the EML may include the Os-complexes below:
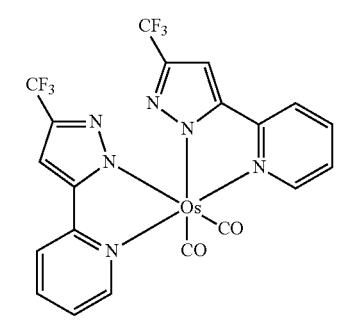
Os(fppz)₂(CO)₂
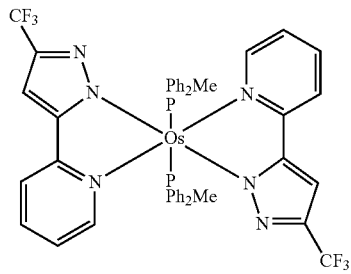
Os(fppz)₂(PPh₂Me)₂
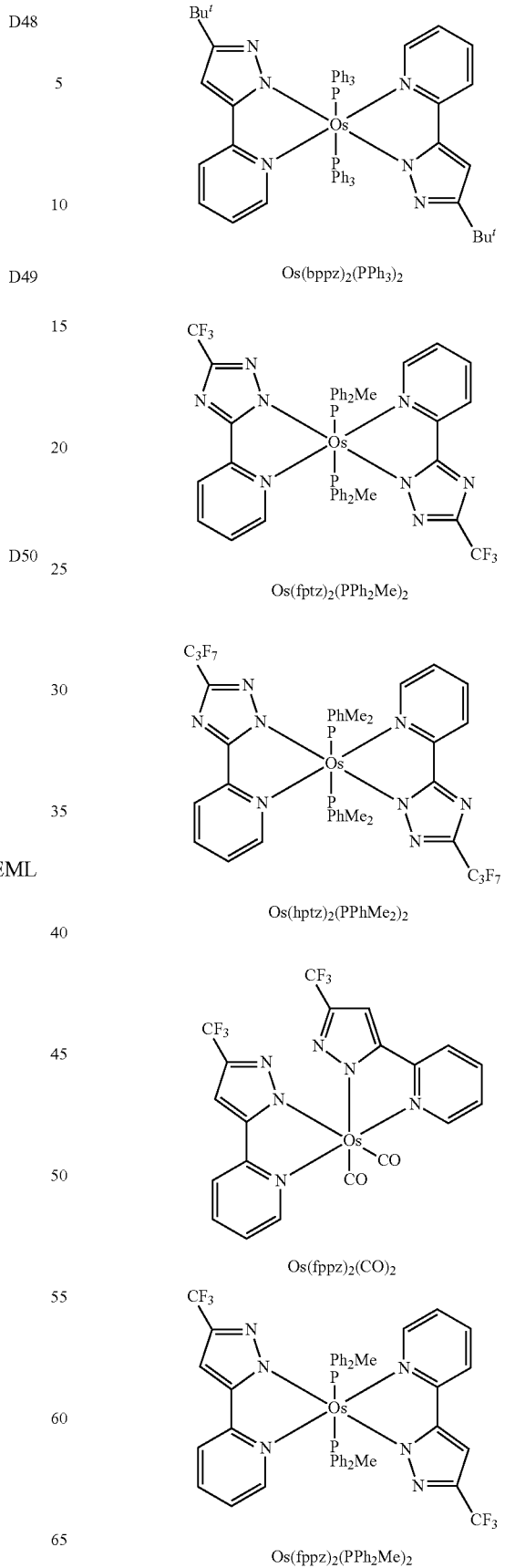

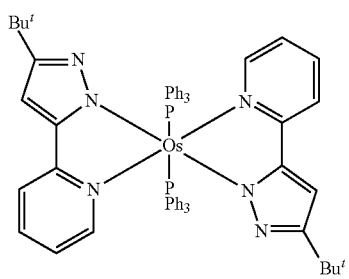

Os(bppz)₂(PPh₃)₂

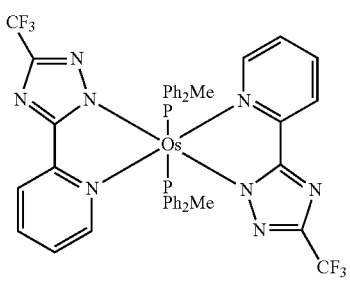

Os(fptz)₂(PPh₂Me)₂

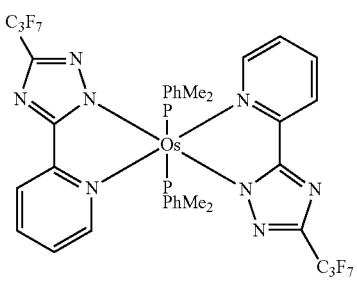

Os(hptz)₂(PPhMe₂)₂

In general, when the EML includes a host and a dopant, the amount of the dopant may range from, but is not limited to, about 0.01 to about 15 parts by weight based on 100 parts by weight of the host.

The EML may have a thickness from about 100 Å to about 1000 Å, for example, about 200 Å to about 600 Å. When the thickness of the EML is within these ranges, the EML may have good light-emission characteristics without substantially increasing driving voltage.

Then, the ETL is formed on the EML by any of a variety of methods, for example, by vacuum deposition, spin coating, casting, or the like. When the ETL is formed by vacuum deposition or spin coating, the conditions may vary according to the material used to form the ETL but may be substantially the same as those used to form the HIL. The ETL may include any known electron transport material that facilitates the stable transport of electrons injected from an electron injection electrode (i.e., a cathode). Nonlimiting examples of the electron transport material may include quinone derivatives, in particular, tris(8-quinolinorate)aluminum (Alq3), TAZ, Balq, beryllium bis(benzoquinolin-10-olate) (Bebq₂), ADN, Compound 201 below, or Compound 202 below.

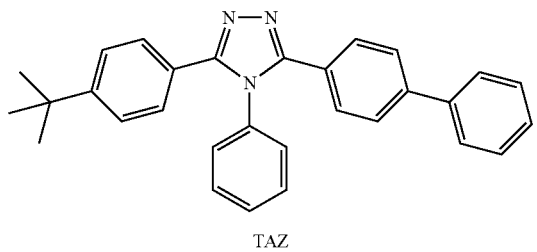

TAZ

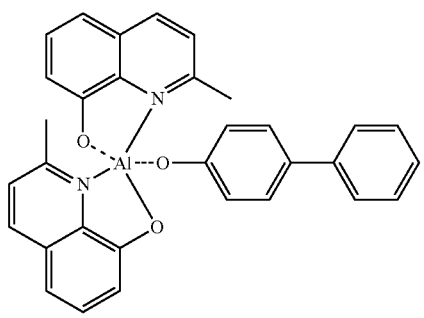

BAlq

Error! Objects cannot be created from editing field codes.

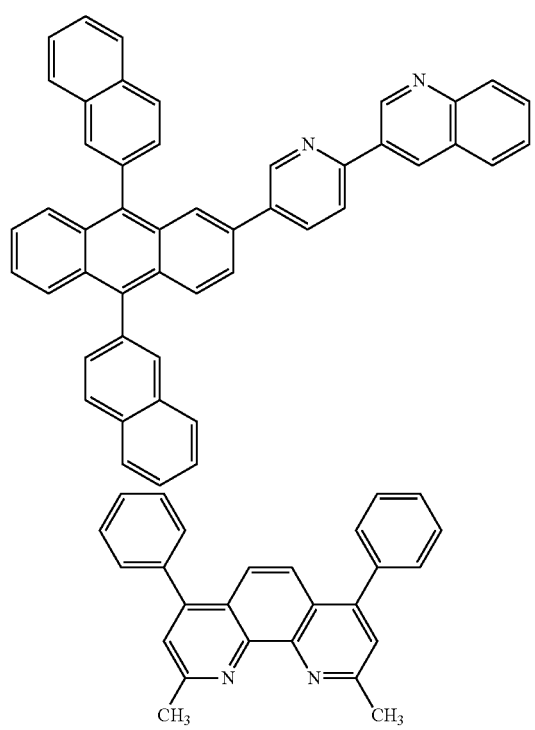

BCP

The ETL may have a thickness of about 100 Å to about 1000 Å, for example, about 150 Å to about 500 Å. When the thickness of the ETL is within these ranges, the ETL may have good electron transport characteristics without substantially increasing driving voltage.

In addition, the ETL may further include a metal-containing material in addition to the known electron transport organic compound.

The metal-containing material may include a Li complex. Non-limiting examples of the Li complex may include lithium quinolate (LiQ), or Compound 203 below:

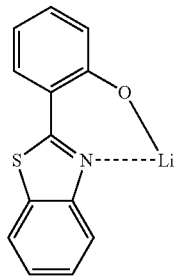

Compound 203

The EIL may be formed on the ETL and may be formed of, but is not limited to, a material that facilitates electron injection of electrons from the cathode.

The EIL may be formed of any known materials used to form an EIL layer, for example, LiF, NaCl, CsF, $Li_2O$, BaO, or the like. The deposition conditions may vary according to the material used to form the EIL but may be substantially the same as those used to form the HIL.

The EIL may have a thickness of about 1 Å to about 100 Å, for example, about 3 Å to about 90 Å. When the thickness of the EIL is within these ranges, the EIL may have good electron injection characteristics without substantially increasing driving voltage.

The second electrode is disposed on the organic layer. The second electrode may be a cathode as an electron injection electrode. In this case, the material for forming the second electrode may include a metal, an alloy, or an electrically conductive compound (which are materials having low work functions), or a mixture thereof. Non-limiting examples of such materials include lithium (Li), magnesium (Mg), aluminum (Al), aluminum-lithium (Al—Li), calcium (Ca), magnesium-indium(Mg—In), and magnesium-silver (Mg—Ag). The material may be used to form a thin film to prepare the second electrode as a transparent electrode. In order to manufacture a top-emission organic light-emitting device, a transparent cathode formed of a transparent material such as ITO or IZO may be used as the second electrode.

Thus far, an organic light-emitting device has been described with reference to FIG. 1, but the present invention is not limited thereto.

When the EML includes a phosphorescent dopant, a HBL may be formed between the HTL and the EML, or the H-functional layer and the EML, by vacuum deposition, spin coating, casting, Langmuir-Blodgett (LB) deposition, or the like in order to prevent diffusion of triplet excitons or holes into the ETL. When the HBL is formed by vacuum deposition or spin coating, the conditions may vary according to the material used to form the HBL but may be substantially the same as those used to form the HIL. In this case, the HBL may be formed of any material commonly used to form a HBL. Non-limiting examples of such HBL materials include oxadiazole derivatives, triazole derivatives, and phenathroline derivatives. For example, the HBL may be formed of BCP, depicted below.

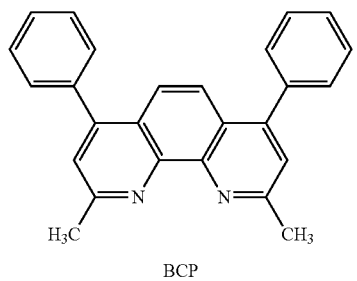 [SMILES: Cc1cc(-c2ccccc2)c2ccc3c(-c4ccccc4)cc(C)nc3c2n1 ; "BCP"]

BCP

The HBL may have a thickness ranging from about 20 Å to about 1000 Å, for example, about 30 Å to about 300 Å. When the thickness of the HBL is within these ranges, the HBL may have good hole block characteristics without substantially increasing driving voltage.

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode and may be electrically connected to a source electrode or a drain electrode of the thin-film transistor. Moreover, the organic light-emitting device may also be included in flat panel display devices having double-sided screens.

The organic layer of the organic light-emitting device according to an embodiment of the present invention may be formed by a vapor deposition method using the compound according to an embodiment of the present invention, or may be formed using a wet method of coating the compound prepared using a solution.

Hereinafter, an organic light-emitting device will be described with reference to Synthesis Examples and Examples. However, these examples are presented for illustrative purposes only, and are not intended to limit the scope of the present invention.

SYNTHESIS EXAMPLES

Synthesis of Compound 11

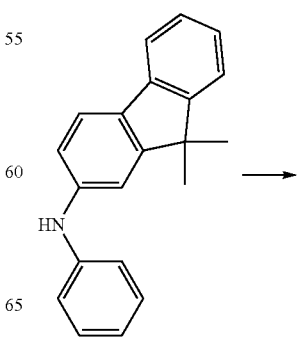

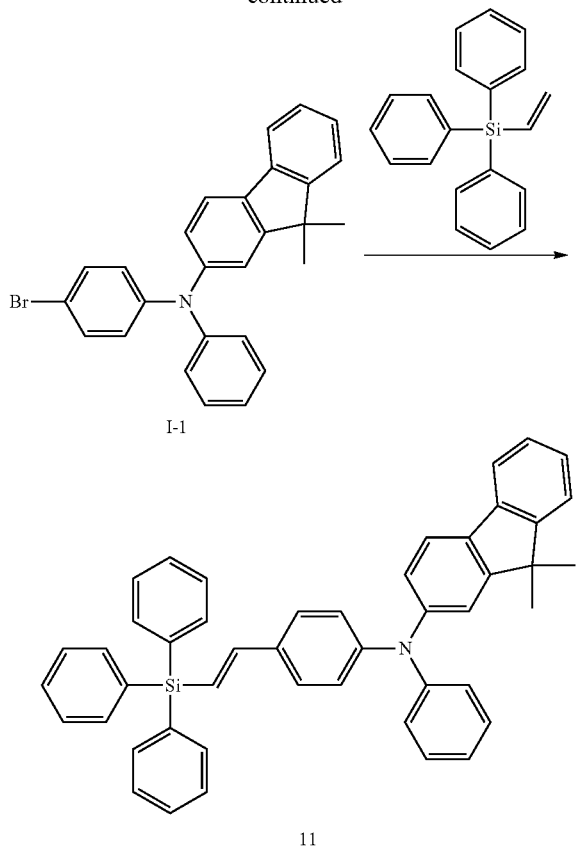

2.85 g (10.0 mmol) of 2-(9,9-dimethylfluoreny)-phenyl amine, 4.23 g (15.0 mmol) of 1-bromo-4-tri-iodo benzene, 0.18 g (0.2 mmol) of $Pd_2(dba)_3$, 0.04 g (0.2 mmol) of $P(tBu)_3$, and 1.44 g (15.0 mmol) of NaOtBu were dissolved in 30 mL of toluene and stirred at a temperature of 80° C. for 4 hours. After the reaction was completed, the reaction product was cooled to room temperature, 40 mL of water was added to the reaction product, and the reaction product was extracted three times with 50 mL of ethylether. The organic layer was collected and then dried using magnesium sulfate, and the solvent was evaporated. The residue was separated and purified using silica gel column chromatography to obtain 3.30 g of Intermediate I-1 (Yield: 75%).

3.0 g (6.8 mmol) of Intermediate I-1, 1.95 g (6.8 mmol) of triphenylvinylsilane, 0.16 g (0.17 mmol) of $Pd_2(dba)_3$, 1.14 mL (8.16 mmol) of $Et_3N$, and 0.16 g (0.68 mmol) of tri-2-furyl phosphine (TFP) were dissolved in 40 mL of THF and were stirred at a temperature of 50° C. for 6 hours. After the reaction was completed, the reaction product was cooled to room temperature, 40 mL of water was added to the reaction product, and the reaction product was extracted three times with 50 mL of ethylether. The organic layer was collected and then dried using magnesium sulfate, and the solvent was evaporated. The residue was separated and purified using silica gel column chromatography to obtain 3.60 g of Compound 11 (Yield: 82%). The obtained compound was confirmed by $^1$H NMR and MS/FAB.

$C_{47}H_{39}NSi$: calculated value 645.29, measured value 645.30

Synthesis of Compound 36

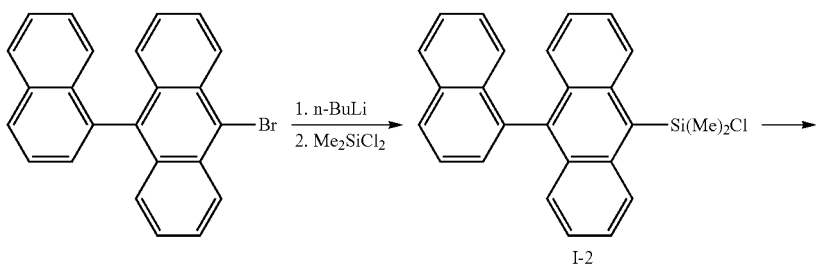

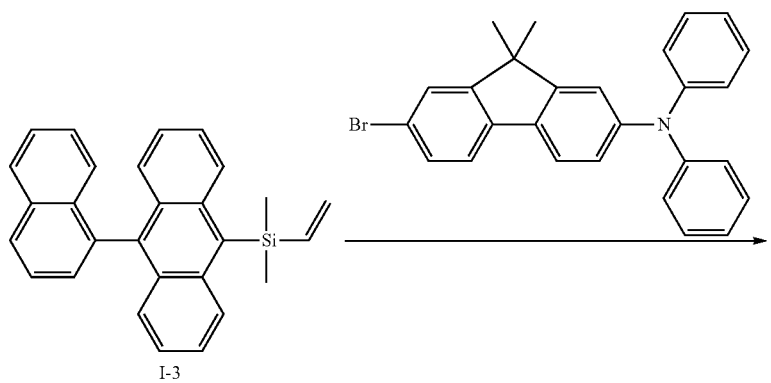

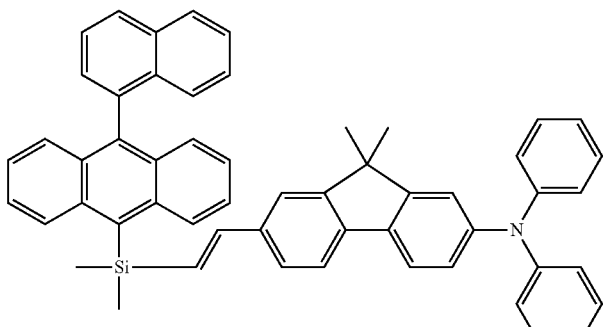

36

7.66 g (20.0 mmol) of 9-bromo-10-naphthalene-1-yl-anthracene was dissolved in 30 mL of THF and then 8.8 mL (22.0 mmol) of n-BuLi(2.5M in Hexane) was slowly dropwise added at a temperature of −78° C. The solution was stirred at the same temperature, that is, −78° C., for one hour and then 3.89 g (30 mmol) of dichloro-dimethylsilane was slowly dropwise added to the solution. After the reaction was completed, the reaction solution was stirred at a temperature of −78° C. for one hour and then was further stirred at room temperature for one hour. The reaction solution was dried and the solvent was evaporated. The residue obtained was separated and purified using silica gel column chromatography to obtain 5.56 g of Intermediate I-2 (Yield: 70%).

5 g (12.6 mmol) of Intermediate I-2 was dissolved in 40 mL of THF, 2.48 g (18.9 mmol) of vinyl-magnesium bromide was slowly dropwise added at a temperature of −40° C., and the resulting solution was stirred at a temperature of 0° C. for 2 hours. After the reaction was completed, 40 mL of water was added to the reaction solution and the reaction solution was extracted three times with 50 mL of ethylether. The organic layer was collected and then dried using magnesium sulfate, and the solvent was evaporated. The residue was separated and purified using silica gel column chromatography to obtain 3.57 g of Intermediate I-3 (Yield: 73%).

3.20 g (8.24 mmol) of Intermediate I-3, 3.63 g (8.24 mmol) of 7-bromo-9,9-dimethyl-9-h-fluorene-2-yl)-diphenyl amine, 0.20 g (0.21 mmol) of Pd$_2$(dba)$_3$, 1.38 mL (9.89 mmol) of Et$_3$N, and 0.19 g (0.82 mmol) of tri-2-furyl phosphine (TFP) were dissolved in 50 mL of THF and then were stirred at a temperature of 50° C. for 7 hours. After the reaction was completed, the reaction product was cooled to room temperature, 50 mL of water was added to the reaction product, and the reaction product was extracted three times with 50 mL of ethylether. The organic layer was collected and then dried using magnesium sulfate, and the solvent was evaporated. The residue was separated and purified using silica gel column chromatography to obtain 4.62 g of compound 36 (Yield: 75%). The obtained compound was confirmed by $^1$H NMR and MS/FAB. C$_{55}$H$_{45}$NSi: Calculated value 747.33, Measured value 747.31

Synthesis of Compound 37

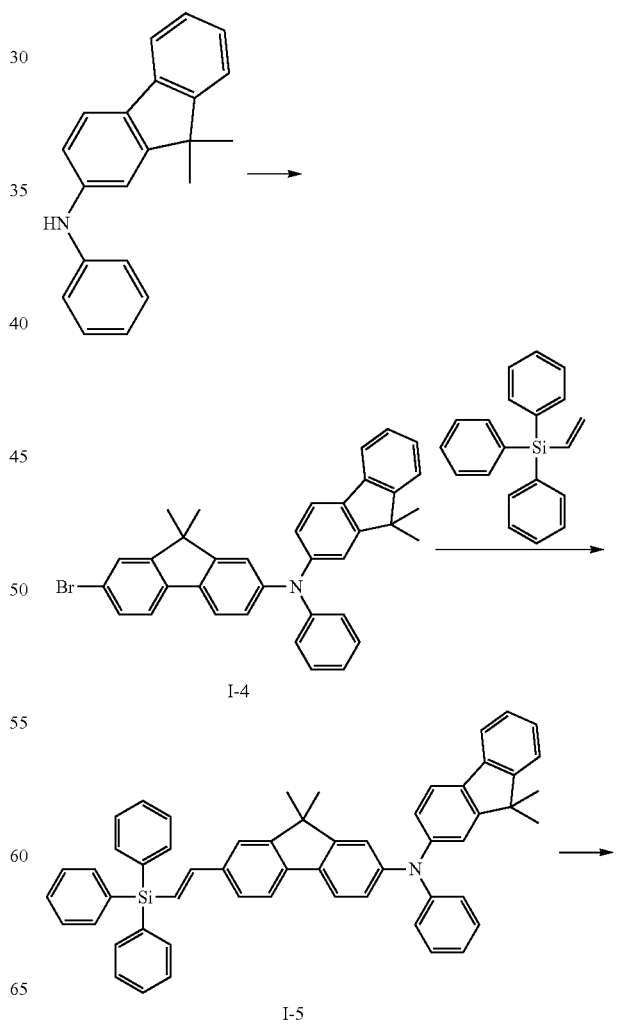

-continued

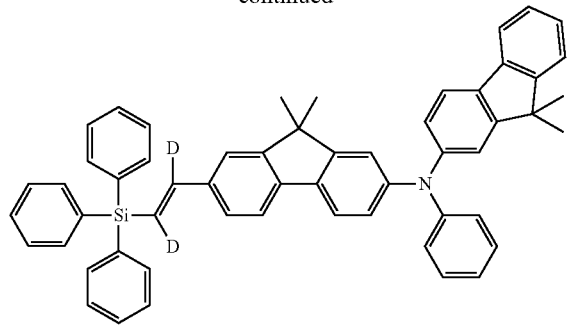

37

2.85 g (10.0 mmol) of 2-(9,9-dimethylfluoreny)-phenyl amine, 5.28 g (15.0 mmol) of 2,7-dibromo-9,9-dimethyl-9-h-fluorene, 0.18 g (0.2 mmol) of $Pd_2(dba)_3$, 0.04 g (0.2 mmol) of $P(tBu)_3$, and 1.44 g (15.0 mmol) of NaOtBu were dissolved in 40 mL of toluene and were stirred at a temperature of 80° C. for four hours. After the reaction was completed, the reaction product was cooled to room temperature, 40 mL of water was added to the reaction product, and the reaction product was extracted three times with 50 mL of ethylether. The organic layer was collected and then dried using magnesium sulfate, and the solvent was evaporated. The residue was separated and purified using silica gel column chromatography to obtain 3.90 g of Intermediate I-4 (Yield: 70%).

3.4 g (6.1 mmol) of Intermediate I-4, 1.75 g (6.1 mmol) of triphenylvinylsilane, 0.14 g (0.15 mmol) of $Pd_2(dba)_3$, 1.02 mL (7.32 mmol) of $Et_3N$, and 0.14 g (0.61 mmol) of tri-2-furyl phosphine (TFP) were dissolved in 40 mL of THF and then were stirred at a temperature of 50° C. for 6 hours. After the reaction was completed, the reaction product was cooled to room temperature, 40 mL of water was added to the reaction product, and the reaction product was extracted three times with 50 mL of ethylether. The organic layer was collected and then dried using magnesium sulfate, and the solvent was evaporated. The residue was separated and purified using silica gel column chromatography to obtain 3.63 g of Intermediate I-5 (Yield: 78%).

3.05 g (4.0 mmol) of Intermediate I-5, 0.115 g (0.12 mmol) of $[(Ph_3)P]_3Ru(CO)(Cl)H$ carbonylchlorohydridotris(triphenylphosphine) ruthenium (II), and 0.72 mL (40.0 mmol) of $D_2O$ were dissolved in 50 mL of 1,4-dioxane and were stirred at a temperature of 80° C. for 12 hours. After the reaction was completed, the reaction product was cooled to room temperature, the solvent was removed, and the reaction product was extracted three times with 40 mL of water and 40 mL of dichloromethane. The organic layer was collected and then dried using magnesium sulfate, and the solvent was evaporated. The residue was separated and purified using silica gel column chromatography to obtain 2.66 g of compound 37 (Yield: 87%). The obtained compound was confirmed by $^1$H NMR and MS/FAB.

$C_{56}H_{45}D_2NSi$: Calculated value 763.36, Measured value 763.35

Synthesis of Compound 64

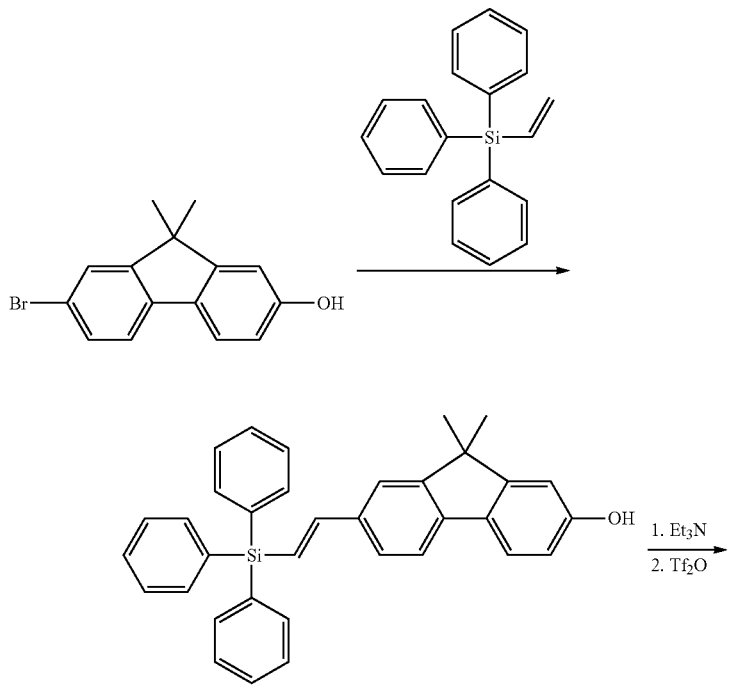

I-6

-continued
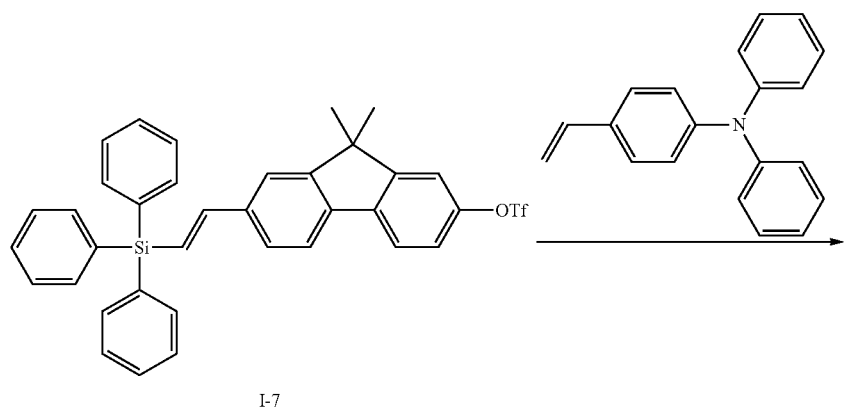
I-7
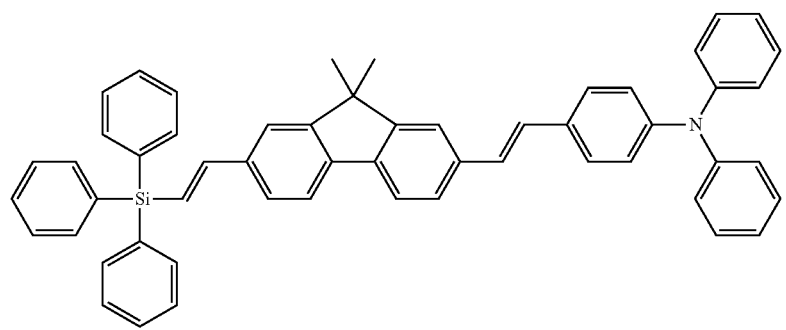
64
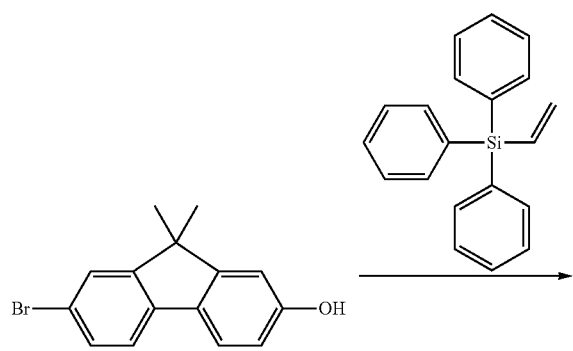
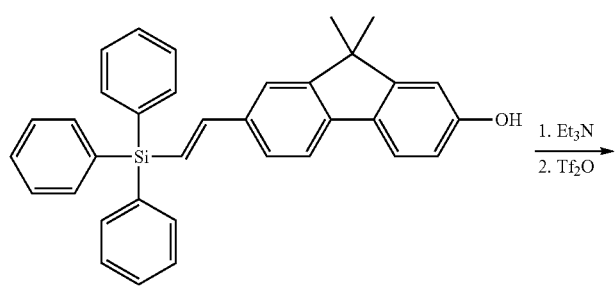
I-6

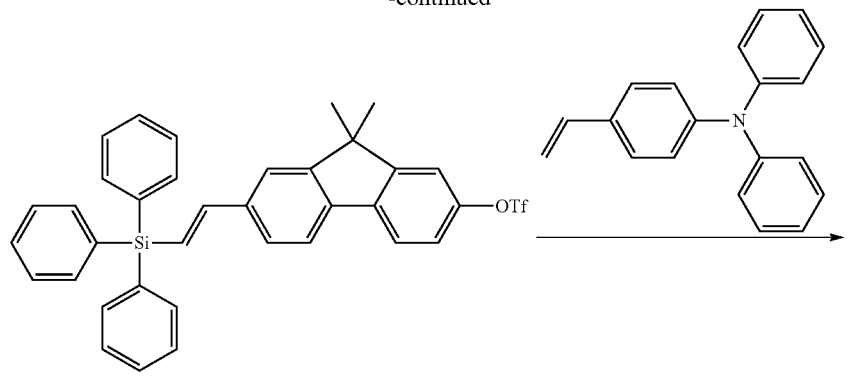

I-7

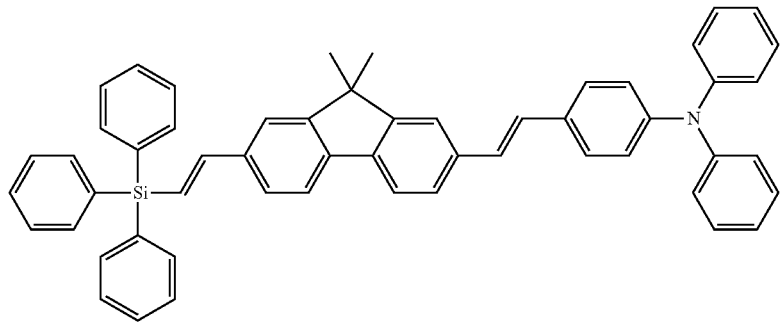

64

2.50 g (8.50 mmol) of 7-bromo-9,9-dimethyl-9-h-fluorene-2-ol, 2.43 g (8.50 mmol) of triphenylvinylsilane, 0.19 g (0.21 mmol) of $Pd_2(dba)_3$, 1.43 mL (10.2 mmol) of $Et_3N$, and 0.20 g (0.85 mmol) of tri-2-furyl phosphine (TFP) were dissolved in 60 mL of THF and were stirred at a temperature of 50° C. for 6 hours. After the reaction was completed, the reaction product was cooled to room temperature, 40 mL of water was added to the reaction product, and the reaction product was extracted three times with 60 mL of ethylether. The organic layer was collected and then dried using magnesium sulfate, and the solvent was evaporated. The residue was separated and purified using silica gel column chromatography to obtain 3.36 g of Intermediate I-6 (Yield: 80%).

3.0 g (6.0 mmol) of Intermediate I-6 was dissolved in 30 mL of $CH_2Cl_2$ and 2.52 mL (18.0 mmol) of $NEt_3$, and 2.54 g (9.0 mmol) of $Tf_2O$ were slowly dropwise added at a temperature of 0° C., and the resulting solution was stirred at room temperature for 2 hours. After the reaction was completed, the reaction product was cooled to room temperature, 40 mL of water was added to the reaction product, and the reaction product was extracted three times with 50 mL of dichloromethane. The organic layer was collected and then dried using magnesium sulfate, and the solvent was evaporated. The residue was separated and purified using silica gel column chromatography to obtain 3.31 g of Intermediate I-7 (Yield: 88%).

3.13 g (5.0 mmol) of Intermediate I-7, 1.04 g (5.0 mmol) of diphenyl-(4-vinyl-phenyl)-amine, 0.056 g (0.25 mmol) of $Pd(OAc)_2$, 0.76 g (0.25 mmol) of $P(p-toly)_3$, and 1.019 (10.0 mmol) of $Et_3N$ were dissolved in 40 ml of dimethylacetamide (DMAc) and were stirred at a temperature of 100° C. for 4 hours. After the reaction was completed, the reaction product was cooled to room temperature, 40 mL of water was added to the reaction product, and the reaction product was extracted three times with 50 mL of diethylether. The organic layer was collected and then dried using magnesium sulfate, and the solvent was evaporated. The residue was separated and purified using silica gel column chromatography to obtain 2.66 g of compound 63 (Yield: 71%). The obtained compound was confirmed by $^1H$ NMR and MS/FAB.

$C_{55}H_{45}NSi$: Calculated value 747.33, Measured value 747.32

Synthesis of Compound 68

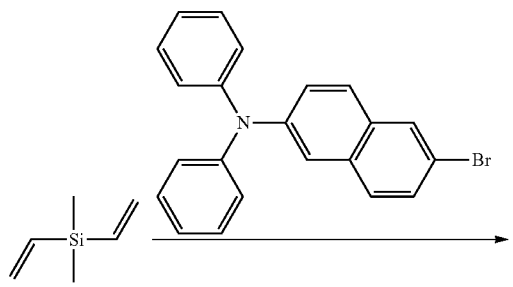

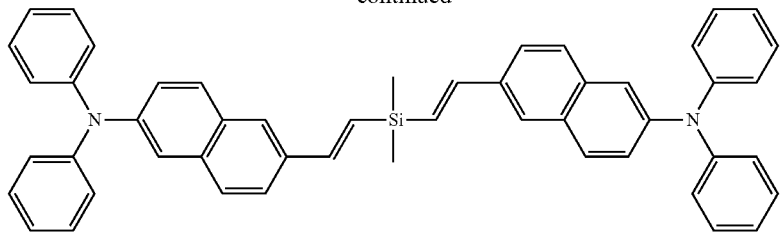

68

0.79 g (7.06 mmol) of dimethyldivinylsilane, 5.28 g (14.1 mmol) of (6-bromo-naphthalene-2-yl)-diphenyl amine, 0.16 g (0.18 mmol) of $Pd_2(dba)_3$, 1.19 mL (8.47 mmol) of $Et_3N$, and 0.17 g (0.71 mmol) of tri-2-furyl phosphine (TFP) were dissolved in 50 mL of THF and were stirred at a temperature of 50° C. for 7 hours. After the reaction was completed, the reaction product was cooled to room temperature, 50 mL of water was added to the reaction product, and the reaction product was extracted three times with 60 mL of ethylether. The organic layer was collected and then dried using magnesium sulfate, and the solvent was evaporated. The residue was separated and purified using silica gel column chromatography to obtain 3.36 g of compound 67 (Yield: 68%). The obtained compound was confirmed by $^1$H NMR and MS/FAB.

$C_{50}H_{42}N_2Si$: Calculated value 698.31, Measured value 698.32

Synthesis of Compound 70

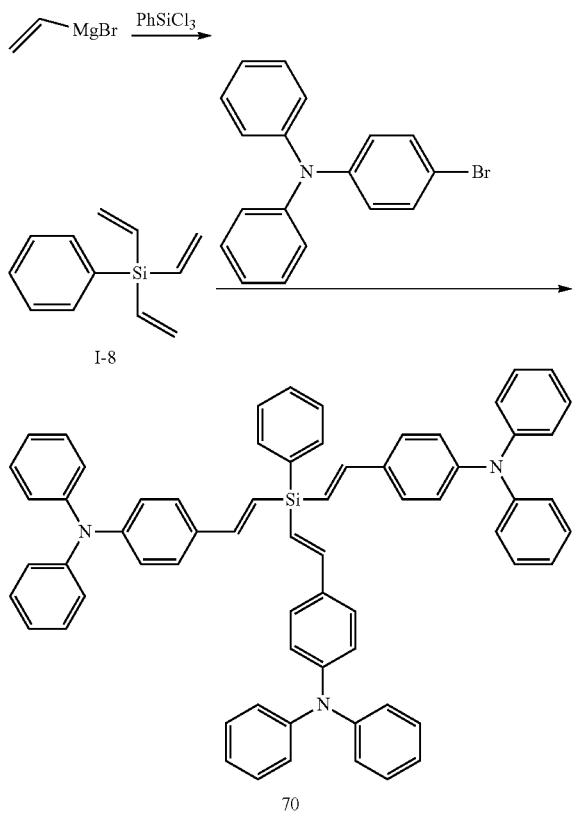

2.02 g (9.56 mmol) of trichloro-phenylsilane was dissolved in 50 mL of THF, 3.76 g (28.7 mmol) of vinyl-magnesium bromide was slowly dropwise added at a temperature of −40° C., and the resulting solution was stirred at a temperature of 0° C. for 3 hours. After the reaction was completed, 30 mL of water was added to the reaction product and the reaction product was extracted three times with 30 mL of ethylether. The organic layer was collected and then dried using magnesium sulfate, and the solvent was evaporated. The residue was separated and purified using silica gel column chromatography to obtain 1.21 g of Intermediate I-8 (Yield: 68%).

1.0 g (5.38 mmol) of Intermediate I-8, 5.23 g (16.1 mmol) of (4-bromo-phenyl)-diphenyl amine, 0.12 g (0.13 mmol) of $Pd_2(dba)_3$, 0.91 mL (6.46 mmol) of $Et_3N$, and 0.31 g (0.54 mmol) of tri-2-furyl phosphine (TFP) were dissolved in 60 mL of THF and were stirred at a temperature of 50° C. for 9 hours. After the reaction was completed, the reaction product was cooled to room temperature, 60 mL of water was applied to the reaction product, and the reaction product was extracted three times with 60 mL of ethylether. The organic layer was collected and then dried using magnesium sulfate, and the solvent was evaporated. The residue was separated and purified using silica gel column chromatography to obtain 3.20 g of compound 70 (Yield: 65%). The obtained compound was confirmed by $^1$H NMR and MS/FAB.

$C_{66}H_{53}N_3Si$: Calculated value 915.40, Measured value 915.42

MS/FAB and $^1$H NMR data for the compounds reported in the above synthesis examples and an equivalent weight of corresponding intermediates prepared in the above synthesis examples will now be described.

Compound 1: $C_{38}H_{31}NSi$ FAB/MS
Calculated value 529.22, Measured value 529.24
$^1$H NMR (CDCl$_3$, 400 MHz) ☐ 7.54-7.52 (m, 6H), 7.35-7.32 (m, 6H), 7.26-7.21 (m, 6H), 7.18-7.11 (m, 5H), 7.07-7.04 (m, 2H), 6.98-6.93 (t, 2H), 6.83-6.81 (m, 4H)

Compound 5: $C_{38}H_{29}F_2NSi$ FAB/MS
Calculated value 565.20, Measured value 565.23
$^1$H NMR (CDCl$_3$, 400 MHz) ☐ 7.54-7.52 (m, 6H), 7.35-7.32 (m, 6H), 7.26-7.21 (m, 6H), 7.18-7.11 (m, 5H), 7.07-7.04 (m, 2H), 6.98-6.93 (t, 2H), 6.83-6.81 (m, 4H)

Compound 8: $C_{39}H_{30}N_2Si$ FAB/MS
Calculated value 554.22, Measured value 554.20
$^1$H NMR (CDCl$_3$, 400 MHz) ☐ 7.55-7.53 (m, 6H), 7.39-7.32 (m, 6H), 7.28-7.22 (m, 6H), 7.08-7.01 (m, 4H), 6.95-6.92 (m, 2H), 6.88-6.85 (m, 2H), 6.67 (t, 2H), 6.56-6.52 (m, 2H)

Compound 11: $C_{47}H_{39}NSi$ FAB/MS
Calculated value 645.29, Measured value 645.30
$^1$H NMR (CDCl$_3$, 400 MHz) ☐ 7.77 (d, 1H), 7.57-7.54 (m, 7H), 7.37-7.31 (m, 7H), 7.30-7.21 (m, 6H), 7.13-7.01 (m, 5H), 6.97-6.95 (m, 2H), 6.87-6.81 (m, 2H), 6.75 (d, 1H), 6.62-6.59 (m, 2H), 1.62 (s, 6H)

Compound 12: $C_{50}H_{38}N_2Si$ FAB/MS
Calculated value 694.28, Measured value 694.29
$^1$H NMR (CDCl$_3$, 400 MHz) ☐ 8.21 (d, 1H), 7.56-7.48 (m, 10H), 7.41 (d, 1H), 7.39-7.31 (m, 8H), 7.30-7.21 (m, 9H), 7.12-7.08 (m, 3H), 6.99-6.96 (m, 3H), 6.76 (t, 1H), 6.63-6.60 (m, 2H)

Compound 14: $C_{47}H_{46}N_2Si$ FAB/MS
Calculated value 666.34, Measured value 666.32
$^1$H NMR (CDCl$_3$, 400 MHz) ☐ 8.23 (d, 1H), 7.86-7.81 (m, 2H), 7.62 (d, 1H), 7.55-7.50 (m, 4H), 7.45-7.42 (m, 2H), 7.40-7.28 (m, 6H), 7.17-7.12 (m, 2H), 7.02 (d, 1H), 6.98-6.93 (m, 3H), 6.84 (d, 1H), 6.72 (d, 1H), 6.56-6.51 (m, 1H), 1.61 (s, 6H), 0.93 (t, 9H), 0.57 (q, 6H)

Compound 15: $C_{52}H_{41}NSi$ FAB/MS
Calculated value 707.30, Measured value 707.33
$^1$H NMR (CDCl$_3$, 400 MHz) ☐ 7.85-7.80 (m, 3H), 7.73-7.69 (m, 2H), 7.67 (d, 1H), 7.66 (d, 1H), 7.61-7.58 (m, 2H), 7.53 (d, 1H), 7.50-7.43 (m, 3H), 7.41-7.27 (m, 10H), 7.15-7.10 (m, 4H), 7.03 (t, 1H), 6.98 (d, 1H), 6.81-6.78 (m, 2H), 6.76-6.65 (m, 2H), 6.50-6.48 (m, 2H), 0.40 (s, 6H)

Compound 17: $C_{48}H_{37}NSi$ FAB/MS
Calculated value 655.27, Measured value 655.26
$^1$H NMR (CDCl$_3$, 400 MHz) ☐ 8.16 (d, 1H), 7.86 (d, 1H), 7.60-7.56 (m, 6H), 7.52-7.45 (m, 8H), 7.37-7.32 (m, 6H), 7.29-7.20 (m, 6H), 7.12-7.07 (m, 2H), 7.00-6.94 (m, 3H), 6.88 (d, 1H), 6.81 (t, 1H), 6.74-6.71 (m, 2H)

Compound 19: $C_{43}H_{34}N_2Si$ FAB/MS
Calculated value 606.25, Measured value 606.27
$^1$H NMR (CDCl$_3$, 400 MHz) ☐ 8.22 (d, 1H), 7.63-7.61 (m, 2H), 7.58-7.53 (m, 6H), 7.48-7.42 (m, 5H), 7.39-7.35 (m, 6H), 7.32-7.23 (m, 7H), 7.05-7.01 (m, 2H), 6.93-6.90 (m, 1H), 6.84-6.81 (m, 2H), 6.76-6.72 (m, 2H)

Compound 22: $C_{44}H_{33}NSi$ FAB/MS
Calculated value 603.24, Measured value 603.23
$^1$H NMR (CDCl$_3$, 400 MHz) ☐ 8.11 (d, 2H), 7.60-7.53 (m, 10H), 7.48-7.46 (m, 2H), 7.44-7.41 (m, 2H), 7.37-7.35 (m, 10H), 7.31-7.26 (m, 5H), 7.21-7.17 (m, 1H), 7.07 (d, 1H)

Compound 25: $C_{56}H_{42}FNSi$ FAB/MS
Calculated value 775.31, Measured value 775.33
$^1$H NMR (CDCl$_3$, 400 MHz) ☐ 7.73-7.69 (m, 2H), 7.66-7.61 (m, 3H), 7.56-7.47 (m, 12H), 7.45-7.40 (m, 8H), 7.36-7.31 (m, 6H), 7.29-7.24 (m, 2H), 7.20-7.05 (m, 4H), 6.96-6.90 (m, 2H), 6.83-6.78 (m, 1H), 6.63-6.59 (m, 2H)

Compound 26: $C_{44}H_{30}D_5NSi$ FAB/MS
Calculated value 610.28, Measured value 610.30
$^1$H NMR (CDCl$_3$, 400 MHz) ☐ 7.56-7.52 (m, 6H), 7.51-7.47 (m, 2H), 7.46-7.44 (m, 4H), 7.36-7.33 (m, 6H), 7.27-7.20 (m, 4H), 7.13-7.08 (m, 2H), 6.95-6.89 (m, 3H), 6.77-6.72 (m, 1H), 6.61-6.58 (m, 2H)

Compound 30: $C_{49}H_{38}N_2Si$ FAB/MS
Calculated value 682.28, Measured value 682.31
$^1$H NMR (CDCl$_3$, 400 MHz) ☐ 8.87 (d, 1H), 8.68-8.64 (m, 1H), 7.86-7.82 (m, 1H), 7.56-7.48 (m, 8H), 7.46-7.40 (m, 5H), 7.38-7.33 (m, 6H), 7.28-7.24 (m, 3H), 7.20-7.15 (m, 3H), 7.09-7.04 (m, 3H), 6.89 (d, 1H), 6.72 (t, 1H), 6.66-6.62 (m, 2H), 6.46-6.43 (m, 2H), 6.40-6.37 (m, 1H)

Compound 32: $C_{53}H_{43}NSi$ FAB/MS
Calculated value 721.32, Measured value 721.30
$^1$H NMR (CDCl$_3$, 400 MHz) ☐ 7.74 (d, 1H), 7.67-7.60 (m, 4H), 7.56-7.48 (m, 7H), 7.46-7.38 (m, 5H), 7.37-7.31 (m, 5H), 7.28-7.22 (m, 4H), 7.09-7.04 (m, 2H), 6.92-6.85 (m, 4H), 6.79 (t, 1H), 6.73-6.69 (m, 2H), 6.56-6.52 (m, 2H), 1.72 (s, 6H)

Compound 36: $C_{55}H_{45}NSi$ FAB/MS
Calculated value 747.33, Measured value 747.31
$^1$H NMR (CDCl$_3$, 400 MHz) ☐ 8.08 (d, 2H), 7.83 (d, 1H), 7.78 (d, 2H), 7.74-7.69 (m, 3H), 7.65-7.60 (m, 2H), 7.54-7.51 (m, 2H), 7.48-7.42 (m, 2H), 7.37-7.33 (m, 2H), 7.18-7.10 (m, 6H), 7.02 (t, 1H), 6.88-6.79 (m, 5H), 6.70 (d, 1H), 6.58-6.53 (m, 4H), 1.65 (s, 6H), 0.63 (s, 6H)

Compound 37: $C_{56}H_{45}D_2NSi$ FAB/MS
Calculated value 763.36, Measured value 763.35
$^1$H NMR (CDCl$_3$, 400 MHz) ☐ 7.79-7.72 (m, 2H), 7.67-7.65 (m, 1H), 7.60 (t, 1H), 7.56-7.52 (m, 7H), 7.37-7.31 (m, 8H), 7.28-7.26 (m, 3H), 7.13-7.05 (m, 4H), 7.00-6.96 (m, 2H), 6.92-6.87 (m, 1H), 6.74 (d, 1H), 6.69 (d, 1H), 6.52-6.47 (m, 2H), 1.60 (s, 12H)

Compound 39: $C_{59}H_{46}FNSi$ FAB/MS
Calculated value 815.34, Measured value 815.33
$^1$H NMR (CDCl$_3$, 400 MHz) ☐ 7.73-7.69 (m, 2H), 7.66-7.59 (m, 6H), 7.56-7.50 (m, 11H), 7.44-7.38 (m, 2H), 7.36-7.32 (m, 6H), 7.28-7.25 (m, 3H), 7.19 (d, 1H), 7.12 (d, 1H), 7.08-7.03 (m, 2H), 6.94-6.87 (m, 3H), 6.81 (d, 1H), 6.76-6.73 (m, 2H), 1.69 (s, 6H)

Compound 44: $C_{48}H_{37}NSi$ FAB/MS
Calculated value 655.27, Measured value 655.25
$^1$H NMR (CDCl$_3$, 400 MHz) ☐ 7.67-7.61 (m, 3H), 7.58-7.52 (m, 8H), 7.51-7.45 (m, 2H), 7.39-7.32 (m, 7H), 7.29-7.25 (m, 3H), 7.18 (d, 1H), 7.06-7.01 (m, 5H), 6.92-6.86 (m, 2H), 6.79 (t, 2H), 6.72-6.68 (m, 4H)

Compound 47: $C_{54}H_{39}NSi$ FAB/MS
Calculated value 729.29, Measured value 729.31
$^1$H NMR (CDCl$_3$, 400 MHz) ☐ 8.52 (d, 1H), 8.16 (d, 1H), 8.06-8.02 (m, 2H), 7.99 (d, 1H), 7.90 (d, 1H), 7.75-7.73 (m, 2H), 7.59-7.48 (m, 9H), 7.36-7.32 (m, 6H), 7.27-7.22 (m, 3H), 7.08-7.03 (m, 5H), 6.97-6.93 (m, 2H), 6.82-6.78 (m, 2H), 6.69-6.66 (m, 4H)

Compound 52: $C_{55}H_{48}N_2Si$ FAB/MS
Calculated value 762.34, Measured value 762.33
$^1$H NMR (CDCl$_3$, 400 MHz) ☐ 8.47-8.45 (m, 1H), 7.78-7.76 (m, 2H), 7.62-7.54 (m, 9H), 7.38-7.31 (m, 9H), 7.29-7.24 (m, 4H), 7.16-7.08 (m, 5H), 7.02 (d, 2H), 6.97 (d, 2H), 1.62 (s, 12H)

Compound 54: $C_{44}H_{33}NOSi$ FAB/MS
Calculated value 619.23, Measured value 619.25
$^1$H NMR (CDCl$_3$, 400 MHz) ☐ 7.99 (d, 1H), 7.93 (d, 1H), 7.58-7.57 (m, 1H), 7.55-7.49 (m, 7H), 7.36-7.31 (m, 6H), 7.30-7.24 (m, 5H), 7.09-7.04 (m, 4H), 6.99 (d, 1H), 6.88 (d, 1H), 6.75 (t, 2H), 6.69-6.65 (m, 4H)

Compound 57: $C_{50}H_{38}N_2Si$ FAB/MS
Calculated value 694.28, Measured value 694.27
$^1$H NMR (CDCl$_3$, 400 MHz) ☐ 8.25 (d, 1H), 7.89-7.87 (m, 1H), 7.56-7.50 (m, 7H), 7.42-7.31 (m, 9H), 7.28-7.23 (m, 5H), 7.16-7.11 (m, 2H), 7.09-7.03 (m, 5H), 6.95-6.91 (m, 2H), 6.86-6.82 (m, 2H), 6.75-6.71 (m, 4H)

Compound 58: $C_{48}H_{37}N_3Si$ FAB/MS
Calculated value 695.28, Measured value 695.29
$^1$H NMR (CDCl$_3$, 400 MHz) ☐ 8.62-8.60 (m, 1H), 8.50 (d, 1H), 7.92 (d, 1H), 7.79-7.76 (m, 1H), 7.70 (d, 1H), 7.59-7.48 (m, 8H), 7.43-7.33 (m, 8H), 7.29-7.20 (m, 5H), 7.10-7.04 (m, 5H), 6.95 (d, 1H), 6.90-6.86 (m, 2H), 6.79-6.74 (m, 4H)

Compound 60: $C_{44}H_{33}NSSi$ FAB/MS
Calculated value 635.21, Measured value 635.19
$^1$H NMR (CDCl$_3$, 400 MHz) ☐ 8.17-8.15 (m, 1H), 7.90 (d, 1H), 7.77 (d, 1H), 7.72 (d, 1H), 7.56-7.52 (m, 6H), 7.45 (d, 1H), 7.36-7.32 (m, 6H), 7.28-7.24 (m, 3H), 7.11-7.04 (m, 4H), 6.98 (d, 1H), 6.85 (d, 1H), 6.77 (d, 1H), 6.67-6.63 (m, 2H), 6.55-6.51 (m, 4H)

Compound 62: $C_{50}H_{39}NSi$ FAB/MS
Calculated value 681.29, Measured value 681.32
$^1$H NMR (CDCl$_3$, 400 MHz) ☐ 8.12 (d, 1H), 7.98 (d, 1H), 7.82-7.77 (m, 3H), 7.66 (d, 1H), 7.56-7.52 (m, 6H), 7.48-7.44

(m, 2H), 7.36-7.32 (m, 6H), 7.29-7.24 (m, 4H), 7.19 (d, 2H), 7.08-7.03 (m, 4H), 6.93 (d, 1H), 6.83-6.76 (m, 4H), 6.69-6.65 (m, 4H)

Compound 64: $C_{55}H_{45}NSi$ FAB/MS
Calculated value 747.33, Measured value 747.36
$^1$H NMR (CDCl$_3$, 400 MHz) □ 7.70 (d, 1H), 7.68-7.66 (m, 1H), 7.63 (d, 1H), 7.56-7.52 (m, 6H), 7.50-7.49 (m, 1H), 7.48-7.44 (m, 2H), 7.43-7.39 (m, 2H), 7.36-7.31 (m, 6H), 7.29-7.24 (m, 4H), 7.19 (d, 1H), 7.08-7.03 (m, 5H), 6.96-6.92 (m, 5H), 6.85-6.80 (m, 4H), 1.62 (s, 6H)

Compound 65: $C_{58}H_{47}NSi_2$ FAB/MS
Calculated value 813.32, Measured value 813.30
$^1$H NMR (CDCl$_3$, 400 MHz) □ 7.56-7.54 (m, 6H), 7.53-7.51 (m, 6H), 7.36-7.35 (m, 3H), 7.34-7.33 (m, 6H), 7.32-7.31 (m, 4H), 7.28-7.22 (m, 11H), 7.08-7.01 (m, 4H), 6.96-6.93 (m, 4H), 6.81-6.77 (m, 1H), 6.70-6.66 (m, 2H)

Compound 68: $C_{50}H_{42}N_2Si$ FAB/MS
Calculated value 698.31, Measured value 698.32
$^1$H NMR (CDCl$_3$, 400 MHz) □ 7.73 (d, 2H), 7.70-7.65 (m, 3H), 7.64-7.61 (m, 5H), 7.09-7.02 (m, 10H), 6.98-6.97 (m, 2H), 6.86-6.80 (m, 3H), 6.77-6.73 (m, 4H), 6.67-6.63 (m, 7H), 0.25 (s, 6H)

Compound 70: $C_{66}H_{53}N_3Si$ FAB/MS
Calculated value 915.40, Measured value 915.42
$^1$H NMR (CDCl$_3$, 400 MHz) □ 7.616-7.57 (m, 3H), 7.54-7.52 (m, 2H), 7.44-7.38 (m, 8H), 7.33-7.28 (m, 1H), 7.08-7.04 (m, 10H), 7.03-7.02 (m, 4H), 7.00-6.97 (m, 1H), 6.88-6.83 (m, 6H), 6.79-6.74 (m, 6H), 6.65-6.61 (m, 12H)

Compound 71: $C_{80}H_{64}N_4Si$ FAB/MS
Calculated value 1108.49, Measured value 1108.50
$^1$H NMR (CDCl$_3$, 400 MHz) □ 7.51-7.47 (m, 8H), 7.16-7.14 (m, 2H), 7.12-7.10 (m, 2H), 7.09-7.03 (m, 16H), 6.93-6.90 (m, 10H), 6.87-6.79 (m, 10H), 6.72-6.67 (m, 16H)

Example 1

As an anode, a 15 Ω/cm$^2$ (1200 Å) Corning ITO glass substrate was cut to a size of 50 mm×50 mm×0.7 mm, washed with ultrasonic waves in isopropyl alcohol and pure water for 5 minutes each, and then cleaned with UV and ozone for 30 minutes. The ITO glass substrate was mounted on a vacuum depositor.

2-TNATA was deposited on the ITO glass substrate to form a HIL having a thickness of 600 Å, and Compound 11 was then vacuum-deposited on the HIL to form a HTL having a thickness of 300 Å. 9,10-di(naphthalene-2-yl)anthracene (ADN) as a blue fluorescent host and 4,4'-bis(2-(4-(N,N-diphenylamino)phenyl)vinyl)biphenyl (DPAVBi) as a blue fluorescent dopant were co-deposited on the HTL at a weight ratio of 98:2 to form an EML having a thickness of 300 Å. Then, Alq$_3$ was deposited on the EML to form an ETL having a thickness of 300 Å, LiF (a halogenated alkali metal) was deposited on the ETL to form an EIL having a thickness of 10 Å, and Al was vacuum-deposited on the EIL to form a second electrode (cathode) having a thickness of 3,000 Å (a LiF/Al electrode). thereby completing the manufacture of an OED.

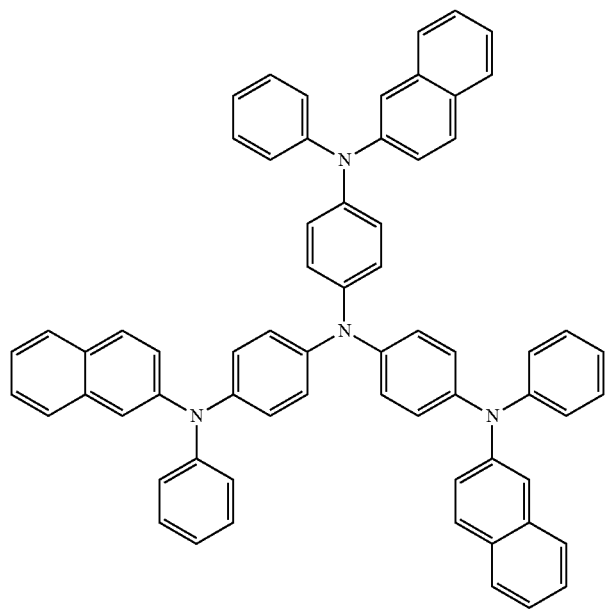

2-TNATA

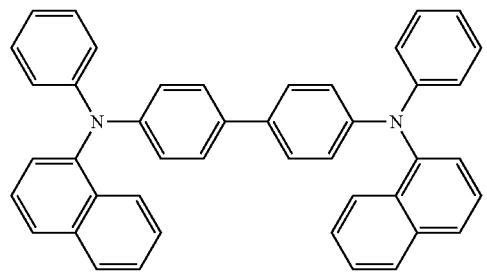

NPB

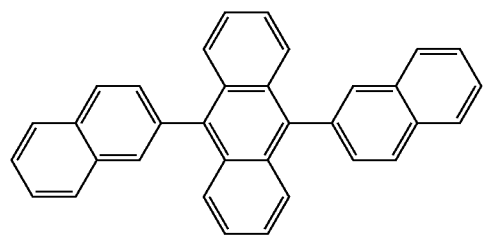

DNA

-continued

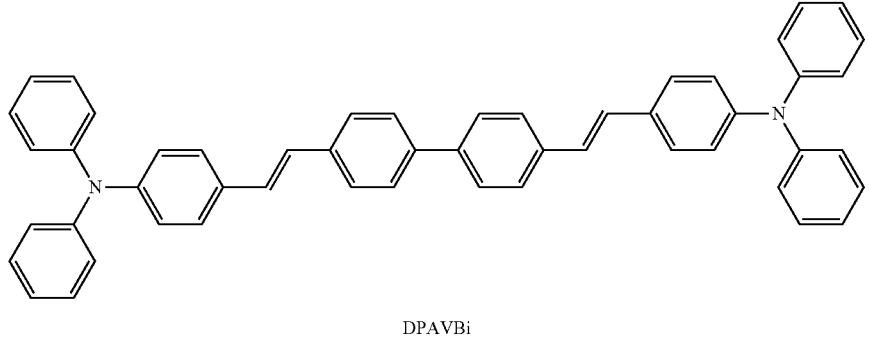

DPAVBi

The OLED had a current density of 50 mA/cm$^2$, a driving voltage of 6.19 V, a high brightness of 2,245 cd/M, a light-emission efficiency of 4.49 cd/A, and a half-life of 253 hours at 100 mA/cm$^2$.

Example 2

An OLED was prepared in the same manner as in Example 1, except that Compound 12 was used instead of Compound 11 to form the HTL.

The OLED had a current density of 50 mA/cm$^2$, a driving voltage of 6.33 V, a high brightness of 2,107 cd/m$^2$, a light-emission efficiency of 4.21 cd/A, and a half-life of 210 hours at 100 mA/cm$^2$.

Example 3

An OLED was prepared in the same manner as in Example 1, except that Compound 17 was used instead of Compound 11 to form the HTL.

The OLED had a current density of 50 mA/cm$^2$, a driving voltage of 6.15 V, a high brightness of 2,263 cd/m$^2$, a light-emission efficiency of 4.53 cd/A, and a half-life of 240 hours at 100 mA/cm$^2$.

Example 4

An OLED was prepared in the same manner as in Example 1, except that Compound 68 was used instead of Compound 11 to form the HTL.

The OLED had a current density of 50 mA/cm$^2$, a driving voltage of 6.26 V, a high brightness of 2,197 cd/m$^2$, a light-emission efficiency of 4.39 cd/A, and a half-life of 166 hours at 100 mA/cm$^2$.

Example 5

An OLED was prepared in the same manner as in Example 1, except that Compound 70 was used instead of Compound 11 to form the HTL.

The OLED had a current density of 50 mA/cm$^2$, a driving voltage of 6.56 V, a high brightness of 2,086 cd/m$^2$, a light-emission efficiency of 4.17 cd/A, and a half-life of 153 hours at 100 mA/cm$^2$.

Example 6

As an anode, a 15 Ω/cm$^2$ (1200 Å) Corning ITO glass substrate was cut to a size of 50 mm×50 mm×0.7 mm, washed with ultrasonic waves in isopropyl alcohol and pure water for 5 minutes each, and then cleaned with UV and ozone for 30 minutes. The ITO glass substrate was mounted on a vacuum depositor.

2-TNATA was deposited on the ITO glass substrate to form a HIL having a thickness of 600 Å, and 4,4'-bis[N-(1-naphthyl)-N-phenylamino]biphenyl (NPB) was vacuum-deposited on the HIL to form a HTL having a thickness of 300 Å. 9,10-di-naphthalene-2-yl-anthracene (ADN) as a blue fluorescent host and Compound 11 as a blue fluorescent dopant were co-deposited on the HTL at a weight ratio of 98:2 to form an EML having a thickness of 300 Å. Then, Alq$_3$ was deposited on the EML to form an ETL having a thickness of 300 Å, LiF (a halogenated alkali metal) was deposited on the ETL to form an EIL having a thickness of 10 Å, and Al was vacuum-deposited on the EIL to form a second electrode (cathode) having a thickness of 3,000 Å (a LiF/Al electrode), thereby completing the manufacture of an OLED.

The OLED had a current density of 50 mA/cm$^2$, a driving voltage of 7.06 V, a high brightness of 2,524 cd/m$^2$, a light-emission efficiency of 5.04 cd/A, and a half-life of 162 hours at 100 mA/cm$^2$.

Example 7

An OLED was prepared in the same manner as in Example 6, except that Compound 37 was used instead of Compound 11 to form the EML.

The OLED had a current density of 50 mA/cm$^2$, a driving voltage of 7.13 V, a high brightness of 3,312 cd/m$^2$, a light-emission efficiency of 6.62 cd/A, and a half-life of 177 hours at 100 mA/cm$^2$.

Example 8

An OLED was prepared in the same manner as in Example 6, except that Compound 39 was used instead of Compound 11 to form the EML.

The OLED had a current density of 50 mA/cm$^2$, a driving voltage of 7.29V, a high brightness of 3,382 cd/m$^2$, a light-emission efficiency of 6.76 cd/A, and a half-life of 173 hours at 100 mA/cm$^2$.

Example 9

An OLED was prepared in the same manner as in Example 6, except that Compound 47 was used instead of Compound 11 to form the EML.

The OLED had a current density of 50 mA/cm², a driving voltage of 7.28 V, a high brightness of 3,526 cd/m², a light-emission efficiency of 7.04 cd/A, and a half-life of 181 hours at 100 mA/cm².

Example 10

An OLED was prepared in the same manner as in Example 6, except that Compound 64 was used instead of Compound 11 to form the EML.

The OLED had a current density of 50 mA/cm², a driving voltage of 7.25 V, a high brightness of 3,464 cd/m², a light-emission efficiency of 6.93 cd/A, and a half-life of 205 hours at 100 mA/cm².

Example 11

An OLED was prepared in the same manner as in Example 1 or 6, except that Compound 17 was used instead of NPB to form the HTL, and Compound 47 was used instead of DPAVBi to form the EML.

The OLED had a current density of 50 mA/cm², a driving voltage of 6.11V, a high brightness of 3,608 cd/m², a light-emission efficiency of 7.22 cd/A, and a half-life of 356 at 100 mA/cm².

Example 12

An OLED was prepared in the same manner as in Example 1 or 6, except that Compound 17 was used instead of NPB to form the HTL and Compound 64 was used instead of DPAVBi to form the EML.

The OLED had a current density of 50 mA/cm², a driving voltage of 6.13V, a high brightness of 3,634 cd/m², a light-emission efficiency of 7.27 cd/A, and a half-life of 341 hours at 100 mA/cm².

Comparative Example 1

An OLED was prepared in the same manner as in Example 1, except that 4,4'-bis[N-(1-naphthyl)-N-phenylamino]biphenyl (NPB) was used instead of Compound 11 to form the HTL.

The OLED had a current density of 50 mA/cm², a driving voltage of 7.35V, a high brightness of 2,065 cd/m², a light-emission efficiency of 4.13 cd/A, and a half-life of 145 hours at 100 mA/cm².

When Compound 1 according to an embodiment of the present invention is used to form the HTL, similar or improved I-V-L characteristics compared to when NPB is used to form the HTL can be achieved, and in particular the HTL with Compound I may yield significantly increased lifetime. The I-V-L and lifetime characteristics of the OLEDs of Examples 1 through 5 and Comparative Example 1 are shown in Table 1 below.

TABLE 1

| | Hole transport material | Driving voltage (V) | Current density (mA/cm²) | Brightness (cd/m²) | Efficiency (cd/A) | Emission color | Half life (hr @ 100 mA/cm²) |
|---|---|---|---|---|---|---|---|
| Example 1 | Compound 11 | 6.19 | 50 | 2,245 | 4.49 | Blue | 253 hr |
| Example 2 | Compound 12 | 6.33 | 50 | 2,107 | 4.21 | Blue | 210 hr |
| Example 3 | Compound 17 | 6.15 | 50 | 2,263 | 4.53 | Blue | 240 hr |
| Example 4 | Compound 68 | 6.26 | 50 | 2,197 | 4.39 | Blue | 166 hr |
| Example 5 | Compound 70 | 6.56 | 50 | 2,086 | 4.17 | Blue | 153 hr |
| Comparative Example 1 | NPB | 7.35 | 50 | 2,065 | 4.13 | Blue | 145 hr |

In addition, it may be confirmed that when the compounds represented by Formula 1 are used as the dopant in the EML, the resulting OLEDs have increased efficiency and lifetime compared to OLEDs in which DPAVBi is used as the blue fluorescent dopant. Furthermore, in Examples 11 and 12, in which the compounds of Formula 1 are used to form both the HTL and the EML, the resulting OLEDs may have improved driving voltage and increased lifetimes. The I-V-L and lifetime characteristics of the OLEDs of Examples 6 through 12 and Comparative Example 1 are shown in Tables 2 and 3 below.

TABLE 2

| | Emission material | Driving voltage (V) | Current density (mA/cm²) | Brightness (cd/m²) | Efficiency (cd/A) | Emission color | Half life (hr @ 100 mA/cm²) |
|---|---|---|---|---|---|---|---|
| Example 6 | Compound 11 | 7.06 | 50 | 2,524 | 5.04 | Blue | 162 hr |
| Example 7 | Compound 37 | 7.13 | 50 | 3,312 | 6.62 | Blue | 177 hr |
| Example 8 | Compound 39 | 7.29 | 50 | 3,382 | 6.76 | Blue | 173 hr |
| Example 9 | Compound 47 | 7.28 | 50 | 3,526 | 7.04 | Blue | 181 hr |
| Example 10 | Compound 64 | 7.25 | 50 | 3,464 | 6.93 | Blue | 205 hr |
| Comparative Example 1 | DPAVBi | 7.35 | 50 | 2,065 | 4.13 | Blue | 145 hr |

TABLE 3

| | Hole transport material/ emission material | Driving voltage (V) | Current density (mA/cm$^2$) | Brightness (cd/m$^2$) | Efficiency (cd/A) | Emission color | Half life (hr @ 100 mA/cm$^2$) |
|---|---|---|---|---|---|---|---|
| Example 11 | Compound 17/ Compound 47 | 6.11 | 50 | 3,608 | 7.22 | Blue | 356 hr |
| Example 12 | Compound 17/ Compound 64 | 6.13 | 50 | 3,634 | 7.27 | Blue | 341 hr |
| Example 1 | NPB/DPAVBi | 7.35 | 50 | 2,065 | 4.13 | Blue | 145 hr |

As described above, the novel vinylsilane compounds according to one or more embodiments of the present invention have good emission characteristics and charge transporting capabilities, and thus may be used as the electron injecting/transporting material for most color fluorescent and phosphorescent devices, such as red, green, blue, and white fluorescent and phosphorescent devices, and may be used as the light-emitting material for green, blue, or white fluorescent devices. Thus, organic light-emitting devices with high-efficiency, low-driving voltage, high luminance and long lifespans may be manufactured using the vinylsilane compounds.

While the present invention has been illustrated and described with reference to certain exemplary embodiments, it will be understood by those of ordinary skill in the art that various changes can be made to the described embodiments without departing from the spirit and scope of the present invention as defined by the following claims.

What is claimed is:
1. A vinylsilane compound represented by Formula 1:

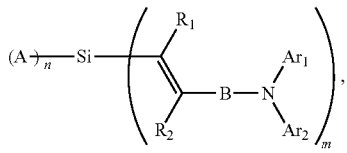

Formula 1 wherein:
each A is independently:
   a substituted or unsubstituted $C_1$-$C_{60}$ alkyl group,
   an unsubstituted $C_5$-$C_{60}$ aryl group,
   a $C_5$-$C_{60}$ aryl group in which at least one hydrogen atom is substituted with a heavy hydrogen atom, a halogen atom, a hydroxyl group, a nitro group, a cyano group, an amino group, an amidino group, a hydrazine, a hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group, or
   a substituted or unsubstituted $C_3$-$C_{60}$ heteroaryl group,
each of $R_1$ and $R_2$ is independently a hydrogen atom, a deuterium atom, a substituted or unsubstituted $C_1$-$C_{60}$ alkyl group, a substituted or unsubstituted $C_3$-$C_{60}$ cycloalkyl group, or a substituted or unsubstituted $C_3$-$C_{60}$ heteroaryl group,
B is a bivalent linker and is a substituted or unsubstituted $C_1$-$C_{60}$ alkylene group, a substituted or unsubstituted $C_5$-$C_{60}$ arylene group, or a substituted or unsubstituted $C_3$-$C_{60}$ heteroarylene group, $Ar_1$ and $Ar_2$ are optionally linked to form a

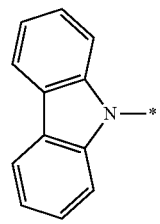 [SMILES: *n1c2ccccc2c2ccccc21]

ring with the N atom of Formula 1, or each of $Ar_1$ and $Ar_2$ is independently a group represented by any one of Formulae 3a, 3b and 3d through 3f:

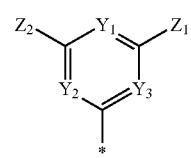

3a

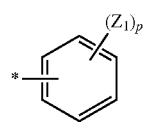

3b

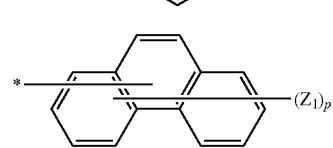

3d

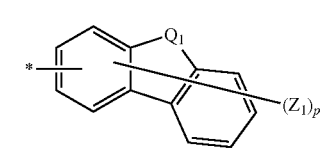

3e

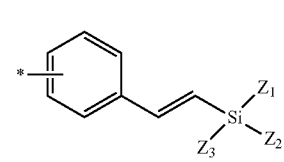

3f

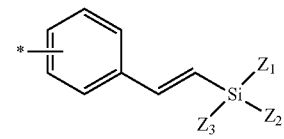

wherein, in Formulae 3a, 3b and 3d through 3f,
$Q_1$ is a linker represented by —C($R_{30}$)($R_{31}$)—, —N($R_{32}$)—, —S—, or —O—;
each of $Y_1$, $Y_2$, and $Y_3$ is a linker independently represented by —O—, —N=, —N($R_{20}$)—, or —C($R_{21}$)=;
each of $Z_1$, $Z_2$, $Z_3$, $R_{20}$, $R_{21}$, $R_{30}$, $R_{31}$, and $R_{32}$ is independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;

p is an integer from 1 to 12; and

*indicates a binding site, n is an integer from 0 to 3, m is an integer from 1 to 4, and n + m = 4.

2. The vinylsilane compound of claim 1, wherein:

each A is independently:
- a substituted or unsubstituted $C_1$-$C_{30}$ alkyl group,
- an unsubstituted $C_5$-$C_{30}$ aryl group,
- a $C_5$-$C_{30}$ aryl group in which at least one hydrogen atom is substituted with a heavy hydrogen atom, a halogen atom, a hydroxyl group, a nitro group, a cyano group, an amino group, an amidino group, a hydrazine, a hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group, or
- a substituted or unsubstituted $C_3$-$C_{30}$ heteroaryl group, each of $R_1$ and $R_2$ is independently a hydrogen atom, a deuterium atom, a substituted or unsubstituted $C_1$-$C_{30}$ alkyl group, a substituted or unsubstituted $C_3$-$C_{30}$ cycloalkyl group, or a substituted or unsubstituted $C_3$-$C_{30}$ heteroaryl group, and B is a substituted or unsubstituted $C_5$-$C_{30}$ arylene group or a substituted or unsubstituted $C_3$-$C_{30}$ heteroarylene group.

3. The vinylsilane compound of claim 1, wherein, each of $R_1$ and $R_2$ is independently a hydrogen atom or a deuterium atom.

4. A vinylsilane compound represented by Formula 1:

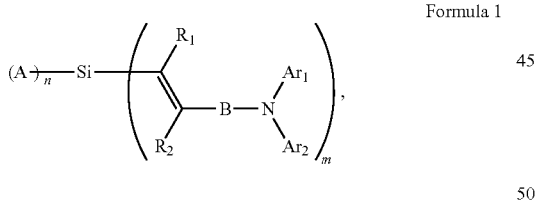

Formula 1 wherein:

each A is independently a substituted or unsubstituted $C_1$-$C_{20}$ alkyl group, or any one of Formulae 2a through 2d:

2a

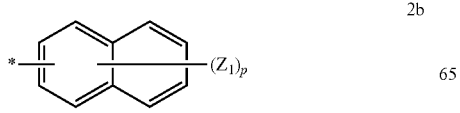

2b

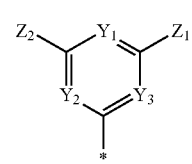

2c

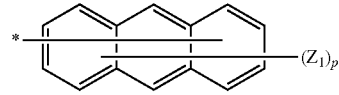

2d wherein, in Formulae 2a through 2d:

each of $Y_1$, $Y_2$, and $Y_3$ is a linker independently represented by —N=, —N($R_{20}$)—, or —C($R_{21}$)=;

each of $Z_2$, $R_{20}$, and $R_{21}$ is independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;

$Z_1$ is:
- a hydrogen atom,
- a deuterium atom,
- a substituted or unsubstituted $C_1$-$C_{20}$ alkyl group,
- an unsubstituted $C_5$-$C_{20}$ aryl group,
- a $C_5$-$C_{30}$ aryl group in which at least one hydrogen atom is substituted with a heavy hydrogen atom, a halogen atom, a hydroxyl group, a nitro group, a cyano group, an amino group, an amidino group, a hydrazine, a hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group,
- a substituted or unsubstituted $C_3$-$C_{20}$ heteroaryl group,
- a substituted or unsubstituted $C_6$-$C_{20}$ condensed polycyclic group,
- a halogen atom,
- a cyano group,
- a nitro group,
- a hydroxyl group, or
- a carboxyl group;

p is an integer from 1 to 12; and

* is a binding site;

each of $R_1$ and $R_7$ is independently a hydrogen atom, a deuterium atom, a substituted or unsubstituted $C_1$-$C_{60}$ alkyl group a substituted or unsubstituted $C_3$-$C_{60}$ cycloalkyl group, or a substituted or unsubstituted $C_3$-$C_{60}$ heteroaryl group, B is a bivalent linker and is a substituted or unsubstituted $C_1$-$C_{60}$ alkylene group, a substituted or unsubstituted $C_5$-$C_{60}$ arylene group, or a substituted or unsubstituted $C_3$-$C_{60}$ heteroarylene group, $Ar_1$ and $Ar_2$ are optionally linked to form a

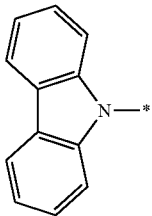 [SMILES: *n1c2ccccc2c2ccccc21]

ring with the N atom of Formula 1, or each of $Ar_1$ and $Ar_2$ is independently a group represented by any one of Formulae 3a, 3b and 3d through 3f:

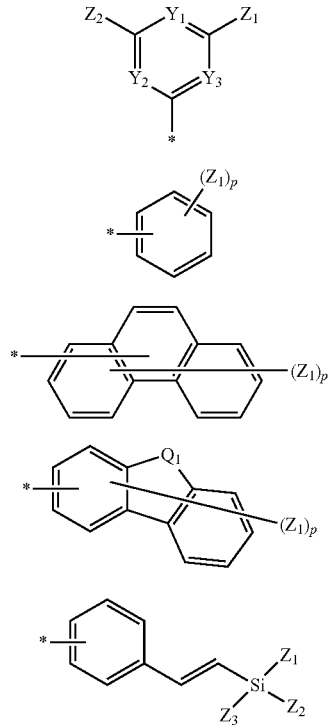

wherein, in Formulae 3a, 3b and 3d through 3f,
$Q_1$ is a linker represented by —$C(R_{30})(R_{31})$—, —$N(R_{32})$—, —S—, or —O—;
each of $Y_1$, $Y_2$, and $Y_3$ is a linker independently represented by —O—, —N═, —$N(R_{20})$—, or —$C(R_{21})$═;
each of $Z_1$, $Z_2$, $Z_3$, $R_{20}$, $R_{21}$, $R_{30}$, $R_{31}$, and $R_{32}$ is independently a hydrogen atom a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;
p is an integer from 1 to 12; and
* indicates a binding site,
n is an integer from 0 to 3,
m is an integer from 1 to 4, and
n+m=4.

5. The vinylsilane compound of claim 1, wherein each of $Ar_1$ and $Ar_2$ is independently a compound represented by any one of Formulae 3a, 3b and 3d through 3f:

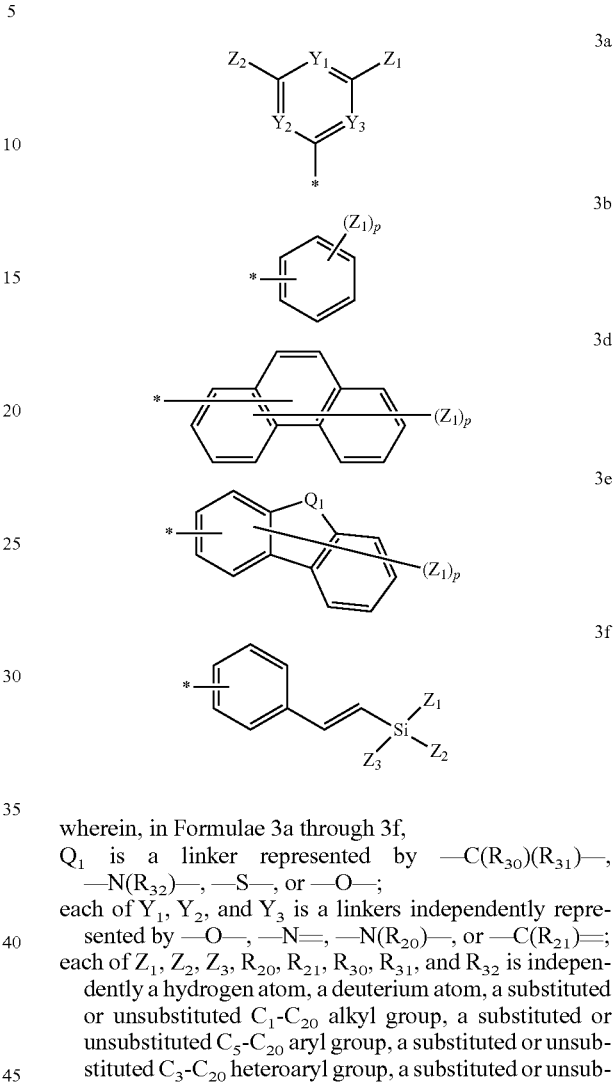

wherein, in Formulae 3a through 3f,
$Q_1$ is a linker represented by —$C(R_{30})(R_{31})$—, —$N(R_{32})$—, —S—, or —O—;
each of $Y_1$, $Y_2$, and $Y_3$ is a linkers independently represented by —O—, —N═, —$N(R_{20})$—, or —$C(R_{21})$═;
each of $Z_1$, $Z_2$, $Z_3$, $R_{20}$, $R_{21}$, $R_{30}$, $R_{31}$, and $R_{32}$ is independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;
p is an integer from 1 to 12; and
* indicates a binding site.

6. The vinylsilane compound of claim 1, wherein B is a linker represented by any one of Formulae 4a to 4i, or a linker obtained by linking two or more compounds represented by Formulae 4a to 4i:

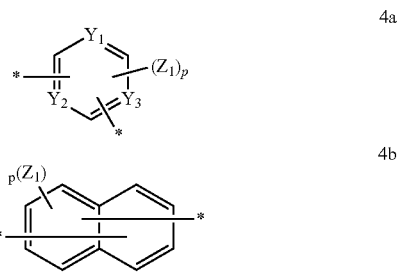

-continued

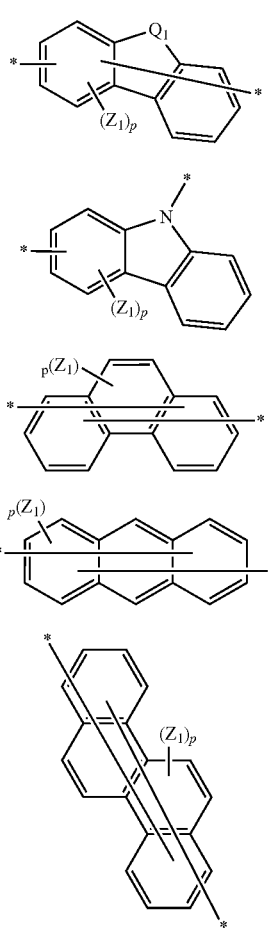

4c
4d
4e
4f
4g

-continued

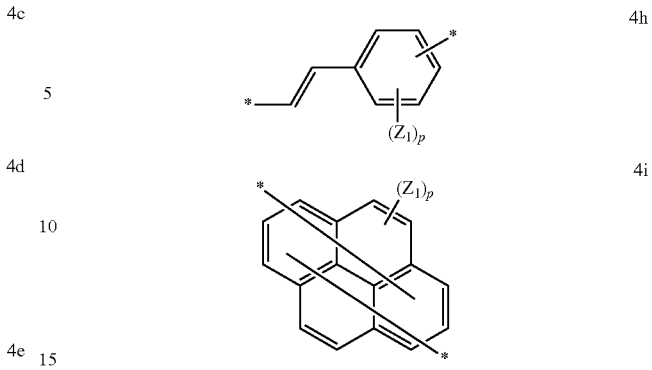

4h
4i wherein, in Formulae 4a through 4i, $Q_1$ is a linker represented by —C($R_{30}$)($R_{31}$)—, —N($R_{32}$)—, —S—, or —O—;

each of $Y_1, Y_2,$ and $Y_3$ is a linker independently represented by —O—, —N=, —N($R_{20}$)—, or —C($R_{21}$)=;

each of $Z_1, R_{20}, R_{21}, R_{30}, R_{31},$ and $R_{32}$ is independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;

p is an integer from 1 to 12; and

* indicates a binding site.

7. A vinylsilane compound represented by one of the formulae below:

1

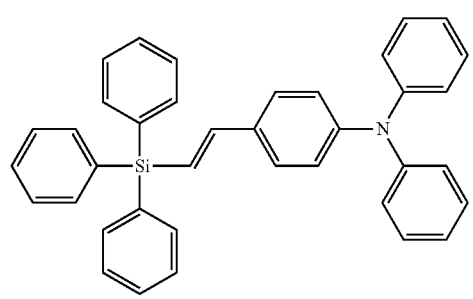

2

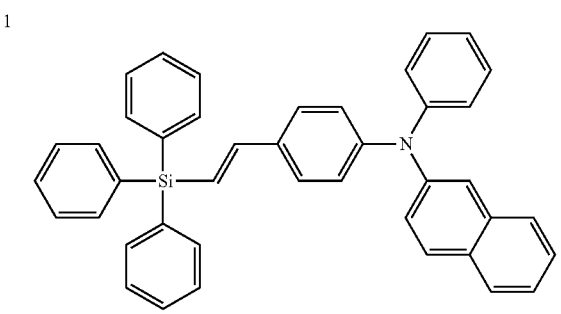

3

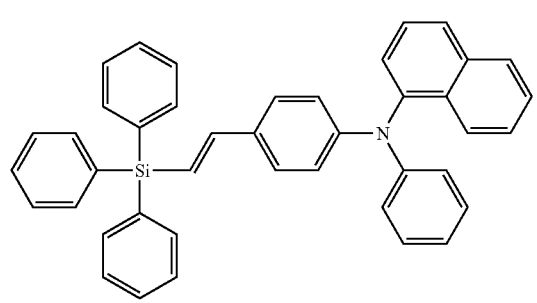

4

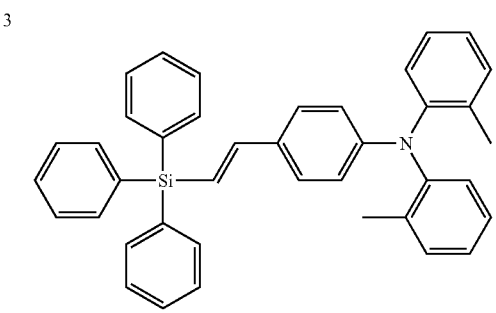

-continued
5
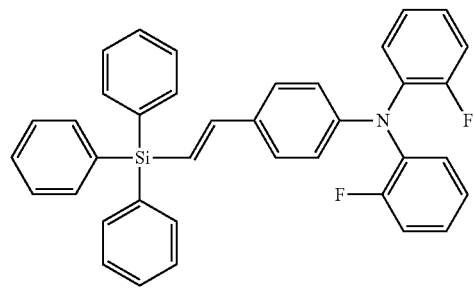
6
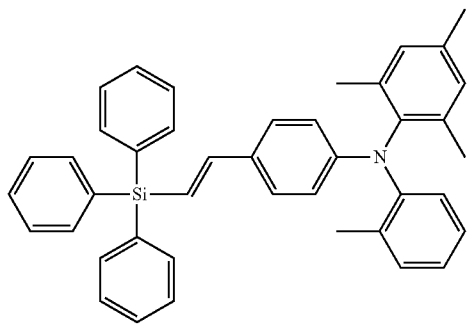
7
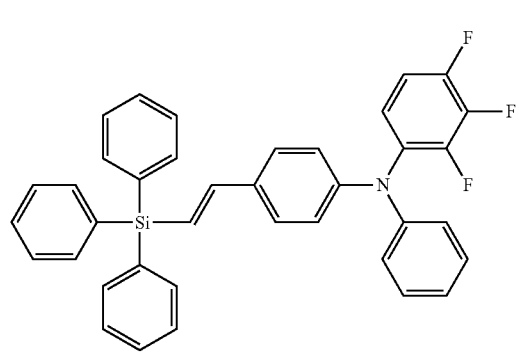
8
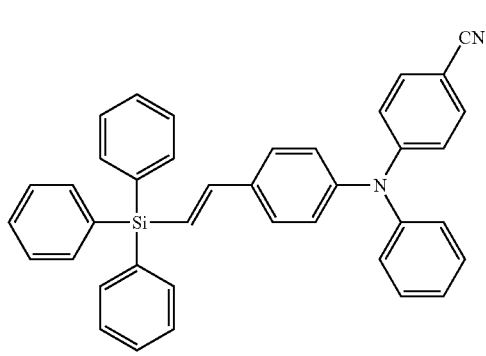
10
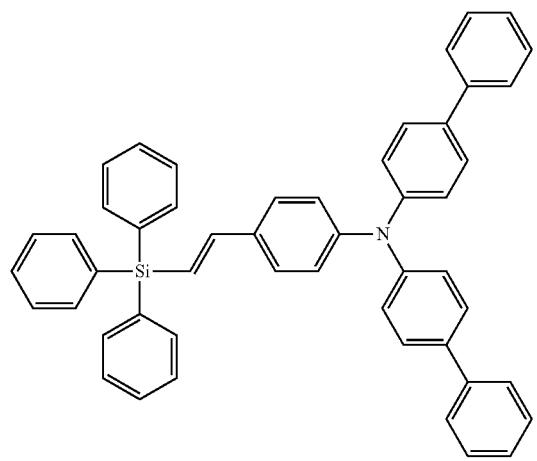
11
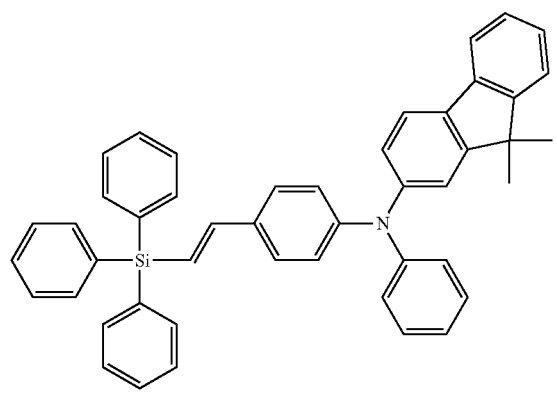
12
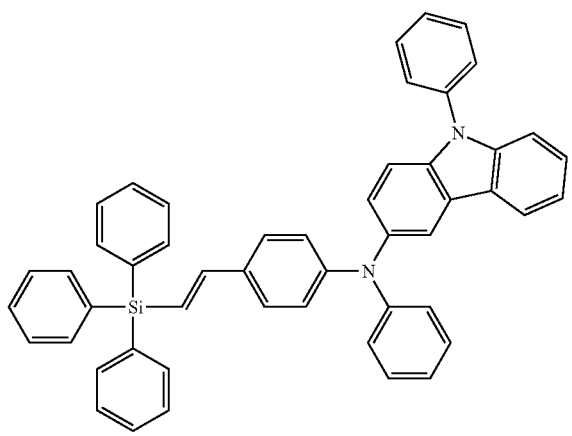

-continued
13
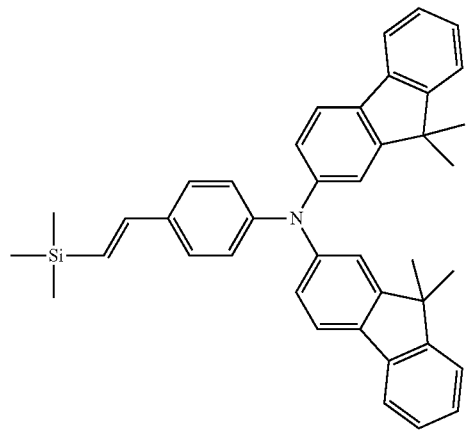
14
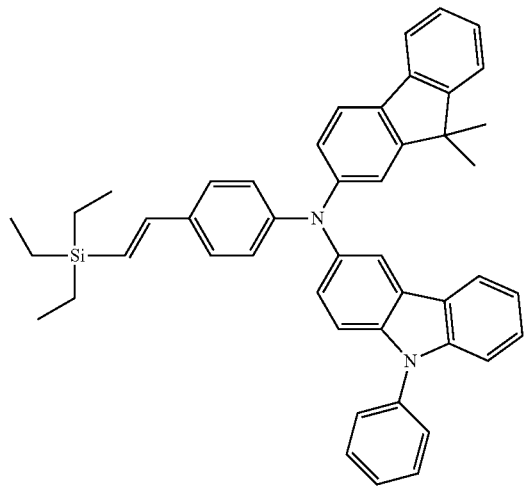
15
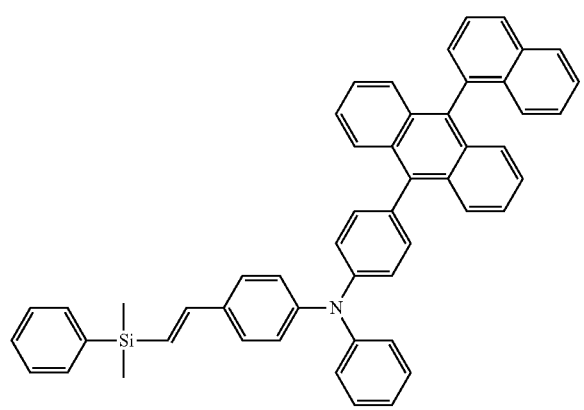
16
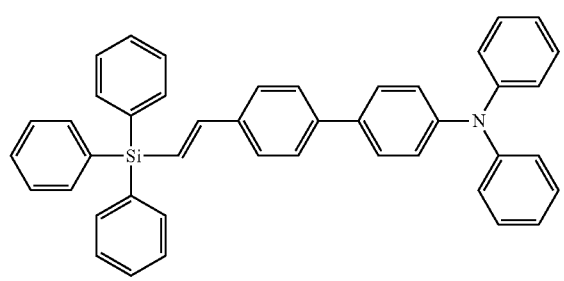
17
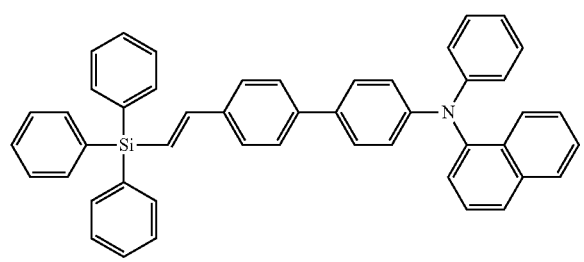
18
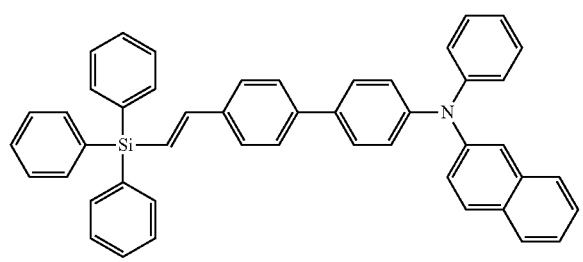
19
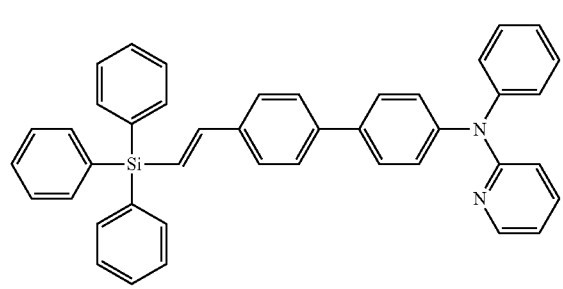
20
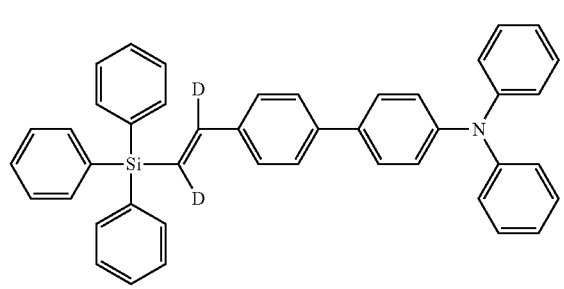

-continued
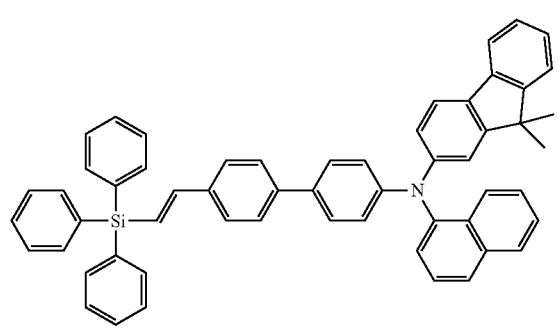
21
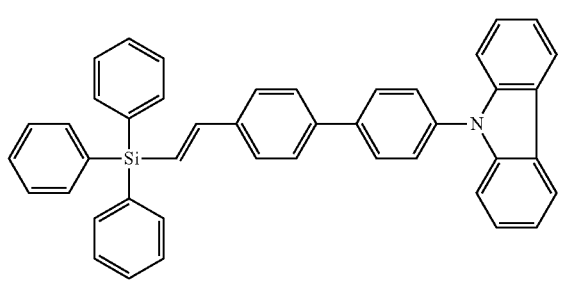
22
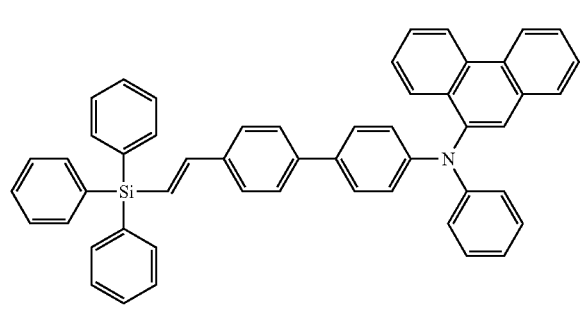
23
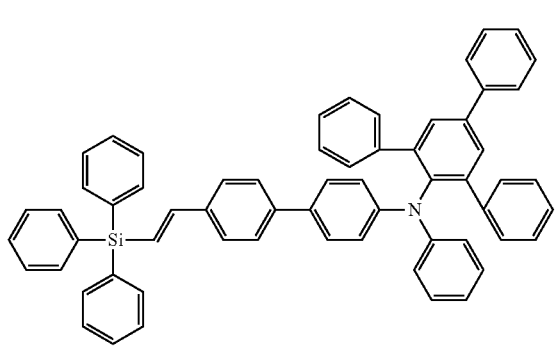
24
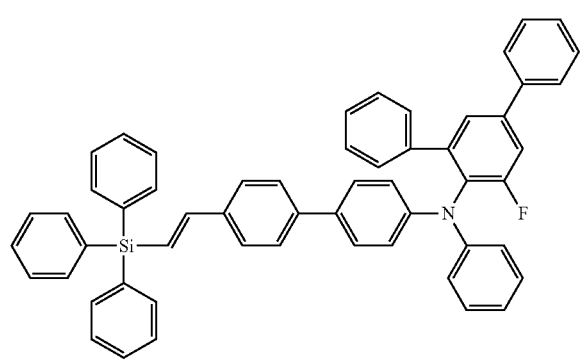
25
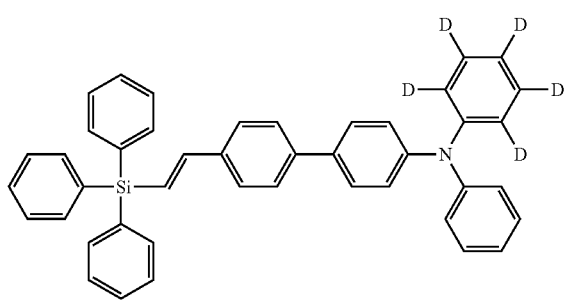
26
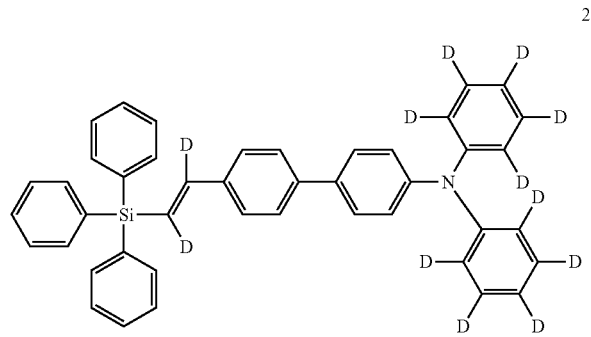
27
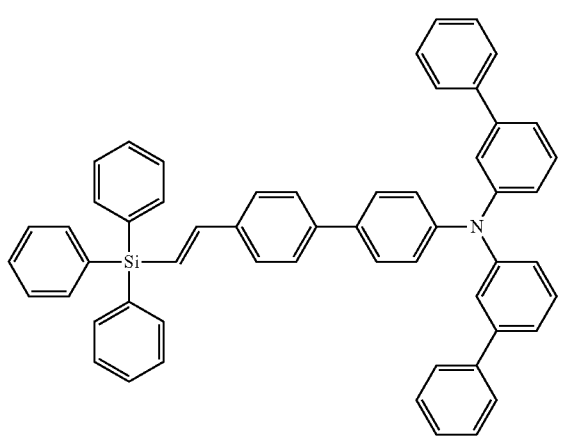
28

-continued
29
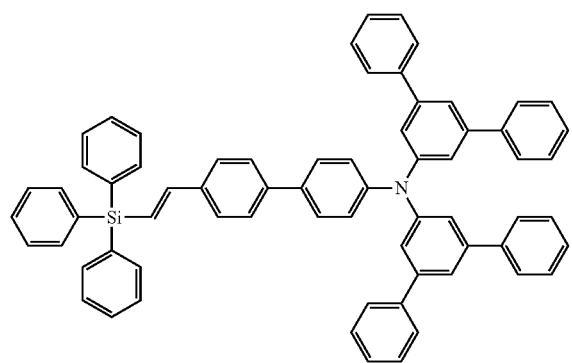
30
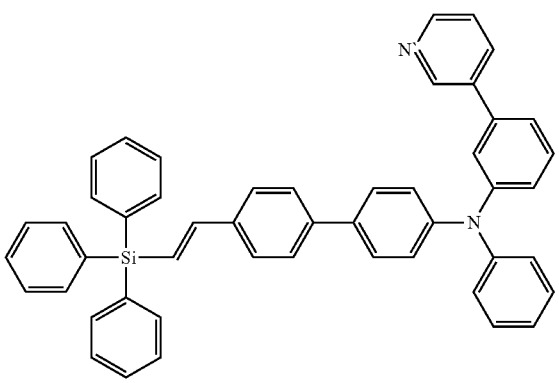
31
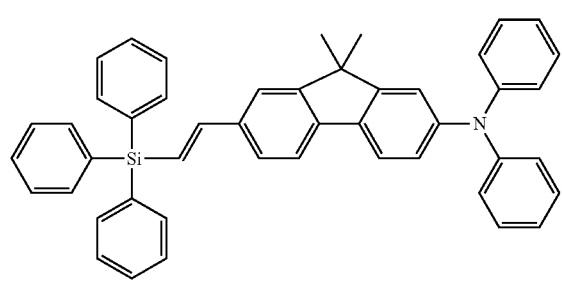
32
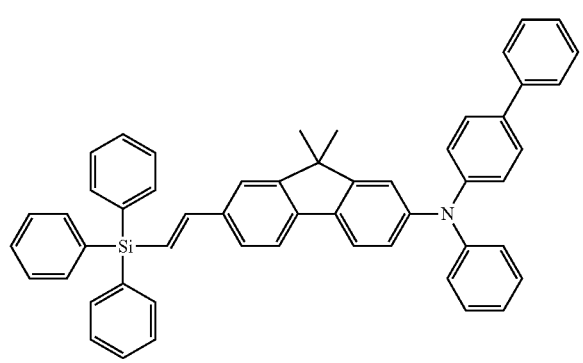
33
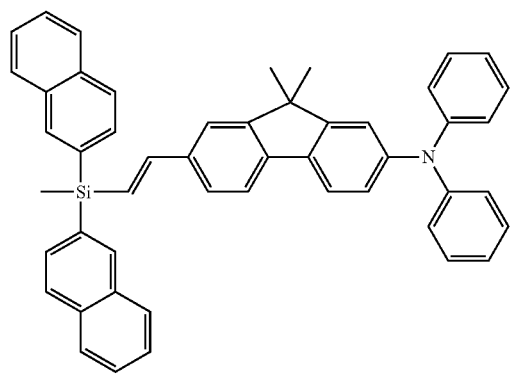
34
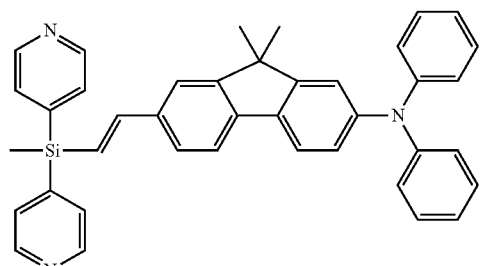
35
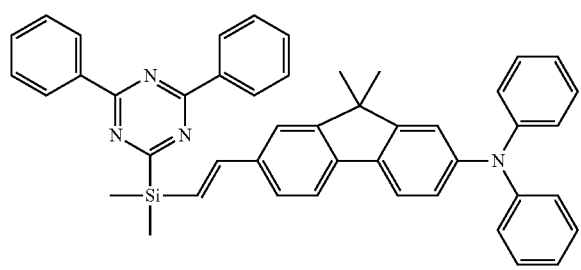
36
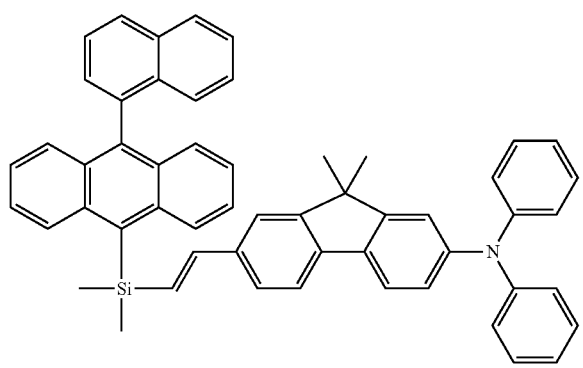

-continued
37
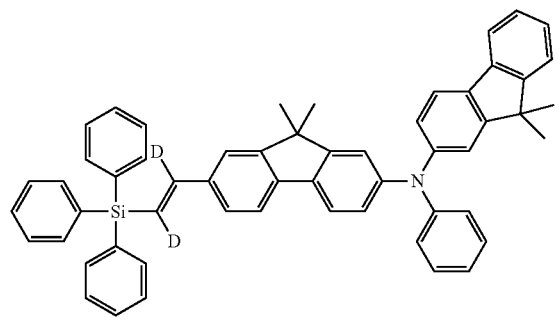
38
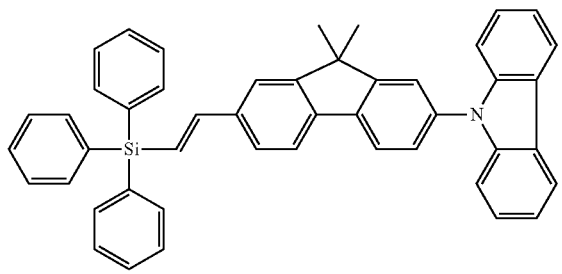
39
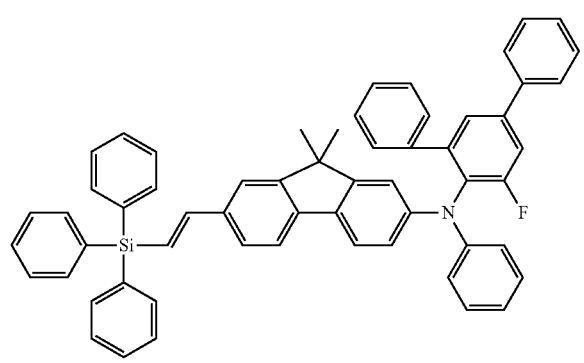
40
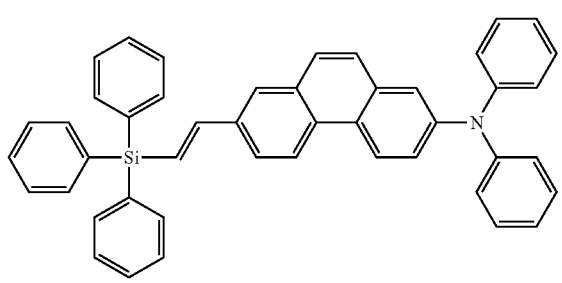
41
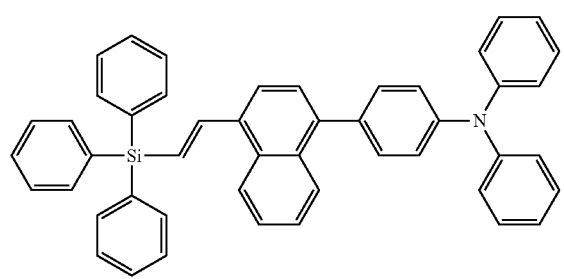
42
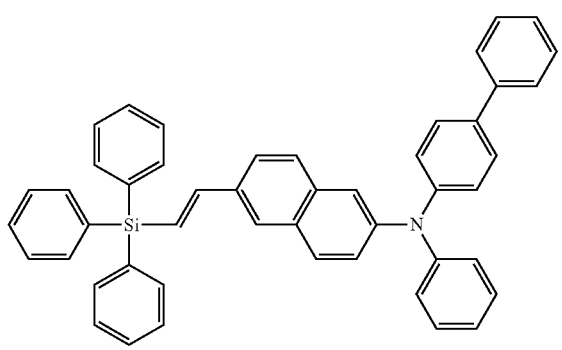
43
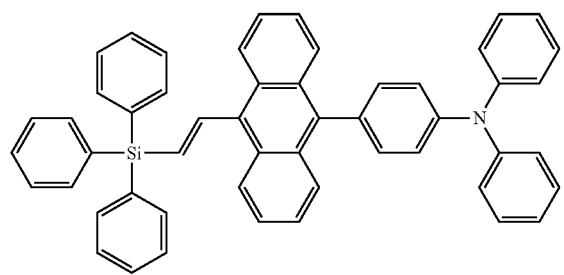
44
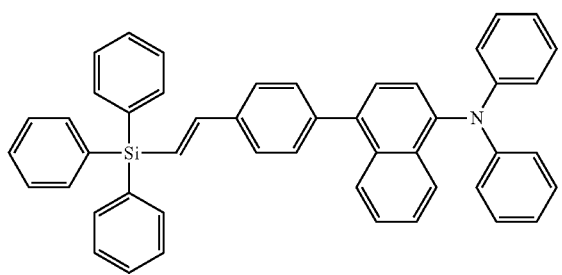
45
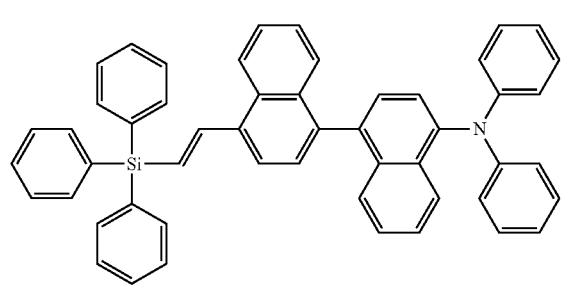
46
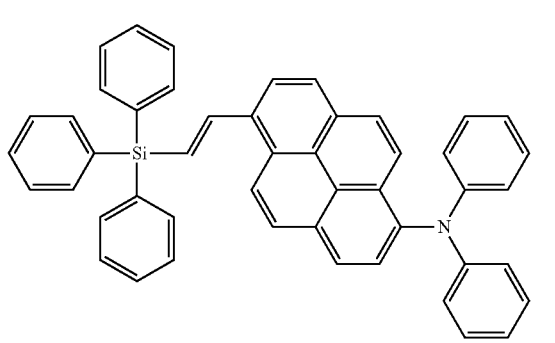

-continued
47
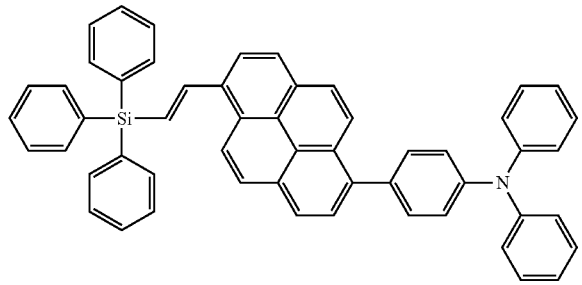
48
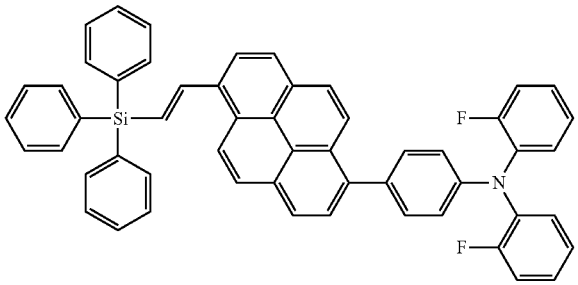
49
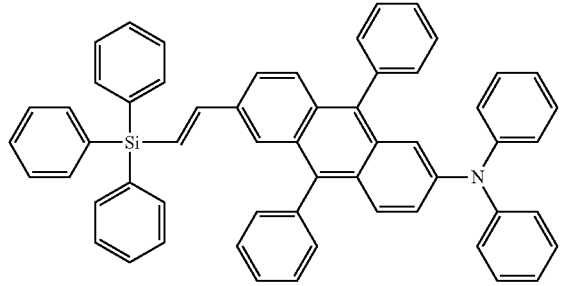
50
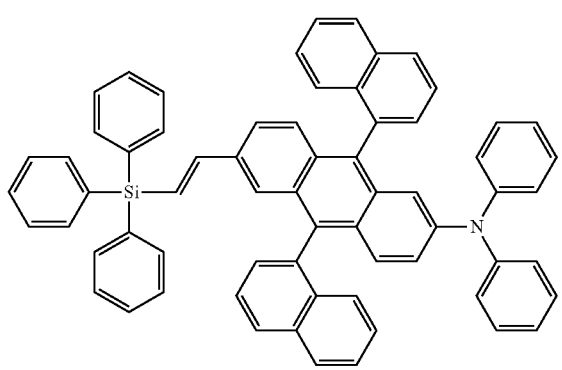
51
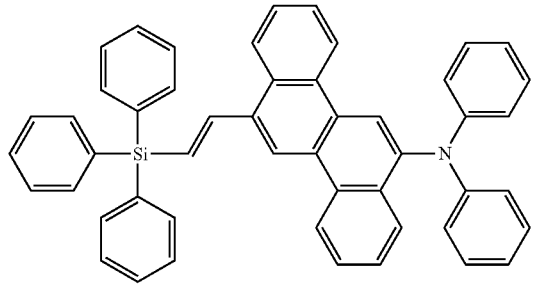
52
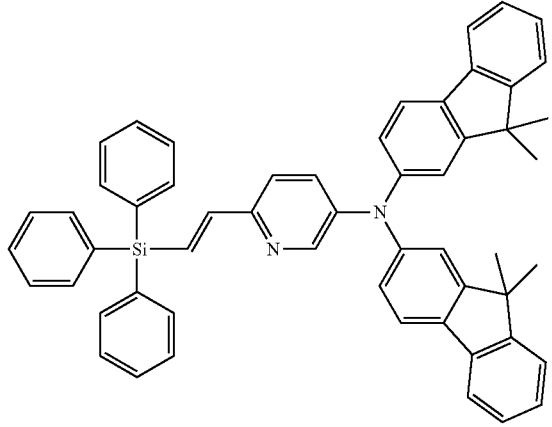
53
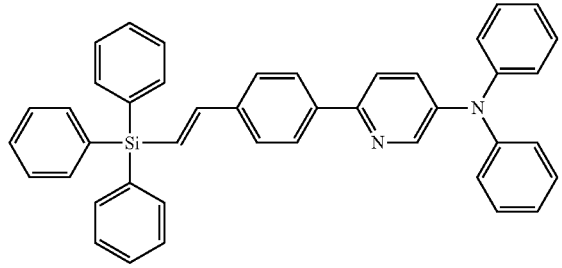
54
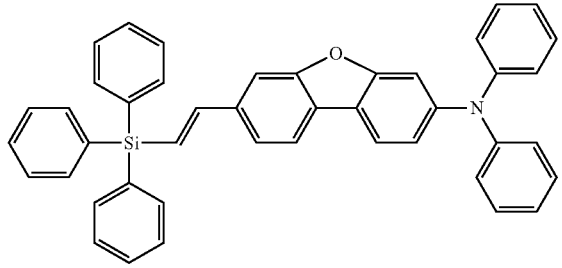

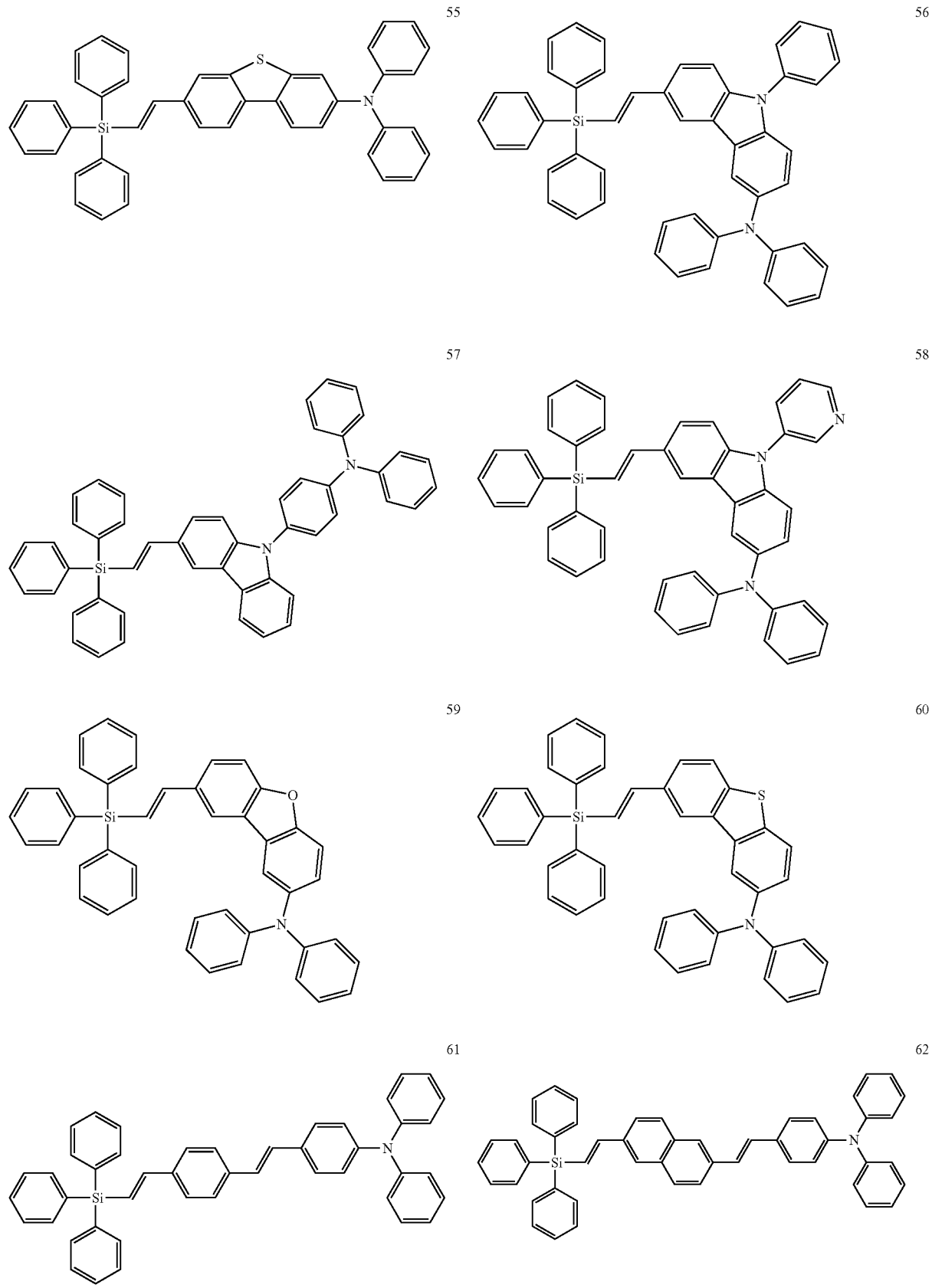

63
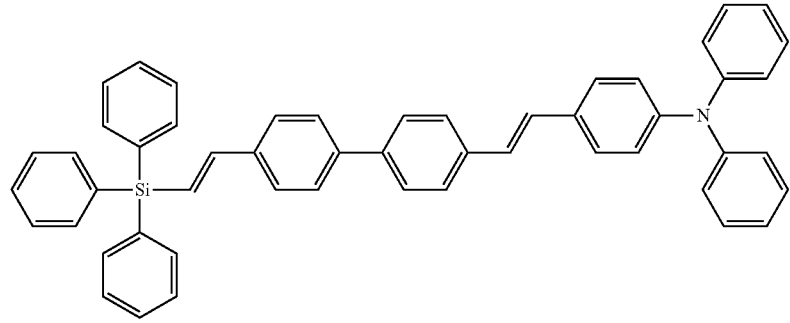
64
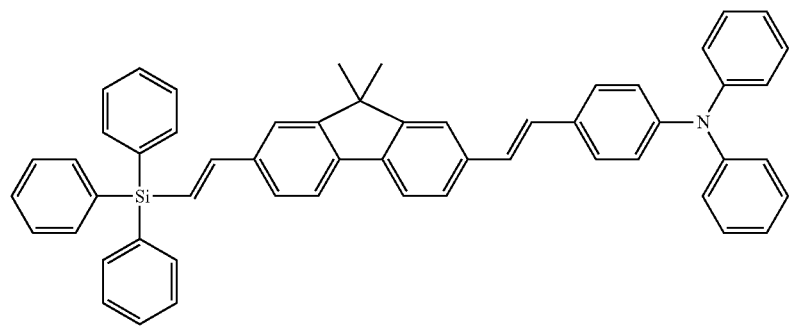
65
66
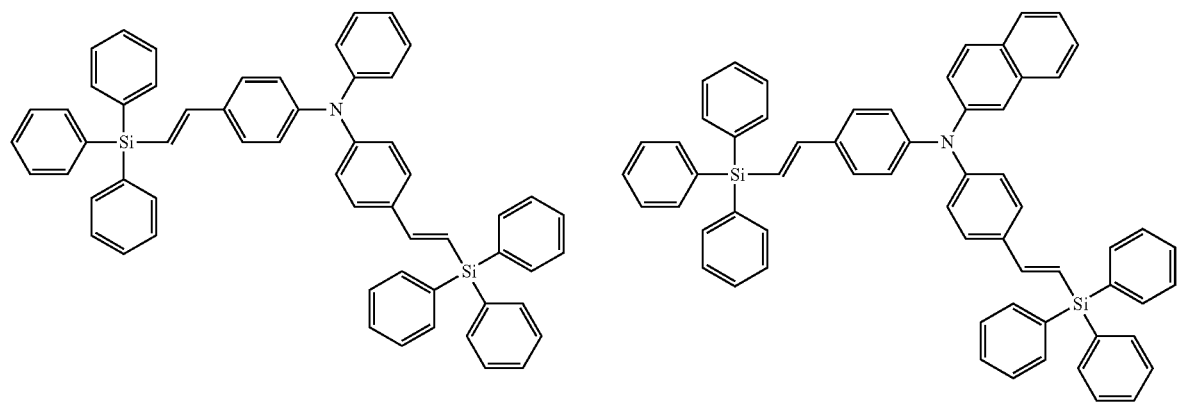
67
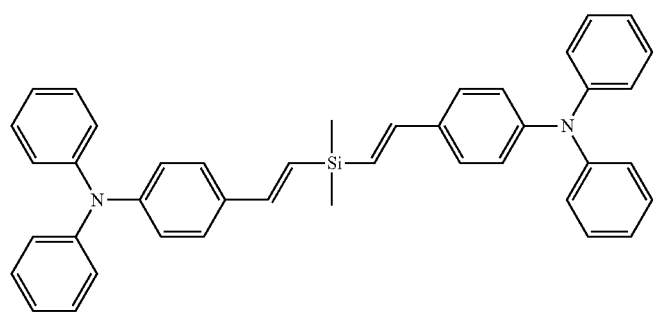
68
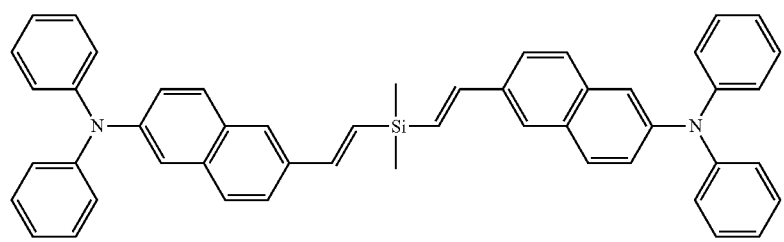

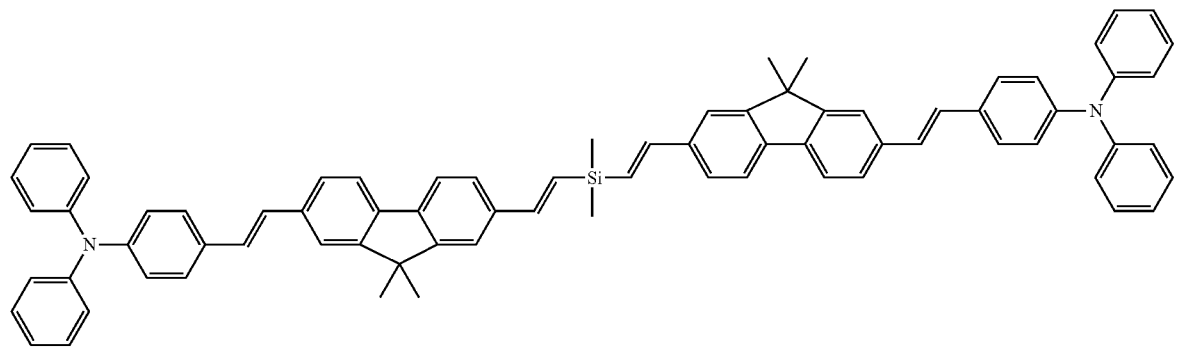

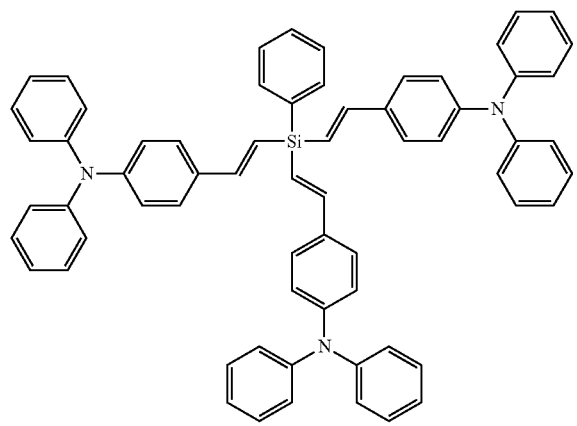

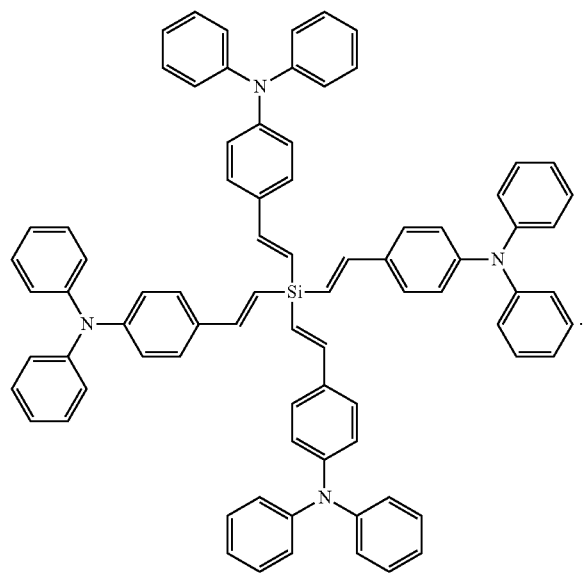

8. An organic light-emitting device comprising:
a first electrode;
a second electrode; and
an organic light-emitting layer between the first electrode and the second electrode,
wherein the organic layer comprises a vinylsilane compound represented by Formula 1:

$$(A)_n\text{-Si}\left(\begin{array}{c} R_1 \\ \diagup \\ \diagdown \\ R_2 \end{array}\text{-B-N}\begin{array}{c} Ar_1 \\ \diagdown \\ Ar_2 \end{array}\right)_m, \quad \text{Formula 1}$$

wherein:
each A is independently:
a substituted or unsubstituted $C_1$-$C_{60}$ alkyl group,
an unsubstituted $C_5$-$C_{60}$ aryl group,
a $C_5$-$C_{60}$ aryl group in which at least one hydrogen atom is substituted with a heavy hydrogen atom, a halogen atom, a hydroxyl group, a nitro group, a cyano group, an amino group, an amidino group, a hydrazine, a hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group, or
a substituted or unsubstituted $C_3$-$C_{60}$ heteroaryl group,
each of $R_1$ and $R_2$ is independently a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_5$-$C_{60}$ aryl group, or a substituted or unsubstituted $C_3$-$C_{60}$ heteroaryl group,
B is a bivalent linker and is a substituted or unsubstituted $C_1$-$C_{60}$ alkylene group, a substituted or unsubstituted $C_5$-$C_{60}$ arylene group, or a substituted or unsubstituted $C_3$-$C_{60}$ heteroarylene group,
$Ar_1$ and $Ar_2$ are optionally linked to form a

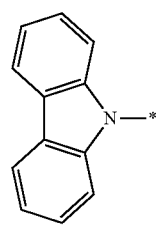 [SMILES: *n1c2ccccc2c2ccccc21]

ring with the N atom of Formula 1, or each of $Ar_1$ and $Ar_2$ is independently a group represented by any one of Formulae 3a, 3b and 3d through 3f:

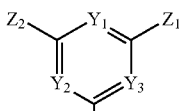

3a

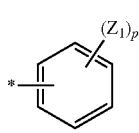

3b

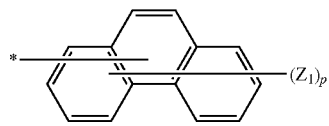

3d

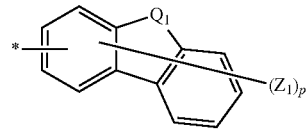

3e

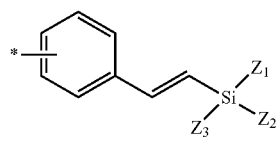

3f wherein, in Formulae 3a, 3b and 3d through 3f,
$Q_1$ is a linker represented by $-C(R_{30})(R_{31})-$, $-N(R_{32})-$, $-S-$, or $-O-$;
each of $Y_1$, $Y_2$, and $Y_3$ is a linker independently represented by $-O-$, $-N=$, $-N(R_{20})-$, or $-C(R_{21})=$,
each of $Z_1$, $Z_2$, $Z_3$, $R_{20}$, $R_{21}$, $R_{30}$, $R_{31}$, and $R_{32}$ is independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, or a carboxyl group;
p is an integer from 1 to 12; and
* indicates a binding site,
n is an integer from 0 to 3,
m is an integer from 1 to 4, and
n+m=4.

9. The organic light-emitting device of claim 8, wherein the organic layer is an emission layer, and the vinylsilane compound is a host for a fluorescent or phosphorescent device.

10. The organic light-emitting device of claim 8, wherein the organic layer is an emission layer, and the vinylsilane compound is a fluorescent dopant.

11. The organic light-emitting device of claim 8, wherein the organic layer comprises a hole injection layer, a hole transport layer, or a functional layer having both hole injection and hole transport capabilities.

12. The organic light-emitting device of claim 8, wherein the organic light-emitting device comprises:
an emission layer, and
a hole injection layer, a hole transport layer, or a functional layer having both hole injection and hole transport capabilities,
wherein the emission layer, the hole injection layer, the hole transport layer, or the functional layer having both hole injection and hole transport capabilities comprises the vinylsilane compound of claim 1, and
wherein the emission layer comprises an anthracene-based compound.

13. The organic light-emitting device of claim 8, wherein the organic light-emitting device comprises:
an emission layer, and
a hole injection layer, a hole transport layer, or a functional layer having both hole injection and hole transport capabilities,
wherein the emission layer, the hole injection layer, the hole transport layer, or the functional layer having both hole injection and hole transport capabilities comprises the vinylsilane compound of claim 1, and
wherein the emission layer comprises an arylamine-based compound.

14. The organic light-emitting device of claim 8, wherein the organic light-emitting device comprises:
an emission layer, and
a hole injection layer, a hole transport layer, or a functional layer having both hole injection and hole transport capabilities,
wherein the emission layer, the hole injection layer, the hole transport layer, or the functional layer having both hole injection and hole transport capabilities comprises the vinylsilane compound of claim 1, and
wherein the emission layer comprises a styryl-based compound.

15. The organic light-emitting device of claim 8, wherein the organic light-emitting device comprises:
an emission layer, and
a hole injection layer, a hole transport layer, or a functional layer having both hole injection and hole transport capabilities,
wherein the hole injection layer, the hole transport layer, or the functional layer having both hole injection or hole transport capabilities comprises the vinylsilane compound of claim 1, and
wherein a red layer, a green layer, or a white layer of the emission layer comprises a phosphorescent compound.

16. The organic light-emitting device of claim 15, wherein the hole injection layer, the hole transport layer, or the functional layer having both hole injection and hole transport capabilities comprises a charge generating material.

17. The organic light-emitting device of claim 16, wherein the charge generating material comprises a p-dopant, and
wherein the p-dopant comprises a quinone derivative, a metal oxide, or a cyano-containing compound.

18. The organic light-emitting device of claim 8, wherein the organic layer comprises an electron transport layer, and
wherein the electron transport layer comprises an electron transport organic compound and a metal complex.

19. The organic light-emitting device of claim 8, wherein the organic layer is formed by a wet method using the vinylsilane compound of claim 1.

20. A flat panel display device, comprising the organic light-emitting device of claim 8, wherein the first electrode of the organic light-emitting device is electrically connected to a source electrode or a drain electrode of a thin film transistor.

* * * * *